US012559724B2

(12) United States Patent
Günther et al.

(10) Patent No.: US 12,559,724 B2
(45) Date of Patent: Feb. 24, 2026

(54) GENETICALLY MODIFIED MESENCHYMAL STEM CELL EXPRESSING KLOTHO

(71) Applicant: apceth GmbH & Co. KG, Munich (DE)

(72) Inventors: Christine Günther, Munich (DE); Manfred Stangl, Sauerlach (DE); Felix Hermann, Munich (DE)

(73) Assignee: apceth GmbH & Co. KG, Munich (DE)

( * ) Notice: Subject to any disclaimer, the term of this patent is extended or adjusted under 35 U.S.C. 154(b) by 755 days.

(21) Appl. No.: 17/447,975

(22) Filed: Sep. 17, 2021

(65) Prior Publication Data

US 2022/0033779 A1 Feb. 3, 2022

Related U.S. Application Data

(63) Continuation of application No. 15/553,954, filed as application No. PCT/EP2016/054091 on Feb. 26, 2016, now abandoned.

(30) Foreign Application Priority Data

Feb. 27, 2015 (EP) ..................................... 15156974
Sep. 18, 2015 (EP) ..................................... 15185805
Oct. 22, 2015 (EP) ..................................... 15191062

(51) Int. Cl.
| | |
|---|---|
| *C12N 5/0775* | (2010.01) |
| *A61K 35/12* | (2015.01) |
| *A61K 35/28* | (2015.01) |
| *A61K 38/00* | (2006.01) |
| *A61K 38/47* | (2006.01) |
| *A61K 48/00* | (2006.01) |
| *C07K 14/435* | (2006.01) |
| *C12N 9/24* | (2006.01) |

(52) U.S. Cl.
CPC ............ *C12N 5/0663* (2013.01); *A61K 35/28* (2013.01); *A61K 38/47* (2013.01); *A61K 48/00* (2013.01); *C07K 14/435* (2013.01); *C12N 9/2402* (2013.01); *C12Y 302/01031* (2013.01); *A61K 2035/124* (2013.01); *A61K 38/00* (2013.01); *C12N 2501/73* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 6,579,850 | B1 | 6/2003 | Nabeshima et al. |
| 2003/0119910 | A1 | 6/2003 | Kamiya et al. |
| 2009/0192087 | A1 | 7/2009 | Glass et al. |
| 2011/0015345 | A1 | 1/2011 | Pinkstaff et al. |
| 2014/0010801 | A1 | 1/2014 | Niedernhofer et al. |

FOREIGN PATENT DOCUMENTS

| | | |
|---|---|---|
| WO | WO 2010/068707 A2 | 6/2010 |
| WO | WO 2010/119039 A1 | 10/2010 |
| WO | WO 2014/152993 A1 | 9/2014 |

OTHER PUBLICATIONS

Haruna, et al. 2007 "Amelioration of progressive renal injury by genetic manipulation of Klotho gene" *Proceedings of the National Academy of Sciences* 104(7):2331-2336.

Kurosu 2005 "Suppression of aging in mice by the hormone Klotho" *Science* 309(5742): 1829-1833.

Li, et al. 2013 "FGF23 affects the lineage fate determination of mesenchymal stem cells" *Calcified Tissue international* 93(6): 556-564.

Nagai, et al. 1997 "Mutation of the mouse klotho gene leads to a syndrome resembling ageing" *Nature* 390; 45-51.

Olauson, H. et al. 2017 "Tissue expression and source of circulating αKlotho" *Bone* 100: 19-35.

Varshney, et al. 2015 "Secreted klotho augments the therapeutic potential of mesenchymal stem cells for monocrotaline-induced pulmonary arterial hypertension" *The Faseb Journal* 29(1): in 1 page.

Doi et al. Klotho Inhibits Transforming Growth Factor-[31 (TGF-[31) Signaling and Suppresses Renal Fibrosis and Cancer Metastasis in Mice. The Journal of Biological Chemistry, 2011. 286(10):8655-8665.

(Continued)

*Primary Examiner* — Christopher M Babic
*Assistant Examiner* — Kimberly A Aron
(74) *Attorney, Agent, or Firm* — Knobbe, Martens, Olson & Bear, LLP

(57) ABSTRACT

A genetically modified mesenchymal stem cell including an exogenous nucleic acid including a Klotho encoding region operably linked to a promoter or promoter/enhancer combination, wherein the genetically modified mesenchymal stem cell exhibits increased Klotho expression compared to an unmodified mesenchymal stem cell. Also disclosed are methods of treating a patient including administering a therapeutically effective number of the genetically modified mesenchymal stem cells to the patient. The methods of treatment include treating the patient for a neurodegenerative disease; cancer; organ fibrosis; renal disease; age-related changes of organs or organ systems; to slow, reverse and/or inhibit aging; arteriosclerosis; dementia; diabetes mellitus; erectile dysfunction; autoimmune diseases or autoimmune-related diseases; an inflammatory disease of the lung and sepsis.

25 Claims, No Drawings
Specification includes a Sequence Listing.

(56) References Cited

OTHER PUBLICATIONS

Nolan et al. Association of Single Nucleotide Polymorphisms in Klotho with Priapism in Sickle Cell Anemia. British Journal of Haematology, 2004. 128:266-272.
Inoue et al. Sepsis-Induced Hypercytokinemia and Lymphocyte Apoptosis in Aging-Accelerated Klotho Knockout Mice. Shock, 2013. 39(3):311-316.
GenBank Accession No. AB005142, 1997. 3 pages.

GENETICALLY MODIFIED MESENCHYMAL STEM CELL EXPRESSING KLOTHO

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING

The present application is being filed along with a Sequence Listing in electronic format. The Sequence Listing is provided as a file entitled 54211326_1.TXT, created Sep. 17, 2021, which is 52.2 Kb in size. The information in the electronic format of the Sequence Listing is incorporated herein by reference in its entirety.

BACKGROUND

Field

The invention relates to a genetically modified mesenchymal stem cell (MSC), wherein said stem cell comprises an exogenous nucleic acid comprising a Klotho encoding region operably linked to a promoter or promoter/enhancer combination. The invention relates to the medical use of said MSCs for the treatment of cancer, organ fibrosis, renal failure, age-related organ pathologies, arteriosclerosis, neurodegenerative diseases, such as Alzheimer's disease (AD), Multiple sclerosis (MS), Huntington's disease, Amyotrophic Lateral Sclerosis (ALS), Parkinson's disease, and/or Schizophrenia, or dementia, diabetes mellitus, sepsis, erectile dysfunction, cardio vascular diseases and autoimmune diseases.

Description of the Related Art

Mesenchymal stem cells (MSCs) are cells of non-hematopoietic origin that reside in the bone marrow and other tissues. MSCs are commonly considered to be multipotent adult progenitor cells that have the ability to differentiate into a limited number of cell lineages, such as osteoblasts, chondrocytes, and adipocytes. Studies have been conducted on the use of MSCs as a therapeutic entity based on this capacity to differentiate directly into these end-stage phenotypes, including the use of MSCs to promote or augment bone repair and for the repair of cartilage defects (Vilquin and Rosset, Regenerative Medicine 2006: 1, 4, p 589, and Veronesi et al, Stem Cells and Development 2013; 22, p 181). The isolation and cultivation of MSCs for a number of therapeutic indications has been described and represents a promising approach towards treating inflammation-associated disorders (for example WO 2010/119039).

MSCs are known to exhibit immune evasive properties after administration to a patient. MSCs have been shown to exhibit a beneficial immune modulatory effect in cases of transplantation of allogeneic donor material (Le Blanc et al, Lancet 2004: 363, p 1439), thereby reducing a potentially pathogenic alloreactivity and rejection. Furthermore, MSCs are known to exhibit anti-tumorigenic effects, for example against Kaposi's sarcoma (Khakoo et al, J Exp Med 2006: 203, p 1235). MSCs treatment can also play a therapeutic role in wound healing. The therapeutic delivery of MSCs can be performed via systemic injection, followed by MSC homing to and engraftment within sites of injury (Kidd et al, Stem Cells 2009: 27, p 2614). Although it is clear that MSCs have a regenerative effect on injured tissue, their use as a delivery vehicle for therapeutic proteins of interest has not yet been fully explored.

The human Klotho gene encodes a type-1 transmembrane protein of 1012 amino acids, which can also be expressed as a secreted form by alternative splicing. Both forms have biological activity including regulatory effects on general metabolism. Klotho is a $\beta$-glucuronidase (EC number 3.2.1.31) capable of hydrolyzing steroid $\beta$-glucuronides.

Loss of Klotho in mice results in the early appearance of several pathological phenotypes that resemble human aging including a short lifespan, infertility, arteriosclerosis/vascular calcification, osteoporosis, skin atrophy, lung emphysema, acute kidney injury, chronic kidney disease, renal fibrosis, diabetes and cancer (Kuro-o, M. et al. Nature 1997, 390, p 45). In contrast, overexpression of Klotho has been shown to increase the life-span of mice (Kurosu, H. et al. Science 2005, 309, p 1829).

Klotho was detected in 1997 by Makoto Kuro-o, who found that mice missing Klotho exhibited syndromes that resemble human ageing, including a short lifespan. Klotho has been shown to be involved in the suppression of several ageing phenotypes. A defect in klotho gene expression in the mouse results in infertility, arteriosclerosis, skin atrophy, osteoporosis and emphysema (Kuro-o, M., et al. (1997), Nature 390, 45-51). The Klotho protein is most highly expressed in the kidney, brain and pituitary gland, and is present in lower levels within skeletal muscle, the urinary bladder, the ovary and the testes (Avin, K. G., et al. (2014), Frontiers in physiology 5, 189).

The Klotho protein exists in two forms: membrane Klotho and secreted Klotho. Membrane Klotho functions as a receptor for a hormone that regulates excretion of phosphate and synthesis of active vitamin D in the kidney. Secreted Klotho functions as a humoral factor with pleiotropic activities, including suppression of growth factor signaling, suppression of oxidative stress, and regulation of ion channels and transporters.

FGF23, a member of the fibroblast growth factor (FGF) family was identified to be elevated in patients with autosomal dominant hypophosphatemic rickets (ADHR). Thus FGF23 functions as a phosphaturic hormone and a counter-regulatory hormone for vitamin D (calcitriol) in a Klotho-dependent manner. Hyperphosphatemia leads to stenosis of blood vessels, myocardial infarction, stroke and a major shortening in life expectancy in patients with chronic kidney disease (CKD). The absence of FGF-signaling in the kidney results in increased serum levels of phosphate. It has been found that secreted and the membrane bound form of Klotho forms a complex together with the FGF-receptor and thereby increases FGF23-dependent signaling (Kurosu et al. Journal of Biological 2006), 281(10) pp. 6120-61). Klotho's function as a cofactor for FGF23 signaling is important for the regulation of the phosphate serum levels.

Furthermore, Klotho functions through the modulation of various signaling pathways including that of insulin growth factor 1 (IGF-1). One effect of Klotho is the increase in cellular resistance to oxidative stress, which is involved in many different pathological processes. It has been shown that through the modulation of the cellular response to oxidative stress Klotho also acts protectively in the context of neurodegenerative diseases such as Alzheimer's Disease (Zeldich, E. et al. J Biol Chem 2014, 289(35):24700) and diabetes mellitus (Lin, Y. et al. Diabetes 2014, DB140632). Klotho also has been suggested to be a repressor of collagen synthesis and therefore might be beneficial in the context of fibrosis (Ghosh, A. K. et al. Exp Biol Med 2013, 238(5): 461).

It has been shown that Klotho expression is silenced in several kinds of cancer cells, which is associated with enhanced cell growth and the formation of cancer metastasis (Camilli et al. Pgment Cell Melanoma Res 2011, 24(1), p'75; Wang et al, Am J Cancer Res 2011, 1(1):111, Lee et al, Molecular Cancer 2010, 9:109). In contrast, overexpression of Klotho in cancer cells can inhibit cell growth and can promotes apoptosis of cancer cells (Chen, B. et al. J of Exp and Clin Cancer Res 2010, 29:99). Furthermore, Klotho up-regulation indirectly stimulated by administration of renin-angiotensin system inhibitors or other compounds can lead to suppression of renal fibrosis (Ming Chang Hu et al, Contrib Nephrol 2013, 180:47) and there appears to be a correlation between low Klotho expression in diabetic rat models (Meng Fu Cheng et al, Journal of Biomedicine and Biotechnology, 2010, 513853).

Background on Chronic Kidney Disease (CKD):

CKD is a growing international health problem, affecting more than 26 million Americans. In patients with CKD renal Klotho RNA is decreased. This clinical observation was confirmed in numerous preclinical models, showing that unilateral nephrectomy and contralateral ischemia reperfusion injury downregulates renal klotho protein and mRNA expression. The same reduction in klotho expression was shown in a chronic glomerulonephritis model. Klotho overexpression improved renal function and ameliorated renal histology in this model (Hu, M. C., et al. (2011), Journal of the American Society of Nephrology: 22, 124-136, Haruna, Y., et al. (2007) PNAS, 104, 2331-2336).

In CKD patients, there is a very high prevalence coronary artery calcification, which increases cardiovascular morbidity and mortality. The klotho FGF 23 axis plays an important role in vascular mineralization (Stompor, T. (2014) World journal of cardiology 6, 115-129). Increased cardiovascular (CV) morbidity and mortality is well documented in chronic kidney disease (CKD). In a survey among 1,120,295 adults in the San Francisco Bay Area a strong correlation between renal function (estimated glomerular filtration rate, GFR) and cardiovascular events was found (Go, A. S., et al. (2004) The New England journal of medicine 351, 1296-1305).

In the Renal Research Institute (RRI)-CKD Study of adults with moderate to severe CKD (Stages 3-5), enrolled between June 2000 and February 2006 (n=834) the authors found that heart rate variability is predictive for clinical outcome and cardiovascular disease (CVD) (Chandra, P., et al. (2012) official publication of the European Dialysis and Transplant Association—European Renal Association 27, 700-709). Chronic kidney disease (CKD) is therefore a major risk factor for cardiovascular disease leading to increased morbidity and shortening of lifespan. Klotho expression is markedly reduced in kidneys from patients suffering from CKD. Restoring Klotho expression by infusion of MSC-Klotho may improve kidney function and thereby reduce the risk for cardiovascular death.

Background on Cardiovascular Disease:

Cardiovascular disease (CVD) is a prevalent condition in general population and the first cause of death overall. Klotho has been proposed as a key regulator of the development of CVD. In the few clinical studies made, it has been observed a relationship between low levels of soluble Klotho and the occurrence and severity of CVD, as well as a reduction of cardiovascular risk when they are high. Also, different polymorphisms of human Klotho gene have been related to the incidence of cardiovascular events. Moreover, several experimental studies indicate that this protein acts in the maintenance of vascular homeostasis (Yamamoto M. et al., J Biol Chem. 2005; 280: 38029-38034). Klotho improves endothelial dysfunction through promotion of NO production and mediates anti-inflammatory and anti-aging effects such as suppression of adhesion molecules expression, attenuation of nuclear factor-kappa B or inhibition of Wnt signaling. Klotho regulates expression levels of the endothelial NO synthase (eNOS). Six et al recently observed that attenuation mediated by Klotho of FGF23 or phosphate-induced vasoconstriction is abolished by adding nitro-L-arginine, a competitive inhibitor of NOS. Moreover, they observed that exposure of HUVECs to Klotho increased NO production and induced eNOS phosphorylation and iNOS expression. Interestingly, Klotho was able to increase $H_2O_2$ production in cultured human VSMCs (HVSMCs), which suggests a more complex effect of this protein on the regulation of vascular tone through mediation of a ROS/NO balance (Six I et al. (2014), PLoS One. 2014; 9:e93423.).

Furthermore, this protein is related to the attenuation of vascular calcification as well as prevention of cardiac hypertrophy. The expression of this protein in the vascular wall implies a new scenario for the treatment of vascular disorders. Klotho protein is therefore related to CVD and plays a role in the maintenance of functional vascular integrity (Martín-Núñez, M. (2014) World J Cardiol. 6(12): 1262-1269.).

Background on Morbus Alzheimer (AD):

Neurodegenerative diseases, especially Morbus Alzheimer (AD), are increasing in the western world. The Alzheimer's association estimates that in the USA Alzheimer's is the 6th leading cause of death, that every 67 seconds someone is diagnosed with Alzheimer's and that the cost for medical treatment and caregiving for these patients will exceed 1.1 trillion US $ by 2050. AD is characterized through the loss of neurons and synapses, but also through the generation of neurotoxic amyloid beta peptides (Aβ plaques) and their deposition along with neurofibrillary tangle formation. There is growing evidence, that the deposition of amyloid is the central hallmark of the disease. Activated astrocytes start an inflammatory reaction by producing proinflammatory cytokines like Il-6, Il-1 and TNF-α. All this starts with an improper reaction to oxidative stress, accumulation of oxygen free radicals, hyperglycemia and insulin resistance (Rosales-Corral, S., et al. (2015) Oxidative medicine and cellular longevity, 985845).

Recently it was shown, that in the cerebrospinal fluid of AD patients, the concentration of the anti-aging protein klotho is significantly lower than in younger patients or in old patients without AD (Semba, R. D., et al. (2014) *Neuroscience letters* 558, 37-40).

In the brain, Klotho protein is localized at the choroid plexus, where the protein is dominantly localized at the apical plasma membrane of ependymal cells. In kl–/– mouse brain, reduction of synapses was evident in the hippocampus, suggesting a role of Klotho as a humoral factor in the cerebrospinal fluid. Klotho protein in the kidney is localized at the distal renal tubules (Li S A, et al. (2004) Cell Structure and Function 29, 91-99).

Chen et al demonstrated, that loss of Klotho expression leads to cognitive deficits. They found significant effects of Klotho on oligodendrocyte functions, including induced maturation of rat primary oligodendrocytic progenitor cells (OPCs) in vitro and myelination. Klotho increased OPC maturation. In vivo studies of Klotho knock-out mice and control littermates revealed that knock-out mice have a significant reduction in major myelin protein and gene expression. By immunohistochemistry, the number of total and mature oligodendrocytes was significantly lower in Klotho knock-out mice. At the ultrastructural level, Klotho knock-out mice exhibited significantly impaired myelination of the optic nerve and corpus callosum (Chen, C. D., et al. (2013) The Journal of neuroscience 33, 1927-1939).

Background on Multiple Sclerosis (MS):

MS is a complex disease of the CNS that is characterized by heterogeneous pathologies composed of both inflammatory and neurodegenerative components. The most common histopathological feature at early stages of the disease includes intermittent episodes of acute inflammation within patches of white matter, resulting in demyelination. Myelin is critical for maintaining efficient axonal conduction and oligodendrocytes, the myelin producer and maintainer of axonal health within the CNS, are damaged or destroyed in MS patients. Endogenous oligodendrocyte precursor cells (OPCs) are found to be universally dispersed within the human CNS and can be found in high density within some subacute lesions during early stages of MS.

Progressive MS is the latest stage of the disease, characterized by a gradual worsening of symptoms without remission. Severe neurological impairments dramatically reduce the quality of life for the individual, and this is mainly attributed to expanding cortical lesions impacting motor function. Pathologically, there is widespread axonal degeneration and grey matter neuropathy. Diffuse white and gray matter inflammation has been reported, correlating, in part, to global microglial activation as well as the presence of T cells, B cells and myelin-laden macrophages. Furthermore, there is an overall failure of OPCs to efficiently remyelinate damaged white and gray matter areas, dramatically reducing the possibility for recovery (Chang, A., et al. (2002) The New England journal of medicine 346, 165-173). Klotho enhances the maturation of OPCs into mature oligodendrocytes (Chen, C. D., et al. (2013) The Journal of neuroscience 33, 1927-1939).

Background on Amyotrophic Lateral Sclerosis (ALS):

ALS is a neurodegenerative disease of motor neurons with no effective treatment. Wnt signaling plays important roles in nervous system development and function, including axon guidance, synapse formation and plasticity and has also been associated with neurodegenerative diseases, including Alzheimer disease, Parkinson disease and ALS. Axon degeneration is an important step in disease progression.

The mechanisms underlying motor neuron cell death and axonal degeneration in ALS remain elusive. Tury et al found, that two non-canonical Wnt signaling components, aPKC and Ryk, which are important regulators of axon growth and plasticity in both developing embryos and in adult nervous system, were clearly up regulated in the spinal cord of SOD1 (G93A) mice, providing evidence that Wnt signaling is altered in ALS and might be involved in disease etiology and pathogenesis (Tury, A., et al. (2014) Developmental neurobiology 74, 839-850). A coimmunoprecipitation study indicated that soluble klotho binds to various Wnt family members, including Wnt1, Wnt3, Wnt4, and Wnt5a, suppresses Wnt transcription, and inhibits Wnt biological activity in the skin. An overexpression of klotho effectively antagonizes the activity of endogenous and exogenous Wnt, which induces accelerated cell senescence both in vitro and in vivo (Liu, H., et al. (2007) Science 317, 803-806).

Background on Parkinson Disease (PD):

PD is a progressive neurodegenerative disorder clinically characterized by the cardinal symptoms of resting tremor, bradykinesia, cogwheel rigidity, and postural instability.

Responsiveness to L-3,4-dihydroxyphen-ylalanine (L-DOPA) and brain imaging distinguish PD from other disorders. The pathological hallmarks of PD are loss of dopaminergic cells in the substantia nigra pars compacta and subsequent loss of dopamine innervation in the striatum. Motor symptoms are the most obvious consequence of this nigrostriatal neurodegeneration. However, not only the basal ganglia but also other parts of the central nervous system as well as the autonomic nervous system are affected. A wide range of resulting non-motor symptoms can affect the patient's quality of life. There is also a broad consensus that neurodegenerative processes in PD start many years before the actual onset of clinical symptoms. The phenotypical over-lapping between familial and idiopathic PD is sufficient to dissect the commonly involved pathways. These include mitochondrial dysfunction, oxidative stress, protein misfolding, protein degradation, protein aggregation, and inflammation.

Kosakai et al demonstrated that the number of tyrosine-hydroxylase-positive dopaminergic neurons in the substancia nigra pars compacta and the ventral tegmental area and the striatal dopamine level in klotho-insufficient mice were significantly decreased in age-dependent fashion. These phenotypic features were completely rescued by vitamin D restriction, indicating that abnormal increase in active vitamin D biosynthesis by Klotho insufficiency induces degeneration of dopaminergic neurons (Kosakai, A., et al. (2011) Brain research 1382, 109-117).

Due to its diverse functional roles in multiple organ systems and its potential beneficial effect in various diseases, novel treatments incorporating Klotho administration may represent promising therapeutic approaches. Until the present time the therapeutic administration of Klotho remains largely unexplored. Effective therapeutic regimes, especially those enabling local administration or local expression of Klotho in disease-affected physiological niches, or methods of providing continual Klotho protein expression in vivo, have not been described in the art.

SUMMARY

In light of the prior art the technical problem underlying the present invention is to provide alternative and/or improved means for the treatment of diseases, particularly cancer, organ fibrosis, renal failure, age-related organ pathologies, arteriosclerosis, dementia, neurodegenerative diseases, such as Alzheimer's disease (AD), Multiple sclerosis (MS), Huntington's disease, Amyotrophic Lateral Sclerosis (ALS), Parkinson's disease, and/or Schizophrenia, diabetes mellitus, sepsis, erectile dysfunction or autoimmune diseases.

This problem is solved by the features of the independent claims. Preferred embodiments of the present invention are provided by the dependent claims.

The invention therefore relates to a genetically modified mesenchymal stem cell, wherein said stem cell comprises an exogenous nucleic acid comprising a Klotho encoding region operably linked to a promoter or promoter/enhancer combination. Such MSCs may be referred to as "Klotho-modified MSCs" or "MSC-Klotho". A Klotho encoding region relates to any nucleic acid sequence that encodes any given Klotho protein, encompassing but not limited to those Klotho protein variants described herein.

One preferred amino acid sequence of Klotho is available under accession number BAA23382 from the NCBI database. Said amino acid sequence corresponds to the α-Klotho isoform. Corresponding nucleic acid sequences that encode Klotho may be provided by a person skilled in the art of molecular biology or genetics. The use of sequence variants of Klotho that exhibit functional analogy to the unmodified human form is also encompassed by the present invention.

Moreover the invention also relates to further isoforms of the Klotho gene and encompasses β-Klotho and γ-Klotho.

Preferred sequences of the invention relate to those provided below in Table 1. SEQ ID NO 1 relates to a sequence of the complete human Klotho gene (cDNA) with the naturally occurring sequence.

SEQ ID NO 2 relates to a codon optimized sequence (for translation in human cells) of the complete human Klotho gene (cDNA), as most preferred according to the present invention. The encoded amino acid sequence for SEQ ID NO 1 and SEQ ID NO 2 are identical. SEQ ID NO 3 relates to a sequence of the soluble form of the Klotho gene (cDNA) with the naturally occurring sequence.

SEQ ID NO 4 relates to a sequence of the human β-Klotho gene (cDNA) with the naturally occurring sequence.

SEQ ID NO 5 relates to a sequence of the human γ-Klotho gene (cDNA) with the naturally occurring sequence Further sequence variants are hereby incorporated in the invention that exhibit an alternative nucleic acid sequence to SEQ ID NO 1-5 but encode the same or a corresponding or functionally analogous amino acid sequence. Sequence variants obtained via using degeneracy of the genetic code are included. Sequence optimized nucleic acid sequences of those sequences provided herein are also included within the scope of the invention.

TABLE 1

Preferred Klotho sequences.

| SEQ ID NO 1: Human Klotho full length (membrane-bound) cDNA-Sequence (Pubmed: NM_004795.3) Signal peptide (Pos. 1-52) | ATGCCCGCCAGCGCCCCGCCGCGCCGCCCGCGGCCGCC GCCGCCGTCGCTGTCGCTGCTGCTGGTGCTGCTGGGCC TGGGCGGCCGCCGCCTGCGTGCGGAGCCGGGCGACGG CGCGCAGACCTGGGCCCGTTTCTCGCGGCCTCCTGCCC CCGAGGCCGCGGGCCTCTTCCAGGGCACCTTCCCCGAC GGCTTCCTCTGGGCCGTGGGCAGCGCCGCCTACCAGAC CGAGGGCGGCTGGCAGCAGCACGGCAAGGGTGCGTCC ATCTGGGATACGTTCACCCACCACCCCCTGGCACCCCC GGGAGACTCCCGGAACGCCAGTCTGCCGTTGGGCGCCC CGTCGCCGCTGCAGCCCGCCACCGGGGACGTAGCCAG CGACAGCTACAACAACGTCTTCCGCGACACGGAGGCG CTGCGCGAGCTCGGGGTCACTCACTACCGCTTCTCCAT CTCGTGGGCGCGAGTGCTCCCCAATGGCAGCGCGGGC GTCCCCAACCGCGAGGGGCTGCGCTACTACCGGCGCCT GCTGGAGCGGCTGCGGGAGCTGGGCGTGCAGCCCGTG GTCACCCTGTACCACTGGGACCTGCCCCAGCGCCTGCA GGACGCCTACGGCGGCTGGGCCAACCGCGCCCTGGCC GACCACTTCAGGGATTACGCGGAGCTCTGCTTCCGCCA CTTCGGCGGTCAGGTCAAGTACTGGATCACCATCGACA ACCCCTACGTGGTGGCCTGGCACGGCTACGCCACCGGG CGCCTGGCCCCCGGCATCCGGGGCAGCCCGCGGCTCGG GTACCTGGTGGCGCACAACCTCCTCCTGGCTCATGCCA AAGTCTGGCATCTCTACAATACTTCTTTCCGTCCCACTC AGGGGAGGTCAGGTGTCCATTGCCCTAAGCTCTCACTGG ATCAATCCTCGAAGAATGACCGACCACAGCATCAAAG AATGTCAAAAATCTCTGGACTTTGTACTAGGTTGGTTT GCCAAACCCGTATTTATTGATGGTGACTATCCCGAGAG CATGAAGAATAACCTTTCATCTATTCTGCCTGATTTTAC TGAATCTGAGAAAAAGTTCATCAAAGGAACTGCTGACT TTTTTGCTCTTTGCTTTGGACCCACCTTGAGTTTTCAAC TTTTGGACCCTCACATGAAGTTCCGCCAATTGGAATCT CCCAACCTGAGGCAACTGCTTTCCTGGATTGACCTTGA ATTTAACCATCCTCAAATATTTATTGTGGAAAATGGCT GGTTTGTCTCAGGGACCACCAAGAGAGATGATGCCAA ATATATGTATTACCTCAAAAAGTTCATCATGGAAACCT TAAAAGCCATCAAGCTGGATGGGGTGGATGTCATCGG GTATACCGCATGGTCCCTCATGGATGGTTTCGAGTGGC ACAGAGGTTACAGCATCAGGCGTGGACTCTTCTATGTT GACTTTCTAAGCCAGGACAAGATGTTGTTGCCAAAGTC TTCAGCCTTGTTCTACCAAAAGCTGATAGAGAAAAATG GCTTCCCTCCTTTACCTGAAAATCAGCCCCTAGAAGGG ACATTTCCCTGTGACTTTGCTTGGGGAGTTGTTGACAA CTACATTCAAGTAGATACCACTCTGTCTCAGTTTACCG ACCTGAATGTTTACCTGTGGGATGTCCACCACAGTAAA AGGCTTATTAAAGTGGATGGGGTTGTGACCAAGAAGA GGAAATCCTACTGTGTTGACTTTGCTGCCATCCAGCCC CAGATCGCTTTACTCCAGGAAATGCACGTTACACATTT TCGCTTCTCCCTGGACTGGGCCCTGATTCTCCCTCTGGG TAACCAGTCCCAGGTGAACCACACCATCCTGCAGTACT ATCGCTGCATGGCCAGCGAGCTTGTCCGTGTCAACATC ACCCCAGTGGTGGCCCTGTGGCAGCCTATGGCCCCGAA CCAAGGACTGCCGCGCCTCCTGGCCAGGCAGGGCGCCT GGGAGAACCCCTACACTGCCCTGGCCTTTGCAGAGTAT GCCCGACTGTGCTTTCAAGAGCTCGGCCATCACGTCAA GCTTTGGATAACGATGAATGAGCCGTATACAAGGAAT ATGACATACAGTGCTGGCCACAACCTTCTGAAGGCCCA TGCCCTGGCTTGGCATGTGTACAATGAAAAGTTTAGGC ATGCTCAGAATGGGAAAATATCCATAGCCTTGCAGGCT |

TABLE 1-continued

Preferred Klotho sequences.

|  |  |
|---|---|
|  | GATTGGATAGAACCTGCCTGCCCTTTCTCCCAAAAGGA |
|  | CAAAGAGGTGGCTGAGAGAGTTTTGGAATTTGACATTG |
|  | GCTGGCTGGCTGAGCCCATTTTCGGCTCTGGAGATTAT |
|  | CCATGGGTGATGAGGGACTGGCTGAACCAAAGAAACA |
|  | ATTTTCTTCTTCCTTATTTCACTGAAGATGAAAAAAAGC |
|  | TAATCCAGGGTACCTTTGACTTTTTGGCTTTAAGCCATT |
|  | ATACCACCATCCTTGTAGACTCAGAAAAAGAAGATCCA |
|  | ATAAAATACAATGATTACCTAGAAGTGCAAGAAATGA |
|  | CCGACATCACGTGGCTCAACTCCCCCAGTCAGGTGGCG |
|  | GTAGTGCCCTGGGGGTTGCGCAAAGTGCTGAACTGGCT |
|  | GAAGTTCAAGTACGGAGACCTCCCCATGTACATAATAT |
|  | CCAATGGAATCGATGACGGGCTGCATGCTGAGGACGA |
|  | CCAGCTGAGGGTGTATTATATGCAGAATTACATAAACG |
|  | AAGCTCTCAAAGCCCACATACTGGATGGTATCAATCTT |
|  | TGCGGATACTTTGCTTATTCGTTTAACGACCGCACAGC |
|  | TCCGAGGTTTGGCCTCTATCGTTATGCTGCAGATCAGTT |
|  | TGAGCCCAAGGCATCCATGAAACATTACAGGAAAATT |
|  | ATTGACAGCAATGGTTTCCCGGGCCCAGAAACTCTGGA |
|  | AAGATTTTGTCCAGAAGAATTCACCGTGTGTACTGAGT |
|  | GCAGTTTTTTTCACACCCGAAAGTCTTTACTGGCTTTCA |
|  | TAGCTTTTCTATTTTTTGCTTCTATTATTTCTCTCTCCCT |
|  | TATATTTTACTACTCGAAGAAAGGCAGAAGAAGTTACA |
|  | AATAG |
| SEQ ID NO 2: Human | ATGCCCGCCAGCGCCCCTCCAAGAAGGCCTAGACCTCC |
| Klotho full length | TCCACCTAGCCTGAGCCTGCTGCTGGTGCTGCTGGGAC |
| (membrane-bound) | TGGGAGGAAGAAGGCTGAGAGCCGAACCTGGGGATGG |
| cDNA-Sequence as | CGCCCAGACATGGGCCAGATTCTCTAGACCACCCGCCC |
| preferably used in the | CTGAAGCCGCCGGACTGTTTCAGGGAACCTTCCCCGAT |
| constructs of the present | GGCTTCCTGTGGGCCGTGGGATCTGCCGCCTATCAGAC |
| invention. The sequence | TGAAGGGGGCTGGCAGCAGCACGGCAAGGGCGCCTCT |
| has been codon-optimized | ATCTGGGACACCTTCACCCACCATCCTCTGGCCCCACC |
| and has an additional | CGGCGACAGCAGAAATGCTTCTCTGCCTCTGGGAGCCC |
| HA-Tag (3037-3063; | CCAGCCCTCTGCAGCCTGCTACAGGGGATGTGGCCAGC |
| underlined text in the | GACAGCTACAACAACGTGTTCCGGGACACAGAGGCCC |
| sequence) for detection at | TGCGGGAACTGGGCGTGACCCACTACAGATTCAGCATC |
| the 3'-end of the | AGCTGGGCCAGAGTGCTGCCCAATGGCTCTGCCGGCGT |
| sequence, STOP | GCCCAATAGAGAGGGCCTGCGGTACTACCGGCGGCTG |
| (3064-3072; provided in | CTGGAAAGACTGAGAGAACTGGGAGTGCAGCCCGTCG |
| bold text within the | TGACCCTGTACCATTGGGACCTGCCCCAGAGACTGCAG |
| sequence) | GATGCCTATGGCGGCTGGGCCAATAGAGCCCTGGCCG |
| Signal peptide (Pos. 1-52) | ACCACTTCAGAGACTACGCCGAGCTGTGCTTCCGGCAC |
|  | TTTGGCGGCCAAGTGAAGTACTGGATCACCATCGACAA |
|  | CCCCTACGTGGTGGCCTGGCACGGCTATGCCACAGGCA |
|  | GACTGGCCCCTGGCATCAGAGGAAGCCCTAGACTGGG |
|  | CTACCTGGTGGCCCACAATCTGCTGCTGGCCCACGCTA |
|  | AAGTGTGGCACCTGTACAACACCAGCTTCCGGCCTACA |
|  | CAGGGCGGCCAGGTGTCCATTGCCCTGAGCAGCCACTG |
|  | GATCAACCCCAGACGGATGACCGACCACAGCATCAAA |
|  | GAGTGCCAGAAAAGCCTGGACTTCGTGCTGGGATGGTT |
|  | CGCCAAGCCCGTGTTCATCGACGGCGACTACCCCGAGA |
|  | GCATGAAGAACAACCTGTCCAGCATCCTGCCCGACTTC |
|  | ACCGAGAGCGAGAAGAAGTTCATCAAGGGCACCGCCG |
|  | ATTTCTTCGCCCTGTGCTTCGGCCCTACCCTGAGCTTCC |
|  | AGCTGCTGGACCCCCACATGAAGTTCAGACAGCTGGA |
|  | AAGCCCCAACCTGCGGCAGCTGCTGAGCTGGATCGACC |
|  | TGGAATTCAACCACCCCAGATTTTCATCGTGGAAAAC |
|  | GGCTGGTTCGTGTCCGGCACCACCAAGAGGGACGACG |
|  | CCAAGTACATGTATTACCTGAAAAAGTTTATCATGGAA |
|  | ACCCTGAAGGCCATCAAGCTGGACGGCGTGGACGTGA |
|  | TCGGCTACACAGCCTGGTCCCTGATGGACGGCTTCGAG |
|  | TGGCACCGGGGCTACTCTATCAGACGGGGCCTGTTCTA |
|  | CGTGGACTTCCTGAGCCAGGACAAGATGCTGCTGCCTA |
|  | AGAGCAGCGCCCTGTTTTACCAGAAGCTGATCGAGAA |
|  | GAACGGCTTCCCACCCCTGCCCGAGAACCAGCCTCTGG |
|  | AAGGCACCTTCCCCTGCGATTTTGCCTGGGGCGTGGTG |
|  | GACAACTACATCCAGGTGGACACCACCCTGTCCCAGTT |
|  | CACCGACCTGAACGTGTACCTGTGGGACGTGCACCACA |
|  | GCAAGCGGCTGATTAAGGTGGACGGGGTCGTGACCAA |
|  | GAAGCGGAAGTCCTACTGCGTGGACTTTGCCGCCATCC |
|  | AGCCCCAGATTGCCCTGCTGCAGGAAATGCACGTGACA |
|  | CACTTCCGGTTCTCCCTGGACTGGGCCCTGATCCTGCC |
|  | ACTGGGCAATCAGAGCCAAGTGAACCACACCATTCTGC |
|  | AGTACTACAGATGCATGGCCTCCGAGCTGGTGCGCGTG |
|  | AACATCACACCTGTGGTGGCCCTGTGGCAGCCCATGGC |
|  | CCCTAATCAGGGACTGCCTAGACTGCTGGCTAGACAGG |
|  | GCGCCTGGGAGAACCCTTACACCGCCCTGGCCTTTGCC |
|  | GAGTACGCCCGGCTGTGTTTCCAGGAACTGGGGCACCA |

TABLE 1-continued

Preferred Klotho sequences.

```
CGTGAAGCTGTGGATCACAATGAACGAGCCCTACACCC
GGAACATGACCTACAGCGCCGGACATAACCTGCTGAA
GGCCCACGCCCTGGCTTGGCATGTGTACAACGAGAAGT
TCCGGCACGCCCAGAACGGCAAGATCAGTATCGCCCTG
CAGGCCGACTGGATCGAGCCCGCCTGTCCCTTCAGCCA
GAAAGACAAAGAGGTGGCCGAGCGGGTGCTGGAATTC
GACATTGGATGGCTGGCCGAGCCCATCTTCGGCAGCGG
CGATTACCCCTGGGTCATGCGGGACTGGCTGAACCAGC
GGAACAACTTCCTGCTGCCTTACTTTACCGAGGATGAG
AAGAAACTGATCCAGGGGACCTTCGACTTCCTGGCCCT
GAGCCACTACACCACAATCCTGGTGGACAGCGAGAAA
GAGGACCCCATCAAGTACAACGACTACCTGGAAGTGC
AGGAAATGACCGACATCACCTGGCTGAATAGCCCCTCC
CAGGTGGCCGTGGTGCCTTGGGGACTGAGAAAGGTGC
TGAATTGGCTGAAGTTTAAGTACGGCGACCTGCCCATG
TACATCATCAGCAACGGCATCGACGATGGCCTGCACGC
CGAGGACGATCAGCTGCGGGTGTACTACATGCAGAAC
TACATCAACGAGGCCCTGAAAGCCCACATCCTGGACG
GCATCAACCTGTGCGGCTACTTCGCCTACAGCTTCAAC
GACCGGACCGCCCCTAGATTCGGCCTGTACAGATACGC
CGCCGACCAGTTCGAGCCCAAGGCCAGCATGAAGCAC
TACCGGAAGATCATCGACAGCAATGGCTTCCCTGGCCC
CGAGACACTGGAACGGTTCTGCCCCGAGGAATTCACCG
TGTGTACCGAGTGCAGCTTCTTCCACACCAGAAAGTCC
CTGCTGGCTTTTATCGCCTTCCTGTTCTTCGCCAGCATC
ATCTCCCTGTCCCTGATCTTCTACTACAGCAAGAAGGG
CAGACGGTCCTACAAGTACCCCTACGACGTGCCCGACT
ACGCCTGATGATGA
```

SEQ ID NO 3: Human
Klotho (secreted)
cDNA-Sequence
(Pubmed: AB009667.2)
Signal peptide (Pos. 1-52)

```
ATGCCCGCCAGCGCCCCGCCGCGCCGCCCGCGGCCGCC
GCCGCAGTCGCTGTCGCTGCTGCTGGTGCTGCTGGGCC
TGGGCGGCCGCCGCCTGCGTGCGGAGCCGGGCGACGG
CGCGCAGACCTGGGCCCGTTTCTCGCGCGCCTCCTGCCC
CCGAGGCCGCGGGCCTCTTCCAGGGCACCTTCCCCGAC
GGCTTCCTCTGGGCCGTGGGCAGCGCCGCCTACCAGAC
CGAGGGCGGCTGGCAGCAGCACGGCAAGGGTGCGTCC
ATCTGGGACACGTTCACCCACCACCCCCTGGCACCCCC
GGGAGACTCCCGGAACGCCAGTCTGCCGTTGGGCGCCC
CGTCGCCGCTGCAGCCCGCCACCGGGGACGTAGCCAG
CGACAGCTACAACAACGTCTTCCGCGACACGGAGGCG
CTGCGCGAGCTCGGGGTCACTCACTACCGCTTCTCCAT
CTCGTGGGCGCGAGTGCTCCCCAATGGCAGCGCGGGC
GTCCCCAACCGCGAGGGGCTGCGCTACTACCGGCGCCT
GCTGGAGCGGCTGCGGGAGCTGGGCGTGCAGCCCGTG
GTCACCCTGTACCACTGGGACCTGCCCCAGCGCCTGCA
GGACGCCTACGGCGGCTGGGCCAACCGCGCCCTGGCC
GACCACTTCAGGGATTACGCGGAGCTCTGCTTCCGCCA
CTTCGGCGGTCAGGTCAAGTACTGGATCACCATCGACA
ACCCCTACGTGGTGGCCTGGCACGGCTACGCCACCGGG
CGCCTGGCCCCCGGCATCCGGGGCAGCCCGCGGCTCGG
GTACCTGGTGGCGCACAACCTCCTCCTGGCTCATGCCA
AAGTCTGGCATCTCTACAATACTTCTTTCCGTCCCACTC
AGGGAGGTCAGGTGTCCATTGCCCTAAGCTCTCACTGG
ATCAATCCTCGAAGAATGACCGACCACAGCATCAAAG
AATGTCAAAAATCTCTGGACTTTGTACTAGGTTGGTTT
GCCAAACCCGTATTTATTGATGGTGACTATCCCGAGAG
CATGAAGAATAACCTTTCATCTATTCTGCCTGATTTTAC
TGAATCTGAGAAAAAGTTCATCAAAGGAACTGCTGACT
TTTTTGCTCTTTGCTTTGGACCCACCTTGAGTTTTCAAC
TTTTGGACCCTCACATGAAGTTCCGCCAATTGGAATCT
CCCAACCTGAGGCAACTGCTTTCCTGGATTGACCTTGA
ATTTAACCATCCTCAAATATTTATTGTGGAAAATGGCT
GGTTTGTCTCAGGGACCACCAAGAGAGATGATGCCAA
ATATATGTATTACCTCAAAAAGTTCATCATGGAAACCT
TAAAAGCCATCAAGCTGGATGGGGTGGATGTCATCGG
GTATACCGCATGGTCCCTCATGGATGGTTTCGAGTGGC
ACAGAGGTTACAGCATCAGGCGTGGACTCTTCTATGTT
GACTTTCTAAGCCAGGACAAGATGTTGTTGCCAAAGTC
TTCAGCCTTGTTCTACCAAAAGCTGATAGAGAAAAATG
GCTTCCCTCCTTTACCTGAAAATCAGCCCCTAGAAGGG
ACATTTCCCTGTGACTTTGCTTGGGGAGTTGTTGACAA
CTACATTCAAGTAAGTCAGCTGACAAAACCAATCAGCA
GTCTCACCAAGCCCTATCACTAG
```

SEQ ID NO 4: Human
β-Klotho cDNA-Sequence
(Pubmed: NM_175737.3;
bp 98-3232)

```
ATGAAGCCAGGCTGTGCGGCAGGATCTCCAGGGAATG
AATGGATTTTCTTCAGCACTGATGAAATAACCACACGC
TATAGGAATACAATGTCCAACGGGGGATTGCAAAGAT
CTGTCATCCTGTCAGCACTTATTCTGCTACGAGCTGTTA
```

TABLE 1-continued

Preferred Klotho sequences.

```
CTGGATTCTCTGGAGATGGAAGAGCTATATGGTCTAAA
AATCCTAATTTTACTCCGGTAAATGAAAGTCAGCTGTT
TCTCTATGACACTTTCCCTAAAAACTTTTTCTGGGGTAT
TGGGACTGGAGCATTGCAAGTGGAAGGGAGTTGGAAG
AAGGATGGAAAAGGACCTTCTATATGGGATCATTTCAT
CCACACACACCTTAAAAATGTCAGCAGCACGAATGGTT
CCAGTGACAGTTATATTTTTCTGGAAAAAGACTTATCA
GCCCTGGATTTTATAGGAGTTTCTTTTTATCAATTTTCA
ATTTCCTGGCCAAGGCTTTTCCCCGATGGAATAGTAAC
AGTTGCCAACGCAAAAGGTCTGCAGTACTACAGTACTC
TTCTGGACGCTCTAGTGCTTAGAAACATTGAACCTATA
GTTACTTTATACCACTGGGATTTGCCTTTGGCACTACAA
GAAAAATATGGGGGGTGGAAAAATGATACCATAATAG
ATATCTTCAATGACTATGCCACATACTGTTTCCAGATGT
TTGGGGACCGTGTCAAATATTGGATTACAATTCACAAC
CCATATCTAGTGGCTTGGCATGGGTATGGGACAGGTAT
GCATGCCCCTGGAGAGAAGGGAAATTTAGCAGCTGTCT
ACACTGTGGGACACAACTTGATCAAGGCTCACTCGAAA
GTTTGGCATAACTACAACACACATTTCCGCCCACATCA
GAAGGGTTGGTTATCGATCACGTTGGGATCTCATTGGA
TCGAGCCAAACCGGTCGGAAAACACGATGGATATATT
CAAATGTCAACAATCCATGGTTTCTGTGCTTGGATGGT
TTGCCAACCCTATCCATGGGGATGGCGACTATCCAGAG
GGGATGAGAAAGAAGTTGTTCTCCGTTCTACCCATTTT
CTCTGAAGCAGAGAAGCATGAGATGAGAGGCACAGCT
GATTTCTTTGCCTTTTCTTTTGGACCCAACAACTTCAAG
CCCCTAAACACCATGGCTAAAATGGGACAAAATGTTTC
ACTTAATTTAAGAGAAGCGCTGAACTGGATTAAACTGG
AATACAACAACCCTCGAATCTTGATTGCTGAGAATGGC
TGGTTCACAGACAGTCGTGTGAAAACAGAAGACACCA
CGGCCATCTACATGATGAAGAATTTCCTCAGCCAGGTG
CTTCAAGCAATAAGGTTAGATGAAATACGAGTGTTTGG
TTATACTGCCTGGTCTCTCCTGGATGGCTTTGAATGGCA
GGATGCTTACACCATCCGCCGAGGATTATTTTATGTGG
ATTTTAACAGTAAACAGAAAGAGCGGAAACCTAAGTC
TTCAGCACACTACTACAAACAGATCATACGAGAAAAT
GGTTTTTCTTTAAAAGAGTCCACGCCAGATGTGCAGGG
CCAGTTTCCCTGTGACTTCTCCTGGGGTGTCACTGAATC
TGTTCTTAAGCCCGAGTCTGTGGCTTCGTCCCCACAGTT
CAGCGATCCTCATCTGTACGTGTGGAACGCCACTGGCA
ACAGACTGTTGCACCGAGTGGAAGGGGTGAGGCTGAA
AACACGACCCGCTCAATGCACAGATTTTGTAAACATCA
AAAAACAACTTGAGATGTTGGCAAGAATGAAAGTCAC
CCACTACCGGTTTGCTCTGGATTGGGCCTCGGTCCTTCC
CACTGGCAACCTGTCCGCGGTGAACCGACAGGCCCTGA
GGTACTACAGGTGCGTGGTCAGTGAGGGGCTGAAGCTT
GGCATCTCCGCGATGGTCACCCTGTATTATCCGACCCA
CGCCCACCTAGGCCTCCCCGAGCCTCTGTTGCATGCCG
ACGGGTGGCTGAACCCATCGACGGCCGAGGCCTTCCA
GGCCTACGCTGGGCTGTGCTTCCAGGAGCTGGGGGACC
TGGTGAAGCTCTGGATCACCATCAACGAGCCTAACCGG
CTAAGTGACATCTACAACCGCTCTGGCAACGACACCTA
CGGGGCGGCGCACAACCTGCTGGTGGCCCACGCCCTG
GCCTGGCGCCTCTACGACCGGCAGTTCAGGCCCTCACA
GCGCGGGGCCGTGTCGCTGTCGCTGCACGCGGACTGGG
CGGAACCCGCCAACCCCTATGCTGACTCGCACTGGAGG
GCGGCCGAGCGCTTCCTGCAGTTCGAGATCGCCTGGTT
CGCCGAGCCGCTCTTCAAGACCGGGGACTACCCCGCGG
CCATGAGGGAATACATTGCCTCCAAGCACCGACGGGG
GCTTTCCAGCTCGGCCCTGCCGCGCCTCACCGAGGCCG
AAAGGAGGCTGCTCAAGGGCACGGTCGACTTCTGCGC
GCTCAACCACTTCACCACTAGGTTCGTGATGCACGAGC
AGCTGGCCGGCAGCCGCTACGACTCGGACAGGGACAT
CCAGTTTCTGCAGGACATCACCCGCCTGAGCTCCCCCA
CGCGCCTGGCTGTGATTCCCTGGGGGGTGCGCAAGCTG
CTGCGGTGGGTCCGGAGGAACTACGGCGACATGGACA
TTTACATCACCGCCAGTGGCATCGACGACCAGGCTCTG
GAGGATGACCGGCTCCGGAAGTACTACCTAGGGAAGT
ACCTTCAGGAGGTGCTGAAAGCATACCTGATTGATAAA
GTCAGAATCAAAGGCTATTATGCATTCAAACTGGCTGA
AGAGAAATCTAAACCCAGATTTGGATTCTTCACATCTG
ATTTTAAAGCTAAATCCTCAATACAATTTTACAACAAA
GTGATCAGCAGCAGGGGCTTCCCTTTTGAGAACAGTAG
TTCTAGATGCAGTCAGACCCAAGAAAATACAGAGTGC
ACTGTCTGCTTATTCCTTGTGCAGAAGAAACCACTGAT
ATTCCTGGGTTGTTGCTTCTTCTCCACCCTGGTTCTACT
```

TABLE 1-continued

Preferred Klotho sequences.

|  |  |
|---|---|
|  | CTTATCAATTGCCATTTTTCAAAGGCAGAAGAGAAGAA |
|  | AGTTTTGGAAAGCAAAAAACTTACAACACATACCATTA |
|  | AAGAAAGGCAAGAGAGTTGTTAGCTAA |
|  |  |
| SEQ ID NO 5: Human | ATGAAGCCAGTGTGGGTCGCCACCCTTCTGTGGATGCT |
| γ-Klotho cDNA-Sequence | ACTGCTGGTGCCCAGGCTGGGGGCCGCCCGGAAGGGG |
| *Homo sapiens* lactase like | TCCCCAGAAGAGGCCTCCTTCTACTATGGAACCTTCCC |
| (LCTL), transcript variant | TCTTGGCTTCTCCTGGGGCGTGGGCAGTTCTGCCTACC |
| 1, cDNA | AGACGGAGGGCGCCTGGGACCAGGACGGGAAAGGGCC |
| (Pubmed: NM_207338.3, | TAGCATCTGGGACGTCTTCACACACAGTGGGAAGGGG |
| bp: 133-1836) | AAAGTGCTTGGGAATGAGACGGCAGATGTAGCCTGTG |
|  | ACGGCTACTACAAGGTCCAGGAGGACATCATTCTGCTG |
|  | AGGGAACTGCACGTCAACCACTACCGATTCTCCCTGTC |
|  | TTGGCCCCGGCTCCTGCCCACAGGCATCCGAGCCGAGC |
|  | AGGTGAACAAGAAGGGAATCGAATTCTACAGTGATCT |
|  | TATCGATGCCCTTCTGAGCAGCAACATCACTCCCATCG |
|  | TGACCTTGCACCACTGGGATCTGCCACAGCTGCTCCAG |
|  | GTCAAATACGGTGGGTGGCAGAATGTGAGCATGGCCA |
|  | ACTACTTCAGAGACTACGCCAACCTGTGCTTTGAGGCC |
|  | TTTGGGGACCGTGTGAAGCACTGGATCACGTTCAGTGA |
|  | TCCTCGGGCAATGGCAGAAAAAGGCTATGAGACGGGC |
|  | CACCATGCGCCGGGCCTGAAGCTCCGCGGCACCGGCCT |
|  | GTACAAGGCAGCACACCACATCATTAAGGCCCACGCC |
|  | AAAGCCTGGCATTCTTATAACACCACGTGGCGCAGCAA |
|  | GCAGCAAGGTCTGGTGGGAATTTCATTGAACTGTGACT |
|  | GGGGGGAACCTGTGGACATTAGTAACCCCAAGGACCT |
|  | AGAGGCTGCCGAGAGATACCTACAGTTCTGTCTGGGCT |
|  | GGTTTGCCAACCCCATTTATGCCGGTGACTACCCCCAA |
|  | GTCATGAAGGACTACATTGGAAGAAAGAGTGCAGAGC |
|  | AAGGCCTGGAGATGTCGAGGTTACCGGTGTTCTCACTC |
|  | CAGGAGAAGAGCTACATTAAAGGCACATCCGATTTCTT |
|  | GGGATTAGGTCATTTTACTACTCGGTACATCACGGAAA |
|  | GGAACTACCCCTCCCGCCAGGGGCCCAGCTACCAGAA |
|  | CGATCGTGACTTGATAGAGCTGGTTGACCCAAACTGGC |
|  | CAGATCTGGGGTCTAAATGGCTATATTCTGTGCCATGG |
|  | GGATTTAGGAGGCTCCTTAACTTTGCTCAGACTCAATA |
|  | CGGTGATCCTCCCATATATGTGATGGAAAATGGAGCAT |
|  | CTCAAAAATTCCACTGTACTCAATTATGTGATGAGTGG |
|  | AGAATTCAATACCTTAAAGGATACATAAATGAAATGCT |
|  | AAAAGCTATAAAAGATGGTGCTAATATAAAGGGGTAT |
|  | ACTTCCTGGTCTCTGTTGGATAAGTTTGAATGGGAGAA |
|  | AGGATACTCAGATAGATATGGATTCTACTATGTTGAAT |
|  | TTAACGACAGAAATAAGCCTCGCTATCCAAAGGCTTCA |
|  | GTTCAATATTACAAGAAGATTATCATTGCCAATGGGTT |
|  | TCCCAATCCAAGAGAGGTGGAAAGTTGGTACCTCAAA |
|  | GCTTTGGAAACTTGCTCTATCAACAATCAGATGCTTGC |
|  | TGCAGAGCCCTTGCTAAGTCACATGCAAATGGTTACGG |
|  | AGATCGTGGTACCCACTGTCTGCTCCCTCTGTGTCCTCA |
|  | TCACTGCTGTTCTACTAATGCTCCTCCTGAGGAGGCAG |
|  | AGCTGA |

The invention therefore encompasses a modified MSC as described herein comprising a nucleic acid molecule selected from the group consisting of:

a) a nucleic acid molecule comprising a nucleotide sequence that encodes a Klotho protein, preferably according to a protein sequence of SEQ ID NO 6 to 10, whereby the nucleotide sequence is preferably a sequence according to SEQ ID NO 1, 2, 3, 4 or 5;

b) a nucleic acid molecule which is complementary to a nucleotide sequence in accordance with a);

c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 70%, 80%, preferably 90%, more preferably 95%;

d) a nucleic acid molecule which, as a consequence of the genetic code, is degenerated into a nucleotide sequence according to a) through c); and/or e) a nucleic acid molecule according to a nucleotide sequence of a) through d) which is modified by deletions, additions, substitutions, translocations, inversions and/or insertions and functionally analogous/ equivalent to a nucleotide sequence according to a) through d).

Functionally analogous sequences refer to the ability to encode a functional klotho gene product. Functionally analogous sequences refer to the ability to encode a functional Klotho gene product and to enable the same or similar functional effect as human Klotho. Klotho function may be determined by its β-glucuronidase activity, or via is functional effects described in the examples below. Appropriate assays for determining β-glucuronidase activity, or for assaying the desired biological functional effects described herein, and as shown in the examples, are known to a skilled person.

To measure the β-glucuronidase of Klotho, recombinant protein is subjected to an in vitro reaction. In this reaction the fluorescence-labeled substrate glucuronide is hydrolyzed by the Klotho protein. The reaction buffer contains 0.5 mM 4-methylumbelliferyl (4Mu)-D-glucuronide (Sigma), 0.1 M sodium citrate buffer, pH 5.5, 0.05M NaCl, 0.01% Tween 20, and 20 μg of purified secreted Klotho-protein. The reaction is carried out in a final volume of 100 μl. The enzymatic function of Klotho correlates with an increase in fluorescence intensity which is measured at several time points with a multi-label counter ARVOsx (PerkinElmer Life Sciences) at an excitation wavelength of 360 nm and an emission wavelength of 470 nm. Hydrolyzed products are quantified on the basis of 4-methylumbelliferone fluorescence.

The nucleotide sequence according to SEQ ID NO 1 to 5 encode a human Klotho protein of the amino acid sequences according to SEQ ID NO 6 to 10, which are preferred in the present invention:

TABLE 2

Preferred Klotho sequences.

| | |
|---|---|
| SEQ ID NO 6: Human Klotho full length (membrane-bound) amino acid sequence as encoded by SEQ ID 1 | MPASAPPRRPRPPPPSLSLLLVLLGLGGRRLRAEPGDGA QTWARFSRPPAPEAAGLFQGTFPDGFLWAVGSAAYQT EGGWQQHGKGASIWDTFTHHPLAPPGDSRNASLPLGA PSPLQPATGDVASDSYNNVFRDTEALRELGVTHYRFSIS WARVLPNGSAGVPNREGLRYYRRLLERLRELGVQPVV TLYHWDLPQRLQDAYGGWANRALADHFRDYAELCFR HFGGQVKYWITIDNPYVVAWHGYATGRLAPGIRGSPR LGYLVAHNLLLAHAKVWHLYNTSFRPTQGGQVSIALSS HWINPRRMTDHSIKECQKSLDFVLGWFAKPVFIDGDYP ESMKNNLSSILPDFTESEKKFIKGTADFFALCFGPTLSFQ LLDPHMKFRQLESPNLRQLLSWIDLEFNHPQIFIVENGW FVSGTTKRDDAKYMYYLKKFIMETLKAIKLDGVDVIG YTAWSLMDGFEWHRGYSIRRGLFYVDFLSQDKMLLPK SSALFYQKLIEKNGFPPLPENQPLEGTFPCDFAWGVVDN YIQVDTTLSQFTDLNVYLWDVHHSKRLIKVDGVVTKK RKSYCVDFAAIQPQIALLQEMHVTHFRFSLDWALILPLG NQSQVNHTILQYYRCMASELVRVNITPVVALWQPMAP NQGLPRLLARQGAWENPYTALAFAEYARLCFQELGHH VKLWITMNEPYTRNMTYSAGHNLLKAHALAWHVYNE KFRHAQNGKISIALQADWIEPACPFSQKDKEVAERVLEF DIGWLAEPIFGSGDYPWVMRDWLNQRNNFLLPYFTED EKKLIQGTFDFLALSHYTTILVDSEKEDPIKYNDYLEVQ EMTDITWLNSPSQVAVVPWGLRKVLNWLKFKYGDLP MYIISNGIDDGLHAEDDQLRVYYMQNYINEALKAHILD GINLCGYFAYSFNDRTAPRFGLYRYAADQFEPKASMKH YRKIIDSNGFPGPETLERFCPEEFTVCTECSFFHTRKSLL AFIAFLFFASIISLSLIFYYSKKGRRSYK |
| SEQ ID NO 7: Human Klotho full length (membrane-bound) amino acid sequence with additional HA-Tag (underlined text in the sequence) as encoded by SEQ ID NO 2. | MPASAPPRRPRPPPPSLSLLLVLLGLGGRRLRAEPGDGA QTWARFSRPPAPEAAGLFQGTFPDGFLWAVGSAAYQT EGGWQQHGKGASIWDTFTHHPLAPPGDSRNASLPLGA PSPLQPATGDVASDSYNNVFRDTEALRELGVTHYRFSIS WARVLPNGSAGVPNREGLRYYRRLLERLRELGVQPVV TLYHWDLPQRLQDAYGGWANRALADHFRDYAELCFR HFGGQVKYWITIDNPYVVAWHGYATGRLAPGIRGSPR LGYLVAHNLLLAHAKVWHLYNTSFRPTQGGQVSIALSS HWINPRRMTDHSIKECQKSLDFVLGWFAKPVFIDGDYP ESMKNNLSSILPDFTESEKKFIKGTADFFALCFGPTLSFQ LLDPHMKFRQLESPNLRQLLSWIDLEFNHPQIFIVENGW FVSGTTKRDDAKYMYYLKKFIMETLKAIKLDGVDVIG YTAWSLMDGFEWHRGYSIRRGLFYVDFLSQDKMLLPK SSALFYQKLIEKNGFPPLPENQPLEGTFPCDFAWGVVDN YIQVDTTLSQFTDLNVYLWDVHHSKRLIKVDGVVTKK RKSYCVDFAAIQPQIALLQEMHVTHFRFSLDWALILPLG NQSQVNHTILQYYRCMASELVRVNITPVVALWQPMAP NQGLPRLLARQGAWENPYTALAFAEYARLCFQELGHH VKLWITMNEPYTRNMTYSAGHNLLKAHALAWHVYNE KFRHAQNGKISIALQADWIEPACPFSQKDKEVAERVLEF DIGWLAEPIFGSGDYPWVMRDWLNQRNNFLLPYFTED EKKLIQGTFDFLALSHYTTILVDSEKEDPIKYNDYLEVQ EMTDITWLNSPSQVAVVPWGLRKVLNWLKFKYGDLP MYIISNGIDDGLHAEDDQLRVYYMQNYINEALKAHILD GINLCGYFAYSFNDRTAPRFGLYRYAADQFEPKASMKH YRKIIDSNGFPGPETLERFCPEEFTVCTECSFFHTRKSLL AFIAFLFFASIISLSLIFYYSKKGRRSYK<u>YPYDVPDYA</u> |
| SEQ ID NO 8: Human Klotho (secreted) amino acid sequence as encoded by SEQ ID NO 3 | MPASAPPRRPRPPPQSLSLLLVLLGLGGRRLRAEPGDGA QTWARFSRPPAPEAAGLFQGTFPDGFLWAVGSAAYQT EGGWQQHGKGASIWDTFTHHPLAPPGDSRNASLPLGA PSPLQPATGDVASDSYNNVFRDTEALRELGVTHYRFSIS WARVLPNGSAGVPNREGLRYYRRLLERLRELGVQPVV TLYHWDLPQRLQDAYGGWANRALADHFRDYAELCFR HFGGQVKYWITIDNPYVVAWHGYATGRLAPGIRGSPR LGYLVAHNLLLAHAKVWHLYNTSFRPTQGGQVSIALSS |

TABLE 2-continued

Preferred Klotho sequences.

|  |  |
|---|---|
|  | HWINPRRMTDHSIKECQKSLDFVLGWFAKPVFIDGDYP |
|  | ESMKNNLSSILPDFTESEKKFIKGTADFFALCFGPTLSFQ |
|  | LLDPHMKFRQLESPNLRQLLSWIDLEFNHPQIFIVENGW |
|  | FVSGTTKRDDAKYMYYLKKFIMETLKAIKLDGVDVIG |
|  | YTAWSLMDGFEWHRGYSIRRGLFYVDFLSQDKMLLPK |
|  | SSALFYQKLIEKNGFPPLPENQPLEGTFPCDFAWGVVDN |
|  | YIQVSQLTKPISSLTKPYH |
| SEQ ID NO 9: Human β-Klotho amino acid sequence as encoded by SEQ ID NO 4, | MKPGCAAGSPGNEWIFFSTDEITTRYRNTMSNGGLQRS VILSALILLRAVTGFSGDGRAMSKNPNFTPVNESQLFL YDTFPKNFFWGIGTGALQVEGSWKKDGKGPSIWDHFIH THLKNVSSTNGSSDSYIFLEKDLSALDFIGVSFYQFSISW PRLFPDGIVTVANAKGLQYYSTLLDALVLRNIEPIVTLY HWDLPLALQEKYGGWKNDTIIDIFNDYATYCFQMFGD RVKYWITIHNPYLVAWHGYGTGMHAPGEKGNLAAVY TVGHNLIKAHSKVWHNYNTHFRPHQKGWLSITLGSHW IEPNRSENTMDIFKCQQSMVSVLGWFANPIHGDGDYPE GMRKKLFSVLPIFSEAEKHEMRGTADFFAFSFGPNNFKP LNTMAKMGQNVSLNLREALNWIKLEYNNPRILIAENG WFTDSRVKTEDTTAIYMMKNFLSQVLQAIRLDEIRVFG YTAWSLLDGFEWQDAYTIRRGLFYVDFNSKQKERKPK SSAHYYKQIIRENGFSLKESTPDVQGQFPCDFSWGVTES VLKPESVASSPQFSDPHLYVWNATGNRLLHRVEGVRL KTRPAQCTDFVNIKKQLEMLARMKVTHYRFALDWASV LPTGNLSAVNRQALRYYRCVVSEGLKLGISAMVTLYYP THAHLGLPEPLLHADGWLNPSTAEAFQAYAGLCFQEL GDLVKLWITINEPNRLSDIYNRSGNDTYGAAHNLLVAH ALAWRLYDRQFRPSQRGAVSLSLHADWAEPANPYADS HWRAAERFLQFEIAWFAEPLFKTGDYPAAMREYIASKH RRGLSSSALPRLTEAERRLLKGTVDFCALNHFTTRFVM HEQLAGSRYDSDRDIQFLQDITRLSSPTRLAVIPWGVRK LLRWVRRNYGDMDIYITASGIDDQALEDDRLRKYYLG KYLQEVLKAYLIDKVRIKGYYAFKLAEEKSKPRFGFFTS DFKAKSSIQFYNKVISSRGFPFENSSSRCSQTQENTECTV CLFLVQKKPLIFLGCCFFSTLVLLLSIAIFQRQKRRKFWK AKNLQHIPLKKGKRVVS |
| SEQ ID NO 10: Human γ-Klotho Homo sapiens lactase like (LCTL), transcript variant 1, amino acid sequence as encoded by SEQ ID NO 5. | MKPVWVATLLWMLLLVPRLGAARKGSPEEASFYYGTF PLGFSWGVGSSAYQTEGAWDQDGKGPSIWDVFTHSGK GKVLGNETADVACDGYYKVQEDIILLRELHVNHYRFSL SWPRLLPTGIRAEQVNKKGIEFYSDLIDALLSSNITPIVTL HHWDLPQLLQVKYGGWQNVSMANYFRDYANLCFEAF GDRVKHWITFSDPRAMAEKGYETGHHAPGLKLRGTGL YKAAHHIIKAHAKAWHSYNTTWRSKQQGLVGISLNCD WGEPVDISNPKDLEAAERYLQFCLGWFANPIYAGDYPQ VMKDYIGRKSAEQGLEMSRLPVFSLQEKSYIKGTSDFL GLGHFTTRYITERNYPSRQGPSYQNDRDLIELVDPNWP DLGSKWLYSVPWGFRRLLNFAQTQYGDPPIYVMENGA SQKFHCTQLCDEWRIQYLKGYINEMLKAIKDGANIKGY TSWSLLDKFEWEKGYSDRYGFYYVEFNDRNKPRYPKA SVQYYKKIIIANGFPNPREVESWYLKALETCSINNQMLA AEPLLSHMQMVTEIVVPTVCSLCVLITAVLLMLLLRRQ S |

Protein modifications to the klotho protein, which may occur through substitutions in amino acid sequence, and nucleic acid sequences encoding such molecules, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. The substitution may not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function. In general, the non-polar amino acids Gly, Ala, Val, lie and Leu; the non-polar aromatic amino acids Phe, Trp and Tyr; the neutral polar amino acids Ser, Thr, Cys, Gin, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

In one embodiment the genetically modified cell as described herein are characterised in that said cell are obtained from bone marrow, umbilical cord, adipose tissue, or amniotic fluid.

In one embodiment the genetically modified cell as described herein are characterised in that said cell are CD34 negative.

In one embodiment the genetically modified cell as described herein are characterised in that said cell are human cell.

Due to their ability to migrate to areas of disease, in particular areas of inflammation, MSCs surprisingly represent a suitable tool for the delivery of Klotho as a therapeutic agent. Without being bound by theory, the MSCs of the present invention represent a drug delivery tool or vehicle for effective delivery of a therapeutic agent to the site of disease. According to a preferred embodiment of the present invention the therapeutic agent is Klotho protein expressed from an exogenous nucleic acid in said MSCs.

The cells of the present invention therefore enable beneficial and surprising therapeutic effects. Surprisingly, the administration of the MSCs described herein leads to effective migration to the site of disease after systemic, preferably intravenous, administration of the cells. The MSCs are capable of migration and potentially engraftment in areas of diseased tissue including tumors and other inflamed tissue. The MSCs themselves provide an anti-inflammatory signal beneficial to the disease conditions included in the invention, in addition to the enhanced local effect of Klotho from expression of the transgene present in the Klotho-modified MSCs.

The combination of MSCs exhibiting increased Klotho expression (compared to unmodified MSCs) with the treatment of a cancer, organ fibrosis, renal failure, age-related changes of organs or organ systems, arteriosclerosis, dementia, diabetes mellitus, neurodegenerative disease and autoimmune diseases and autoimmune-related diseases shows unexpected synergy. MSC homing to areas of diseased tissue, in addition to the anti-inflammatory properties of the MSCs themselves and the therapeutic effect of the Klotho transgene provides a synergistic therapeutic effect greater than the sum of each individual effect when considered in an isolated fashion.

The Klotho-modified MSCs thereby avoid and/or minimize potential side effects due to systemic administration of Klotho protein or Klotho-encoding nucleic acid vectors. The use of MSCs as vehicles for Klotho administration provides local production of Klotho in diseased regions of the body due to the homing capabilities of MSCs towards inflamed tissue.

Moreover MSCs are known to exhibit beneficial immunomodulatory effects on subjects and in particular on subjects that are inflicted with an inflammatory diseases and/or an unwanted immune response. It was particular surprising that the genetically modified MSCs maintain the beneficial immunomodulatory properties of MSCs. A person skilled in the art could not have suspected this, instead it would have been expected that the expression of Klotho, especially at therapeutically effective amounts, would interfere with the immunomodulatory properties of MSCs. However Klotho-MSCs maintain a beneficial modulatory function in particular on immune cells of the subject. Klotho-MSCs are therefore surprisingly effective for the treatment of diseases associated with unwanted inflammation and/or immune response. The expression of the therapeutically effective Klotho together with the immunomodulatory properties of the Klotho-MSCs yield to a synergistic therapeutic effect greater than the sum of the individual effects of both therapeutic agents when considered separately.

Moreover the Klotho-modified MSCs yield surprising therapeutic effects due to a continuous production of Klotho.

After administration the Klotho-modified MSCs may act as bio pump or drug factory that continuously provides Klotho protein to the subject. Thereby the amount of Klotho can be held at a therapeutic level over long periods. As stated herein, the homing capabilities of Klotho-MSCs advantageously lead to a localized expression of Klotho in diseased regions. However the expressed Klotho can also be transported by the vascular system throughout the body of the subject. Administered Klotho-MSCs therefore also contributes in a systemic manner largely irrespective of the location of the MSCs within the body of the subject. The continuous production of Klotho by the Klotho-MSCs is particularly advantageous as the Klotho protein may undergo degradation. Therefore a direct systematic administration of the Klotho protein to a subject would have to be carried out repeatedly at short intervals to maintain sufficient therapeutic levels. It is surprising that the genetically modified MSCs can overcome this obstacle by a continuous expression of Klotho over periods of more than 7, or more than 10 days and even more than 30 days. By acting as a bio pump the MSC-Klotho arrive at stable levels of Klotho within a subject for more than 1 week and even more than 1 month.

Particular stable levels of therapeutically effective Klotho result from expressing Klotho under the control of a constitutively active promotor. To this end the EFS, PGK and/or CMV promotor have proved particularly suited and allow for a prolonged expression at elevated levels.

Moreover, MSCs expressing Klotho proved to be very efficient in delivering the therapeutic protein into the vascular system of a patient. By means of the vascular system the Klotho proteins is transported throughout the body of the subject. Advantageously thereby therapeutic levels of Klotho can be established at different organs such as the liver, kidney and/or lung that may be inflicted by a disease. The administration of Klotho-MSCs is also effective for the treatment of neurodegenerative diseases that affect the brain. This is even the case if the Klotho-MSCs have not been introduced nor migrated towards the affected brain regions. It is therefore suspected that Klotho may advantageously pass the blood-brain barrier. Methods for the genetic modification of MSCs are known to those skilled in the art. Examples of suitable methods for genetic modification of MSCs are disclosed in WO 2010/119039 and WO 2008/150368.

In one embodiment the genetically modified mesenchymal stem cell as described herein is characterized in that the exogenous nucleic acid comprises a viral vector, for example in the form of a viral expression construct, more preferably a retroviral vector.

In one embodiment the genetically modified mesenchymal stem cell as described herein is characterized in that the exogenous nucleic acid is or comprises a non-viral expression construct.

In one embodiment the genetically modified mesenchymal stem cell as described herein is characterized in that the promoter or promoter/enhancer combination is a constitutive promoter. In another embodiment the genetically modified mesenchymal stem cell as described herein is characterised in that the promoter or promoter/enhancer combination is the CMV or EF2 promoter.

In a preferred embodiment the genetically modified mesenchymal stem cell as described herein is characterised in that the constitutive promoter is the EFS promoter.

In a preferred embodiment the genetically modified mesenchymal stem cell as described herein is characterised in that the constitutive promoter is the PGK promoter.

In a preferred embodiment the genetically modified mesenchymal stem cell as described herein is characterised in that the constitutive promoter is the EF1alpha promoter.

In one embodiment the genetically modified mesenchymal stem cell as described herein is characterised in that said promoter or promoter/enhancer combination is an inducible promoter.

In one embodiment the genetically modified mesenchymal stem cell as described herein is characterised in that the promoter is inducible upon differentiation of said cell post-administration.

In one embodiment the genetically modified mesenchymal stem cell as described herein is characterised in that the promoter is an inflammation-specific promoter, preferably wherein said promoter is induced by inflammatory mediators or cytokines and/or induced when the genetically modified mesenchymal stem cell comes into proximity with inflamed tissue.

The inducible forms of the promoter are designed to exhibit inflammation specific and/or localized expression of the Klotho protein. In combination with the homing and/or migratory properties of the MSCs, a synergistic effect is achieved, so that very little Klotho protein is expressed or produced in areas in the body of the subject distinct from the diseased tissue or organ.

In other embodiments, the expression of Klotho occurs in administered MSCs in a location distinct from the disease site and the protein is transported throughout the vascular system to the area of disease within the patient.

In one embodiment the genetically modified mesenchymal stem cell as described herein is characterised in that the promoter is the Tie2 promoter.

In one embodiment the genetically modified mesenchymal stem cell as described herein is characterised in that the promoter is the RANTES promoter.

In one embodiment the genetically modified mesenchymal stem cell as described herein is characterised in that the promoter is the HSP70 promoter.

It was surprising, in light of the prior art, that the expression of the inducible promoters mentioned herein led to sufficient expression of the therapeutic protein Klotho upon appropriate stimulus at the site of inflammation. The promoters provided herein show suitable inducible properties for quick and strong expression of Klotho upon entering into proximity with inflamed tissue.

In one embodiment the genetically modified mesenchymal stem cell as described herein is characterised in that said cell further comprises (iii) a selection marker gene operably linked to (iv) a constitutive promoter or promoter/enhancer combination.

In one embodiment the genetically modified cell as described herein is characterized in that the Klotho encoding region encodes a protein comprising or consisting of a sequence according to one of SEQ ID NO 6 to 10, wherein the Klotho encoding region preferably comprises or consists of a sequence according to SEQ ID NO 1 to 5.

In further embodiments the Klotho encoding region encodes a protein comprising or consisting of a sequence according to one of SEQ ID NO 6 to 10, or a sequence of at least 70% sequence identity, or at least 75%, 80%, 85%, 90% or 95% sequence identity, to one of SEQ ID NO 6 to 10, In one embodiment the genetically modified cell as described herein is characterized in that the Klotho encoding region encodes for a secreted form of the Klotho protein.

Advantageously the secreted form of Klotho is therapeutically particularly effective when expressed by mesenchymal stem cells.

In one embodiment the genetically modified cell as described herein is characterized in that the secreted form the Klotho protein comprises or consists of an amino acid sequence with an identity of at least 70%, preferably of at least 80%, 85%, 90% or at least 95% to SEQ ID NO 8. It is particularly preferred that the secreted Klotho protein has a sequence as laid out by SEQ ID No 8 or is functionally analogous to a protein with an amino acid sequence as laid out by SEQ ID NO 8.

In a further aspect the invention relates to the genetically modified mesenchymal stem cell as described herein for use as a medicament.

In one embodiment the genetically modified mesenchymal stem cell for use as a medicament as described herein is characterised in that said cell is administered by introducing a therapeutically effective number of cells into the bloodstream of a patient.

In one embodiment the genetically modified mesenchymal stem cell for use as a medicament as described herein is characterised by introducing a therapeutically effective number of said cells subcutaneously. It may further be preferably to this end the MSCs-Klotho are encapsulated by a biocompatible matrix and transplanted together with the matrix, preferably subcutaneously In one embodiment the invention relates to the genetically modified mesenchymal stem cell as described herein for use in cosmetic applications or plastic surgery, for example by introducing an effective number of said cells subcutaneously or intradermally to improve tautness or fairness of skin (reduction of wrinkles).

In one embodiment of the invention the genetically modified mesenchymal stem cell as described herein is intended for use in cosmetic applications or plastic surgery, such as by introducing an effective number of said cells subcutaneously or intradermally to augment skin volume (reduction of wrinkles).

In one embodiment of the invention the genetically modified mesenchymal stem cell as described herein is intended for use in treating hair loss by introducing an effective number of MSC-Klotho cells subcutaneously or intradermally.

In one embodiment the genetically modified mesenchymal stem cell for use as a medicament as described herein is characterised by introducing a therapeutically effective number of said cells to a subject within a biocompatible matrix.

Preferred materials for the biocompatible matrix are agarose, carrageenan, alginate, chitosan, gellan gum, hyaluronic acid, collagen, cellulose and its derivatives, gelatin, elastin, epoxy resin, photo cross-linkable resins, polyacrylamide, polyester, polystyrene and polyurethane or polyethylene glycol (PEG). It is further preferred that the biocompatible matrix is a semi-permeable hydrogel matrix and the Klotho-MSCs are entrapped by said matrix. Advantageously the biocompatible matrix allows for an efficient diffusion of nutrients, oxygens and other biomolecules to ensure a long lasting viability of the Klotho-MSCs, while immobilizing the cells. Thereby the Klotho-MSCs can be concentrated at preferred locations within the subject. For instance the Klotho-MSCs can be transplanted subcutaneously and/or in proximity of diseased regions of the subject i.e. the kidney for the treatment of renal diseases. It is surprising that by introducing encapsulated Klotho-MSCs, the cells function particularly efficiently as bio pumps and provide a high level of therapeutic Klotho to the subject. Firstly, the biocompatible matrix allows for the release of Klotho. Secondly, the elevated concentration of Klotho-MSCs within the microencapsulation promotes a feedback mechanism that results in the augmented production of Klotho in comparison to individually migrating Klotho-MSCs. The administration of microencapsulated Klotho-MSCs therefore constitutes a particular beneficial treatment of diseases that benefit from stable elevated levels of Klotho.

In one embodiment the genetically modified mesenchymal stem cell for use as a medicament as described herein is characterised in that the cell is administered intrathecally. To this end it is preferred that a therapeutically effective number of Klotho-MSCs are introduced into the spinal canal preferably into the subarachnoid space of subject. Thereby the Klotho-MSCs are capable of reaching the cerebrospinal fluid. Intrathecally administered Klotho-MSCs exhibit a surprisingly high viability and allow for a particular continuous provision of therapeutically effective Klotho protein to the brain region of a subject. It therefore preferred that the Klotho-MSCs are administered intrathecally for the treatment of neurodegenerative diseases. Most preferably the Klotho-MSCs are administered intrathecally for the treatment of Alzheimer's disease (AD), Multiple sclerosis (MS), Huntington's disease, Amyotrophic Lateral Sclerosis (ALS), Parkinson's disease, and/or Schizophrenia.

In one embodiment the genetically modified mesenchymal stem cell for use as a medicament as described herein is characterised in that is administered at least once per month, preferably at least once per week. The administration of Klotho-MSCs with the preferred periodicity proved to be well suited to maintain therapeutically effective levels of Klotho throughout the treatment of the subject.

Either isolated or repeated administration may lead to beneficial effects, whereby prolonged or continued administration, for example a long term administration, is also preferred. An example of such long term application is that the MSCs are administrated to the patient in multiple events, for example once per week or once per month, for at least two weeks, at least three weeks, at least four weeks, at least one month, at least two months, at least three months, at least four months, at least five months, at least six months, at least seven months, at least eight months, at least nine months, at least ten months, at least eleven months, at least one year, at least two years, or at least three years, or enduringly. Administration may, for example, be carried out as often as once per day, once per week, once every 7 to 14, or 7 to 21 days, or once per month, or once per two months, over a time period as mentioned above.

In a further aspect the invention relates to the genetically modified mesenchymal stem cell as described herein for use as a medicament in the treatment of disease.

In one embodiment the genetically modified mesenchymal stem cell for use as a medicament as described herein is characterised in that the disease is cancer.

In one embodiment the genetically modified mesenchymal stem cell for use as a medicament as described herein is characterised in that the disease is organ fibrosis.

In one embodiment the genetically modified mesenchymal stem cell for use as a medicament as described herein is characterised in that the disease is renal failure.

In one embodiment the genetically modified mesenchymal stem cell for use as a medicament as described herein is characterised in that the disease is associated with or caused by an age-related change in an organ or organ system physiology or function.

In one embodiment the genetically modified mesenchymal stem cell for use as a medicament as described herein is characterised in that the disease is or is associated with arteriosclerosis.

In one embodiment the genetically modified mesenchymal stem cell for use as a medicament as described herein is characterised in that the diseases is dementia.

In one embodiment the genetically modified mesenchymal stem cell for use as a medicament as described herein is characterised in that the disease is diabetes mellitus.

In one embodiment the genetically modified mesenchymal stem cell for use as a medicament as described herein is characterised in that the disease is an autoimmune disease.

In one embodiment the genetically modified mesenchymal stem cell for use as a medicament as described herein is characterised in that the disease is a lung disease.

In a further aspect the invention relates to the genetically modified mesenchymal stem cell as described herein for use as a medicament in the treatment of an inflammatory disorder.

In further embodiments the genetically modified mesenchymal stem cell for use as a medicament as described herein is characterised in that the inflammatory disease is vasculitis, nephritis, inflammatory bowel disease, rheumatoid arthritis and/or Graft versus Host disease.

In a further aspect the invention relates to the genetically modified mesenchymal stem cell as described herein for use as a medicament in the treatment of chronic fibrosis. In one embodiment the genetically modified mesenchymal stem cell for use as a medicament as described herein is characterised in that the inflammatory and/or chronic fibrotic disease is of the kidney, liver and/or colon of a subject. It was surprising that the localized expression of Klotho in fibrotic regions could lead to enhanced therapeutic effect. MSCs could show unexpected migratory properties towards fibrotic tissue and via expression of Klotho lead to a reduction in the formation of fibrotic tissue.

In one embodiment the genetically modified mesenchymal stem cell for use as a medicament as described herein is characterised in that said cell is administered by introducing a therapeutically effective number of said cells to the blood stream of a patient, thereby achieving delivery of Klotho protein expressed from said cells locally in regions of disease and/or inflammation. The administration of the MSCs of the present invention may also take place via routes of delivery including inhalation, endoscopic tissue injection, catheter-mediated tissue injection, cerebrospinal fluid injection, intraperitoneal injection, subcutaneous injection, intramuscular injection, optionally in combination with introduction of said cells into the bloodstream of a patient.

In one embodiment the genetically modified mesenchymal stem cell for use as a medicament as described herein is characterised in that the disease to be treated is a neurodegenerative disease.

In one embodiment of the invention the neurodegenerative disease is Alzheimer's disease (AD).

In one embodiment of the invention the neurodegenerative disease is Multiple sclerosis (MS).

In one embodiment of the invention the neurodegenerative disease is Huntington's disease.

In one embodiment of the invention the neurodegenerative disease is Amyotrophic Lateral Sclerosis (ALS).

In one embodiment of the invention the neurodegenerative disease is Parkinson's disease.

In one embodiment of the invention the neurodegenerative disease is Schizophrenia.

In a preferred embodiment the present invention is directed to the treatment of neurodegenerative disease via administration of the genetically modified cells described herein that comprise a Klotho transgene. Administration may be provided systemically, such as intravenously, due to the ability of MSCs to pass the blood-brain barrier. Alternative methods of administration, such as epidural injections or other modes of administration that do not require passage over the blood brain barrier are encompassed within the invention.

In particular the therapeutic approach is intended in early stage patients with neurodegenerative disease that has not progressed into severe or late stages of the disease.

Previous studies have described a sufficient safety profile with respect to the administration of MSCs to patients with MS or ALS. Immunomodulatory effects of the MSCs have also been described (Karussis et al., Arch Neurol. 2010 67(19), 1187). These beneficial effects could be enhanced by the use of a Klotho transgene in the MSCs described herein.

Additional indications exist, that Klotho may show therapeutic potential in treating neurodegenerative disease. Small molecule enhancers of Klotho function have been suggested to show therapeutic function in treating MS or other neurodegenerative diseases (Abraham et al., Future Med Chem, 2012 Sep. 4:13, 1671), klotho has been linked previously to myelination of the central nervous system (Chen et al., J Neurosci. 2013 January 33(5):1927) and reduced levels of klotho are found in Alzheimer's patients (Semba et al., Neurosci. Lett. 2014 January 13; 558: 37). Despite these suggestions the use of a Klotho transgene in MSCs for treatment of these medical conditions represents a surprising result considering the difficulties and low expectation of success in administering therapeutic transgenic products via cellular therapy. Surprisingly, locally delivered Klotho via transgene expression from a cellular MSC vehicle leads to a potential therapeutic effect against neurodegenerative disease, when said MSCs are administered either systemically (such as via i. v. injections), or locally (such as via epidural or cranial injection).

Various tests are available to the skilled person in order to assess neurodegenerative disease and are therefore also suitable to assess potential therapeutic effect of the klotho-MSCs described herein. For example, attention tests may be conducted, comprising pre-attentive tests, interrogating pre-pulse or inhibition, attention tests such as interrogating orientation, multiple choice responses, serial reaction tasks, go/no-go tests, or cognitive testing, including interrogating object discrimination, social transmission of food preference, transverse pattern tests, or learning and memory tests, such as associative tests, for example interrogating passive avoidance, one-way or two-way active avoidance, or spatial/contextual tests, comprising the radial arm maze, or morris water maze, or conditional emotional responses, such as testing for conditioned taste aversion, potentiated startle, or fear conditioning.

In a preferred embodiment the present invention is directed to the treatment of heart diseases and kidney disease via administration of the genetically modified cells described herein that comprise a Klotho transgene. These two groups of numerous medical indications are linked by the special feature of salt deposits, or calcification, in the arteries and veins of particular patients. Klotho is involved in phosphate metabolism, and thereby in the processing of salts in the body of mammalian subjects. In certain subjects, phosphate or calcium salts are not processed correctly and this leads to deposition of salts in the arteries and associated arterial, occlusive or cardiovascular disease. Such diseases may be characterized by "hardening" of the arteries.

One object of the invention is therefore the treatment of cardiovascular disease, circulatory disorders, arterial diseases and/or ischemic obstructive or occlusive conditions or strokes, preferably coronary heart diseases or peripheral arterial obstructive diseases, atherosclerosis and/or transplantation-induced sclerosis; a cerebral occlusive disease, or renal occlusive disease.

Surprisingly, subjects with kidney malfunction, in particular those in which the detection of creatine is not able to indicate the presence of said kidney malfunction, are at increased risk of suffering the heart or ischemic diseases described herein.

In one embodiment the present invention is directed to the treatment of sepsis via administration of the Klotho-modified MSCs as described herein.

In one embodiment the present invention is directed to the treatment of erectile dysfunction via administration of the Klotho-modified MSCs as described herein. Klotho is known to play a role in nitrogen monoxide (NO) regulation, thereby potentially influencing erectile function.

In one embodiment the genetically modified mesenchymal stem cell for use as a medicament are characterised in that the disease is an age-related change of organs or organ systems. In one embodiment the medical use of the MSCs described herein is directed to the treatment of ageing as such.

In one embodiment the genetically modified mesenchymal stem cell for use as a medicament are characterised in that the mesenchymal stem cells are used as a medicament to treat and/or prevent ageing or senescence. It is surprising that by administering Klotho-MSCs biological ageing processes can be effectively slowed, reversed and/or inhibited.

Klotho has been suspected to have positive anti-ageing properties. However the genetically modified MSCs that express Klotho exhibit a particularly effective anti-ageing function since the Klotho-MSCs target cells, tissues and/or organs of a subject inflicted by biological ageing. Thereby the Klotho-MSCs provide locally therapeutically effective dose of Klotho to ageing affected regions. Moreover Klotho-MSCs lead to the restoration and/or rejuvenation of the cell population of the subject and in particular of the stem cell population of the subject. The therapeutic effect of Klotho towards senescence augments to a surprising extent, when expressed by genetically modified MSCs.

In one embodiment the genetically modified mesenchymal stem cell for use as a medicament as described herein is characterised in that the subject is human.

In one embodiment the genetically modified mesenchymal stem cell for use as a medicament as described herein is characterised in that said genetically modified cells are allogeneic with respect to the subject.

In one embodiment the genetically modified mesenchymal stem cell for use as a medicament as described herein is characterised in that said genetically modified cells are autologous with respect to the subject.

In a further aspect of the invention the MSCs as described herein may comprise an exogenous nucleic acid encoding a chemokine ligand in combination with nucleic acid sequences suitable for expression of said ligand. Chemokine-encoding sequences may be either present in the same exogenous nucleic acid molecule that encodes Klotho or in a separate exogenous nucleic acid. Multiple integrated nucleic acid constructs or cassettes may be present in the MSCs of the present invention, each carrying one or more genes of interest, for example therapeutic genes, such as Klotho or other genes involved in mobilization of the cells, such as a chemokine. The invention therefore relates to the mesenchymal cells described herein, wherein the exogenous nucleic acid preferably encodes an inflammatory chemokine. Such chemokines are known to a skilled person. Examples of inflammatory chemokines relate to CXCL-8, CCL2, CCL3, CCL4, CCL5, CCL11 and CXCL10, CXCL1, CXCL2.

The invention further relates to a nucleic acid vector comprising a region encoding a Klotho protein, said region operably linked to a promoter or promoter/enhancer combination. In preferred embodiments the promoter or promoter/enhancer combination is one of those mentioned above.

The invention also relates to a method of delivering a Klotho protein to a cell, or to a subject in need thereof, for example in the context of a medical use of a Klotho protein, comprising administering the nucleic acid vector as described herein to a cell or subject, and/or administering a genetically modified MSC comprising the nucleic acid vector to a subject with one or more of the medical conditions disclosed herein The invention also relates to a method for the genetic transformation of an MSC, comprising the treatment of an MSC with a nucleic acid vector as disclosed herein encoding a Klotho protein.

DETAILED DESCRIPTION OF THE PREFERRED EMBODIMENT

All cited documents of the patent and non-patent literature are hereby incorporated by reference in their entirety.

The "mesenchymal cells" disclosed herein (also referred to in some embodiments as "mesenchymal stem cells" or "MSCs") can give rise to connective tissue, bone, cartilage, and cells in the circulatory and lymphatic systems. Mesenchymal stem cells are found in the mesenchyme, the part of the embryonic mesoderm that consists of loosely packed, fusiform or stellate unspecialized cells. As used herein, mesenchymal stem cells include, without limitation, CD34-negative stem cells.

In one embodiment of the invention, the mesenchymal cells are fibroblast-like plastic adherent cells, defined in some embodiments as multipotent mesenchymal stromal cells and also include CD34-negative cells.

For the avoidance of any doubt, the term mesenchymal cell encompasses multipotent mesenchymal stromal cells that also includes a subpopulation of mesenchymal cells, MSCs and their precursors, which subpopulation is made up of multipotent or pluripotent self-renewing cells capable of differentiation into multiple cell types in vivo.

As used herein, CD34-negative cell shall mean a cell lacking CD34, or expressing only negligible levels of CD34, on its surface. CD34-negative cells, and methods for isolating such cells, are described, for example, in Lange C. et al., "Accelerated and safe expansion of human mesenchymal stromal cells in animal serum-free medium for transplantation and regenerative medicine". J. Cell Physiol. 2007, Apr. 25.

Mesenchymal cells can be differentiated from hematopoietic stem cells (HSCs) by a number of indicators. For example, HSCs are known to float in culture and to not adhere to plastic surfaces. In contrast, mesenchymal cells adhere to plastic surfaces. The CD34-negative mesenchymal cells of the present invention are adherent in culture.

The genetically modified cell(s) described herein may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The present invention encompasses treatment of a patient by introducing a therapeutically effective number of cells into a subject's bloodstream. As used herein, "introducing" cells "into the subject's bloodstream" shall include, without limitation, introducing such cells into one of the subject's veins or arteries via injection. Such administering can also be performed, for example, once, a plurality of times, and/or over one or more extended periods. A single injection is preferred, but repeated injections over time (e.g., quarterly, half-yearly or yearly) may be necessary in some instances. Such administering is also preferably performed using an admixture of CD34-negative cells and a pharmaceutically acceptable carrier. Pharmaceutically acceptable carriers are well known to those skilled in the art and include, but are not limited to, 0.01-0.1 M and preferably 0.05 M phosphate buffer or 0.8% saline, as well as commonly used proprietary cryopreservation media.

Administration may also occur locally, for example by injection into an area of the subject's body in proximity to a tumor disease. MSCs have been shown to migrate towards cancerous tissue. Regardless, the local administration of the cells as described herein may lead to high levels of the cells at their site of action.

Additionally, such pharmaceutically acceptable carriers can be aqueous or non-aqueous solutions, suspensions, and emulsions, most preferably aqueous solutions. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in Remington: The Science and Practice of Pharmacy, 20th Ed., p. 808, Lippincott Williams S-Wilkins (2000). Preservatives and other additives may also be present, such as, for example, antimicrobials, antioxidants, chelating agents, inert gases, and the like.

As used herein, a "therapeutically effective number of cells" includes, without limitation, the following amounts and ranges of amounts: (i) from about $1\times10^2$ to about $1\times10^8$ cells/kg body weight; (ii) from about $1\times10^3$ to about $1\times10^7$ cells/kg body weight; (iii) from about $1\times10^4$ to about $1\times10^6$ cells/kg body weight; (iv) from about $1\times10^4$ to about $1\times10^5$ cells/kg body weight; (v) from about $1\times10^5$ to about $1\times10^6$ cells/kg body weight; (vi) from about $5\times10^4$ to about $0.5\times 10^5$ cells/kg body weight; (vii) about $1\times10^3$ cells/kg body weight; (viii) about $1\times10^4$ cells/kg body weight; (ix) about $5\times10^4$ cells/kg body weight; (x) about $1\times10^5$ cells/kg body weight; (xi) about $5 \times 10^5$ cells/kg body weight; (xii) about $1 \times 10^6$ cells/kg body weight; and (xiii) about $1 \times 10^7$ cells/kg body weight. Human body weights envisioned include, without limitation, about 5 kg, 10 kg, 15 kg, 30 kg, 50 kg, about 60 kg; about 70 kg; about 80 kg, about 90 kg; about 100 kg, about 120 kg and about 150 kg. These numbers are based on pre-clinical animal experiments and human trials and standard protocols from the transplantation of CD34+ hematopoietic stem cells. Mononuclear cells (including CD34+ cells) usually contain between 1:23000 to 1:300000 CD34-negative cells.

As used herein, "treating" a subject afflicted with a disorder shall mean slowing, stopping or reversing the disorder's progression. In the preferred embodiment, treating a subject afflicted with a disorder means reversing the disorder's progression, ideally to the point of eliminating the disorder itself. As used herein, ameliorating a disorder and treating a disorder are equivalent. The treatment of the present invention may also, or alternatively, relate to a prophylactic administration of said cells. Such a prophylactic administration may relate to the prevention of any given medical disorder, or the prevention of development of said disorder, whereby prevention or prophylaxis is not to be construed narrowly under all conditions as absolute prevention. Prevention or prophylaxis may also relate to a reduction of the risk of a subject developing any given medical condition, preferably in a subject at risk of said condition.

Typically, the term "inflammation" as used in its art-recognized sense relates to a localized or systemic protective response elicited by injury, infection or destruction of tissues which serves to protect the subject from an injurious agent and the injured tissue. Inflammation is preferably characterized by fenestration of the microvasculature, leakage of the elements of blood into the interstitial spaces, and migration of leukocytes into the inflamed tissue, which may lead to an uncontrolled sequence of pain, heat, redness, swelling, and loss of function.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

In some embodiments of the invention the MSCs as described herein migrate towards physiological niches affected by a disease condition, such as areas of inflammation, in order to impart their therapeutic effect, for example in a local manner.

As used herein "cell migration" is intended to mean movement of a cell towards a particular chemical or physical signal. Cells often migrate in response to specific external signals, including chemical signals and mechanical signals. Chemotaxis is one example of cell migration regarding response to a chemical stimulus. In vitro chemotaxis assays such as Boyden chamber assays may be used to determine whether cell migration occurs in any given cell. For example, the cells of interest may be purified and analyzed. Chemotaxis assays (for example according to Falk et al., 1980 J. Immuno. Methods 33:239-247) can be performed using plates where a particular chemical signal is positioned with respect to the cells of interest and the transmigrated cells then collected and analyzed. For example, Boyden chamber assays entail the use of chambers isolated by filters, used as tools for accurate determination of chemotactic behavior. The pioneer type of these chambers was constructed by Boyden (Boyden (1962) "The chemotactic effect of mixtures of antibody and antigen on polymorphonuclear leucocytes". J Exp Med 115 (3): 453). The motile cells are placed into the upper chamber, while fluid containing the test substance is filled into the lower one. The size of the motile cells to be investigated determines the pore size of the filter; it is essential to choose a diameter which allows active transmigration. For modelling in vivo conditions, several protocols prefer coverage of filter with molecules of extra-cellular matrix (collagen, elastin etc.) Efficiency of the measurements can be increased by development of multi-well chambers (e.g. NeuroProbe), where 24, 96, 384 samples are evaluated in parallel. Advantage of this variant is that several parallels are assayed in identical conditions.

Alternatively, tissue samples may be obtained from subjects (for example rodent models) after cell transplantation and assayed for the presence of the cells of interest in particular tissue types. Such assays may be of molecular nature, identifying cells based on nucleic acid sequence, or of histological nature, assessing cells on the basis of fluorescent markings after antibody labeling. Such assays are also particularly useful for assessing engraftment of transplanted cells. Assays for engraftment may also provide information on cell migration, as to some extent the engraftment is dependent on cell localization prior to engraftment.

In some embodiments of the invention the MSCs as described herein engraft in physiological niches affected by a disease condition, such as areas of inflammation, in order to impart their therapeutic effect, for example in a local manner.

As used herein "engraftment" relates to the process of incorporation of grafted or transplanted tissue or cells into the body of the host. Engraftment may also relate to the integration of transplanted cells into host tissue and their survival and under some conditions differentiation into non-stem cell states.

Techniques for assessing engraftment, and thereby to some extent both migration and the bio-distribution of MSCs, can encompass either in vivo or ex vivo methods. Examples of in vivo methods include bioluminescence, whereby cells are transduced to express luciferase and can then be imaged through their metabolism of luciferin resulting in light emission; fluorescence, whereby cells are either loaded with a fluorescent dye or transduced to express a fluorescent reporter which can then be imaged; radionuclide labeling, where cells are loaded with radionuclides and localized with scintigraphy, positron emission tomography (PET) or single photon emission computed tomography (SPECT); and magnetic resonance imaging (MRI), wherein cells loaded with paramagnetic compounds (e.g., iron oxide nanoparticles) are traced with an MRI scanner. Ex vivo methods to assess biodistribution include quantitative PCR, flow cytometry, and histological methods. Histological methods include tracking fluorescently labeled cells; in situ hybridization, for example, for Y-chromosomes and for human-specific ALU sequences; and histochemical staining for species-specific or genetically introduced proteins such as bacterial β-galactosidase. These immunohistochemical methods are useful for discerning engraftment location but necessitate the excision of tissue. For further review of these methods and their application see Kean et al., MSCs:

Delivery Routes and Engraftment, Cell-Targeting Strategies, and Immune Modulation, Stem Cells International, Volume 2013 (2013).

Progenitor or multipotent cells, such as the mesenchymal cells of the present invention, may therefore be described as protein delivery vehicles, essentially enabling the localization and expression of therapeutic gene products in particular tissues or regions of the subject's body. Such therapeutic cells offer the potential to provide cellular therapies for diseases that are refractory to other treatments. For each type of therapeutic cell the ultimate goal is the same: the cell should express a specific repertoire of genes, preferably exogenous nucleic acids that code for therapeutic gene products, thereby modifying cell identity to express said gene product and provide a therapeutic effect, such as an anti-inflammatory effect. The cells of the invention, when expanded in vitro, represent heterogeneous populations that include multiple generations of mesenchymal (stromal) cell progeny, which lack the expression of most differentiation markers like CD34. These populations may have retained a limited proliferation potential and responsiveness for terminal differentiation and maturation along mesenchymal and non-mesenchymal lineages.

As used herein the term "bio pump" or "drug factory" preferably describe the function of Klotho-MSCs as a continuously producing source of Klotho. By administering Klotho-MSCs to a subject particularly stable levels of Klotho can be provided. In the sense the bio pump, that is the Klotho-MSCs, allow for a continuous supply that maintains Klotho levels at a particular state, for example it may compensate for losses of Klotho for instance due to a degeneration of the protein.

As used herein "inducible expression" or "conditional expression" relates to a state, multiple states or system of gene expression, wherein the gene of interest, such as the therapeutic transgene, is preferably not expressed, or in some embodiments expressed at negligible or relatively low levels, unless there is the presence of one or more molecules (an inducer) or other set of conditions in the cell that allows for gene expression. Inducible promoters may relate to either naturally occurring promoters that are expressed at a relatively higher level under particular biological conditions, or to other synthetic promoters comprising any given inducible element. Inducible promoters may refer to those induced by particular tissue- or micro-environments or combinations of biological signals present in particular tissue- or micro-environments, or to promoters induced by external factors, for example by administration of a small drug molecule or other externally applied signal.

As used herein, in "proximity with" a tissue includes, for example, within 5 mm, within 1 mm of the tissue, within 0.5 mm of the tissue and within 0.25 mm of the tissue.

Given that stem cells can show a selective migration to different tissue microenvironments in normal as well as diseased settings, the use of tissue-specific promoters linked to the differentiation pathway initiated in the recruited stem cell is encompassed in the present invention and could in theory be used to drive the selective expression of therapeutic genes only within a defined biologic context. Stem cells that are recruited to other tissue niches, but do not undergo the same program of differentiation, should not express the therapeutic gene. This approach allows a significant degree of potential control for the selective expression of the therapeutic gene within a defined microenvironment and has been successfully applied to regulate therapeutic gene expression during neovascularization. Potential approaches to such gene modifications are disclosed in WO 2008/150368 and WO 2010/119039, which are hereby incorporated in their entirety.

As used herein, a "secreted" protein preferably refers to those proteins capable of being directed to the endoplasmic reticulum, the secretory vesicles, or the extracellular space as a result of a signal sequence, as well as those proteins released into the extracellular space without necessarily containing a signal sequence. If the secreted protein is released into the extracellular space, the secreted protein can undergo extracellular processing. The release into the extracellular space can preferably occur by many mechanisms, including exocytosis and proteolytic cleavage.

As used herein, "nucleic acid" shall mean any nucleic acid molecule, including, without limitation, DNA, RNA and hybrids or modified variants thereof. An "exogenous nucleic acid" or "exogenous genetic element" relates to any nucleic acid introduced into the cell, which is not a component of the cells "original" or "natural" genome. Exogenous nucleic acids may be integrated or non-integrated, or relate to stably transfected nucleic acids.

Any given gene delivery method is encompassed by the invention and preferably relates to viral or non-viral vectors, as well as biological or chemical methods of transfection. The methods can yield either stable or transient gene expression in the system used.

Genetically modified viruses have been widely applied for the delivery of genes into stem cells. Preferred viral vectors for genetic modification of the MSCs described herein relate to retroviral vectors, in particular to gamma retroviral vectors. The gamma retrovirus (sometimes referred to as mammalian type C retroviruses) is a sister genus to the lentivirus clade, and is a member of the Orthoretrovirinae subfamily of the retrovirus family. The Murine leukemia virus (MLV or MuLV), the Feline leukemia virus (FeLV), the Xenotropic murine leukemia virus-related virus (XMRV) and the Gibbon ape leukemia virus (GALV) are members of the gamma retrovirus genus. A skilled person is aware of the techniques required for utilization of gamma retroviruses in genetic modification of MSCs. For example, the vectors described Maetzig et al (Gammaretroviral vectors: biology, technology and application, 2001, Viruses June; 3(6):677-713) or similar vectors may be employed. For example, the Murine Leukemia Virus (MLV), a simple gammaretrovirus, can be converted into an efficient vehicle of genetic therapeutics in the context of creating gamma retrovirus-modified MSCs and expression of a therapeutic transgene from said MSCs after delivery to a subject.

Genetically modified viruses have been widely applied for the delivery of genes into stem cells. Adenoviruses may be applied, or RNA viruses such as Lentiviruses, or other retroviruses. Adenoviruses have been used to generate a series of vectors for gene transfer cellular engineering. The initial generation of adenovirus vectors were produced by deleting the E1 gene (required for viral replication) generating a vector with a 4 kb cloning capacity. An additional deletion of E3 (responsible for host immune response) allowed an 8 kb cloning capacity. Further generations have been produced encompassing E2 and/or E4 deletions. Lentiviruses are members of Retroviridae family of viruses (M. Scherr et al., Gene transfer into hematopoietic stem cells using lentiviral vectors. Curr Gene Ther. 2002 February; 2(1):45-55). Lentivirus vectors are generated by deletion of the entire viral sequence with the exception of the LTRs and cis acting packaging signals. The resultant vectors have a cloning capacity of about 8 kb. One distinguishing feature of these vectors from retroviral vectors is their ability to transduce dividing and non-dividing cells as well as terminally differentiated cells.

Non-viral methods may also be employed, such as alternative strategies that include conventional plasmid transfer and the application of targeted gene integration through the use of integrase or transposase technologies. These represent approaches for vector transformation that have the advantage of being both efficient, and often site-specific in their integration. Physical methods to introduce vectors into cells are known to a skilled person. One example relates to electroporation, which relies on the use of brief, high voltage electric pulses which create transient pores in the membrane by overcoming its capacitance. One advantage of this method is that it can be utilized for both stable and transient gene expression in most cell types. Alternative methods relate to the use of liposomes or protein transduction domains. Appropriate methods are known to a skilled person and are not intended as limiting embodiments of the present invention.

Cancer comprises a group of diseases that can affect any part of the body and is caused by abnormal cell growth and proliferation. These proliferating cells have the potential to invade the surrounding tissue and/or to spread to other parts of the body where they form metastasis. Worldwide, there were 14 million new cases of cancer and 8.2 million cancer related deaths in 2012 (World Cancer Report 2014). The majority of cancers is caused by environmental signals involving tobacco use, obesity and infections among others, while around 5-10% are genetic cases. Cancers can be classified into subcategories based on the cell of origin. The most common subcategories are carcinomas from epithelial cells, sarcomas from connective tissue and lymphomas and leukemias from hematopoietic cells. Cancer is associated with a high variety of local and systemic symptoms and cannot be cured in many cases. In light of the high number of new cancer patients and cancer related deaths novel treatment strategies are required.

Cancer according to the present invention refers to all types of cancer or neoplasm or malignant tumors found in mammals, including leukemias, sarcomas, melanomas and carcinomas. Examples of cancers are cancer of the breast, pancreas, colon, lung, non-small cell lung, ovary, and prostate.

Leukemias include, but are not limited to acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Sarcomas include, but are not limited to a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Melanomas include, but are not limited to include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

Carcinomas include, but are not limited to acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma exulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticurn, carcinoma telangiectodes, transitional cell carcinoma, carcinoma tuberosum, tuberous carcinoma, verrucous carcinoma, and carcinoma villosum.

Additional cancers include, but are not limited to Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, cervical cancer, endometrial cancer, adrenal cortical cancer, and prostate cancer.

Fibrosis is the endpoint of many chronic inflammatory diseases and is defined by an abnormal accumulation of extracellular matrix components. The term fibrosis designates the increase of fibrous connective tissue and material including collagen and other extracellular matrix proteins in the parenchyma of organs. This can occurs in multiple organs in response to external stimulation such as injury, infection, inflammation. Fibrosis can change the architecture and function of the affected tissue, which can interfere with organ function and therefore lead to pathology and even organ failure. Examples of Fibrosis include pulmonary fibrosis, liver cirrhosis, myocardial and renal fibrosis among others. New treatment options for this group of diseases are needed to improve the condition of affected patients.

Organ fibrosis according to the present invention refers to, but is not limited to, one or more of idiopathic pulmonary fibrosis, endomyocardial fibrosis, old myocardial infarction, atrial fibrosis, mediastinal fibrosis, myelofibrosis of the bone marrow, retroperitoneal fibrosis, progressive massive fibrosis of the lung, nephrogenic systemic fibrosis of the skin, crohn's disease, keloid, scleroderma/systemic sclerosis, arthrofibrosis, Peyronie's disease, Dupuytren's contracture, or adhesive capsulitis.

Despite its slow progression, it leads to organ malfunction. Fibrosis can affect almost any tissue. One of the main molecular agents inducing fibrosis is TGF-β1, mainly synthesized by T-cells during the healing process. TGF-β1 is secreted in a latent form associated with LAP (latency associated peptide). LAP is cleaved to allow the activation of TGF-β1 which is able to bind its receptors TGF-βR1 (transforming growth factor receptor-β1) and TGF-βR2. Therefore, there is a large pool of inactive TGF-β1 in the extracellular environment. Various agents can induce TGF-β1 activation: MMPs, reactive oxygen and nitrogen species (ROS and RNS), cytokines, or other stimuli such as ionizing radiation. The binding of TGF-β1 to its receptors activates the Smad (small mothers against decapentaplegic homolog) signaling pathway which induces the transcription of various genes, including genes encoding members of the extracellular matrix (collagens mostly). It also activates the differentiation of fibrocytes toward functional fibroblasts (Benoit et al., Breakthrough Stem Cells International 2014, Article ID 340257, 26 pages).

The term renal failure describes a medical condition in which the kidney is not functioning adequately to fulfil its physiological functions. The two main forms are chronic kidney disease and acute kidney injury. Acute kidney injury is defined by a rapid loss of renal function within less than 3 months. Chronic kidney disease is a progressive disease associated with gradual loss of renal function over a period of several months to years leading toward organ failure. It is estimated that in the US, 16.8% of adults aged 20 years and older were affected during 1999 to 2004. The 3 major causes of chronic kidney disease are diabetes, hypertension and glomerulonephritis. No specific treatment has been shown to slow down chronic kidney disease and late stage patients are treated with cost intensive renal replacement therapy involving dialysis and transplantation. Similarly, acute kidney injury often requires renal replacement therapy. Therefore, alternative treatment strategies to cure or slow down progression of acute kidney injury and chronic kidney disease are needed.

Renal failure according to the present invention refers to, but is not limited to, one or more of, acute kidney injury, chronic kidney disease, or acute-on-chronic renal failure.

In aging individuals, the function of almost every organ of the body is declining due to age-related changes also in the absence of pathology. These changes can be due to a variety of reasons including loss of organ specific cell function or organ specific cells. On the other hand, declining function of one organ can affect the function of other organs of the body. Age-related organ changes make older individuals less able to handle stress and external challenges such as physical activity, drug treatment, infections, and temperature changes, among many others. If the aging process of the various organ systems of the body could be slowed down this would increase the quality of life of aging people and would benefit society as a whole.

Age-related changes of organs and organ systems according to the present invention refers to, but is not limited to, one or more of age-related changes of bones, joints, ears, muscles, body fat, eyes, mouth, nose, skin, brain, nervous system, spinal cord, heart, blood vessels, lung, intestine, stomach, colon, esophagus, kidney, urinary tract, reproductive organs, breasts, endocrine system, bone marrow, and immune system.

The MSCs of the present invention may therefore be used as an anti-ageing agent, for example in the treatment of ageing, for example senescence-related ageing. "Senescence-related ageing" refers to senescence, meaning generally "to grow old", or "ageing". Biological aging is the process of accumulative changes to molecular and cellular structure that disrupts metabolism with the passage of time, resulting in deterioration and death. Senescence occurs both on the level of the whole organism (organismal senescence) as well as on the level of its individual cells (cellular senescence). The treatment of senescence (anti-ageing) is one aspect of the present invention. The treatment of ageing, or the treatment of senescence, relates in some embodiments to slowing, reversing and/or inhibiting the ageing process from occurring.

During aging the incidence of acute and chronic conditions such as neurological disorders, diabetes, degenerative arthritis, and even cancer rises within individuals, so that aging has been termed the substrate on which age-associated diseases grow. The invention therefore relates to prophylactic methods for preventing diseases associated with ageing.

The molecular pathways underlying aging are not well understood, as large individual heterogeneity of the biological aging process is observed. These inter-individual differences are proposed to derive from accumulation of stochastic damage that is counteracted by genetically encoded and environmentally regulated repair systems. At the level of molecules repair works by enzymatic systems while on the cellular level it works by replication and differentiation to maintain tissue homeostasis. However, the replicative potential of somatic and adult stem cells is limited by cellular senescence and recent evidence shows that counteracting senescence or removing senescent cells delays the onset of age-associated pathologies. The present invention therefore provides means for the treatment and/or prevention and/or reduction in risk of ageing as such, in addition to age-related medical conditions.

The term arteriosclerosis describes the pathological thickening, hardening and loss of elasticity of artery walls that can lead to stenosis and subsequent insufficient blood supply of downstream tissues resulting in ischemia. This process is often associated with calcification of the arterial wall. There are different types of arteriosclerosis that affect different anatomical locations and have different etiologies. Atherosclerosis is a specific type of arteriosclerosis, which is defined by the accumulation of white blood cells in the artery wall and formation of atheromatous plaques. Atherosclerosis is a chronic disease that can remain asymptomatic for extended periods until lumen stenosis of the affected artery occurs. Additionally, ruptures of atherosclerotic lesions can lead to thrombus formation and subsequent thromboembolism, which can lead to tissue necrosis/infarction in all parts of the body. Dramatic examples of such events are myocardial infarction and stroke, these aftereffects of atherosclerosis represent the most common cause of death in industrialized countries and therefore improved treatment strategies are urgently needed.

Arteriosclerosis according to the present invention refers to, but is not limited to, one or more of, atherosclerosis, arteriosclerosis obliterans, and Monckeberg's arteriosclerosis.

The terms circulatory disorders, cardiovascular disease, artery or blood vessel conditions and/or ischemic obstructive or occlusive diseases or conditions refer to states of vascular tissue where blood flow is, or can become, impaired or altered from normal levels. Many pathological conditions can lead to vascular diseases that are associated with alterations in the normal vascular condition of the affected tissues and/or systems. Examples of vascular conditions or vascular diseases to which the methods of the invention apply are those in which the vasculature of the affected tissue or system is senescent or otherwise altered in some way such that blood flow to the tissue or system is reduced or in danger of being reduced or increased above normal levels. It refers to any disorder in any of the various parts of the cardiovascular system, which consists of the heart and all of the blood vessels found throughout the body. Diseases of the heart may include coronary artery disease, CHD, cardiomyopathy, valvular heart disease, pericardial disease, congenital heart disease (e.g., coarctation, atrial or ventricular septal defects), and heart failure. Diseases of the blood vessels may include arteriosclerosis, atherosclerosis, hypertension, stroke, vascular dementia, aneurysm, peripheral arterial disease, intermittent claudication, vasculitis, venous incompetence, venous thrombosis, varicose veins, and lymphedema.

It was a surprising aspect of the present invention that the MSCs described herein localized in vivo to areas of atherosclerosis after systemic administration. The MSCs produced in a localized manner sufficient transgene to provide a therapeutic effect without unwanted systemic and uncontrolled expression of said transgene.

Neurodegenerative disease or neurodegeneration is a term for medical conditions in which the progressive loss of structure or function of neurons, including death of neurons, occurs. Many neurodegenerative diseases, including ALS, Parkinson's, Alzheimer's, and Huntington's, occur as a result of neurodegenerative processes. Such diseases are commonly considered to be incurable, resulting in progressive degeneration and/or death of neuron cells. A number of similarities are present in the features of these diseases, linking these diseases on a sub-cellular level. Some of the parallels between different neurodegenerative disorders include atypical protein assembly as well as induced cell death.

Dementia is a group of brain diseases causing a gradual decline of cognitive functions. Most of these diseases are chronic neurodegenerative diseases and are associated with neurobehavioral and/or neuropsychiatric symptoms that disable patients to independently perform activities of daily live. Alzheimer's disease is the most common form of dementia with 25 million affected individuals worldwide in the year 2000. This number is expected to increase to 114 million cases in 2050, unless preventive or neuroprotective therapy approaches emerge.

Dementia according to the present invention refers to, but is not limited to, one or more of, Alzheimer's disease, vascular dementia, post-stroke dementia, Lewy body dementia, frontotemporal dementia, Huntington's disease, and Creutzfeldt-Jakob disease.

Erectile dysfunction is a multifactorial disorder associated with aging and a range of organic and psychogenic conditions, including hypertension, hypercholesterolemia, diabetes mellitus, cardiovascular disease, and depression. Nitric oxide (NO) is believed to be an important vasoactive neurotransmitter and chemical mediator of penile erection. Impaired NO bioactivity is a pathogenic mechanism of erectile dysfunction. The efficacy of the PDE-5 inhibitors in the treatment of erectile dysfunction serves to illustrate the importance of the NO regulation in erectile function, since these agents counteract the degradation of NO-generated cGMP. However, not all patients respond to PDE-5 inhibitors, such that additional therapies are required (Burnett A L, J Clin Hypertens 2006 December; 8(12Suppl 4):53-62).

Diabetes mellitus is a group of chronic metabolic diseases that are associated with high blood sugar levels over prolonged periods, which can lead to severe complications including cardiovascular diseases, stroke, kidney failure, foot ulcers and damaged eyes. The two main subtypes are type 1 and type 2 diabetes mellitus. Type 1 diabetes mellitus is characterized by the loss of insulin-producing cells in the pancreas. It accounts for about 10% of the diabetes cases in the US and Europe, mostly affects children and is often associated with autoimmune pathologies. Type 2 diabetes mellitus is characterized by insulin resistance. Diabetes mellitus represents a massive health issue with more than 350 million affected people in 2013 worldwide.

Diabetes mellitus according to the present invention refers to, but is not limited to, one or more of, type 1 diabetes mellitus, type 2 diabetes mellitus, gestational diabetes, and latent autoimmune diabetes of adults.

Autoimmune diseases are a group a diseases that are caused by an abnormal immune response of the body against specific molecules or cells that are normally present in the body and should therefore be tolerated by the immune system under physiological conditions. The pathological reaction of the body's immune system against its own components can lead to severe physical conditions. A large number of diseases have been identified as being caused by autoimmune reactions and many pathologies of unclear etiology are suspected to have autoimmune components and are therefore termed autoimmune-related diseases. Therefore, the development of effective and specific treatment strategies for this group of diseases is urgently needed.

Autoimmune diseases and autoimmune-related diseases according to the present invention refers to, but is not limited to, one or more of, acute disseminated encephalomyelitis, acute necrotizing hemorrhagic leukoencephalitis, addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal & neuronal neuropathies, Balo disease, Behcet's disease, bullous pemphigoid, cardiomyopathy, Castleman disease, Celiac disease, chagas disease, chronic inflammatory demyelinating polyneuropathy, chronic recurrent multifocal ostomyelitis, Churg-Strauss syndrome, cicatricial pemphigoid/benign mucosal pemphigoid, Crohn's disease, Cogans syndrome, Cold agglutinin disease, Congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndromej, fibrosing alveolitis, giant cell arteritis, giant cell myocarditis, glomerulonephritis, Goodpasture's syndrome, granulomatosis with polyangiitis, Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura, IgA nephropathy, IgG4-related sclerosing disease, inclusion body myositis, interstitial cystitis, juvenile arthritis, juvenile diabetes (Type 1 diabetes), juvenile myositis, Kawasaki syndrome, Lambert-Eaton syndrome, leukocytoclastic vasculitis, Lichen planus, Lichen sclerosus, ligneous conjunctivitis, linear IgA disease (LAD), lupus (SLE), Lyme disease (chronic), Meniere's disease, microscopic polyangiitis, mixed connective tissue disease, mooren's ulcer, Mucha-Habermann disease, multiple sclerosis, myasthenia gravis, myositis, narcolepsy, neuromyelitis optica, neutropenia, ocular cicatricial pemphigoid, pptic neuritis, palindromic rheumatism, pediatric autoimmune neuropsychiatric disorders associated with streptococcus, paraneoplastic cerebellar degeneration, paroxysmal nocturnal hemoglobinuria, Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis. idiopathic pulmonary fibrosis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), susac's syndrome, sympathetic ophthalmia, Takayasu's arteritis, temporal arteritis/giant cell arteritis, thrombocytopenic purpura, Tolosa-Hunt syndrome, transverse myelitis, type 1 diabetes, ulcerative colitis, undifferentiated connective tissue disease, uveitis, vasculitis, vesiculobullous dermatosis, vitiligo, or Wegener's granulomatosis.

In preferred embodiments the lung disease is selected from an inflammatory or restrictive lung disease, a respiratory tract infection, a malignant or benign tumor of the lung and/or a pulmonary vascular disease or condition.

EXAMPLES

The invention is further described by the following examples. These are not intended to limit the scope of the invention. The experimental examples relate to the development of technology that enables Klotho expression from genetically modified MSCs. The examples further relate to trials in models suitable for testing the treatment of various medical conditions.

In preferred embodiments the examples relate to the preclinical development of a novel gene therapy product that combines the multiple beneficial effects of Klotho in the context of pathology with the immunomodulatory properties of primary human mesenchymal stem cells (MSCs) for the treatment of the above mentioned diseases.

Preparation of Human Mesenchymal Stem Cells:

Human cells are isolated from bone marrow by plastic adherence and are cultured in growth medium e.g. FBS containing DMEM as described by Pittinger, M. F. (2008) Mesenchymal stem cells from adult bone marrow, In D. J. Prockop, D. G. Phinney, B. A. Bunnell, Methods in Molecular Biology 449, Mesenchymal stem cells, Totowa: Humana Press). Mouse cells are isolated according to established methods. Methods for the isolation of MSCs from mice are known in the art, for example as described in Soleimani (Nat Protoc. 2009; 4(1):102-6) or Zhu (Nat Protoc. 2010; 5,550-560).

Generation of Vectors for the Expression of Klotho:

The transgene expression cassettes comprising a promoter and a coding region (e.g. cDNA) for human Klotho gene expression (full length or soluble form) are constructed using standard cloning techniques as described in Julia Lodge, Peter Lund, Steve Minchin (2007) Gene Cloning, Ney York: Tylor and Francis Group.

The promoters assessed during evaluation relate to the inducible promoters Tie2, RANTES or the HSP70 promoter, or the constitutive CMV or PGK promoters.

In some embodiments the gene is fused with tag-sequences (e.g. marker proteins/peptides like the hemagglutinin-tag or the HIS-tag) to allow easy detection of expression of the Klotho transgene (Hinrik Garoff, 1985, Annual Review of Cell Biology, Vol. 1:403-445). In particular, examples are described below having implemented the hemagglutinin-tagged version of Klotho for detection of Klotho expression.

In some examples the signal peptide of the Klotho gene is replaced by other Signal sequences. Furthermore, in some examples, gene sequences may be employed that are codon optimized to allow enhanced translation. The examples incorporating human Klotho employed sequences according to SEQ ID NO 2 or 3.

The transgene is then inserted into a suitable vector system (e.g. lentiviral or gamma-retroviral vector) by standard cloning techniques. A suitable vector is for example described by Baum (patent application EP 1757703 A2). The vector preferably comprises a second transgene cassette consisting of a promoter, an IRES sequence and a selectable marker gene (cell surface marker or resistance gene, for example the pac gene to confer puromycin resistance) to allow enrichment of genetically modified cells later in the process (David P. Clark, Nanette J. Pazdernik, 2009, Biotechnology: Applying the Genetic Revolution, London: Elsevier).

Genetic Modification of Mesenchymal Stem Cells:

The transduction is performed with modifications as described by Murray et al., 1999 Human Gene Therapy. 10(11): 1743-1752 and Davis et al., 2004 Biophysical Journal Volume 86 1234-1242. In detail: 6-well cell culture plates (e.g. Corning) are coated with Poly-L-Lysine (PLL) (e.g. Sigma-Aldrich, P4707-50ML): The PLL solution (0.01%) is diluted to final concentration between 0.0001% and 0.001% with PBS. 2 ml of the diluted PLL are used for each well. The plate is incubated at least for 2 h at room temperature. After incubation, the plates are washed carefully with PBS.

Viral vector supernatant in a final volume of 2 ml is added to each PLL-coated well. The number of particles should between $2 \times 10e3$ and $1 \times 10e6$ per well, which will result in multiplicity of infection of 0.25 and 10. The loaded plate is centrifuged for $2000 \times g$, 30 min, 4° C. Afterwards the supernatant is discarded and $1 \times 10e5$ mesenchymal stem cells are seeded per well. The plates are incubated at 37° with 5% CO2 for further use.

Analysis of Transgene Expression in MSC:

Flow Cytometry:

To demonstrate that the Klotho is expressed MSCs intracellular flow cytometry assays are performed. 3 days after transduction, MSC medium is exchanged with medium containing 1 μl BD Golgi Plug (Cat. No. 555029) per 1 ml Medium to enrich the expressed Klotho in the Golgi apparatus of the transduced cells.

Cells are incubated for 16 h at 37° C. and are then immunostained for the expression of the Klotho transgene. MSCs are harvested. The cells are permeabilized using the BD Cytofix/Cytoperm Cell Permeabilization/Fixation Solution (Becton Dickinson, 554722) according to the manufacturer's instructions to allow intracellular staining of the target Klotho protein.

A hemagglutinin-tag specific antibody labeled with Phycoerythrin (PE) (Milteny, 120-002-687) is used for detection of the expressed Klotho. $2 \times 10e5$ MSC are stained with 1000 of antibody (1:75 diluted with Perm/wash solution, Becton Dickinson, 554723).

Alternatively, antibodies directly directed against Klotho are used according to the instruction of the manufacturer (e.g. ProSci 45-810). The stained cells are washed and resuspended in PBS. The cells are then analyzed on an FC500 flow cytometer (Beckman Coulter).

ELISA to Determine Klotho Levels in the Supernatant:

Transduced MSC are seeded in 6 well plates ($1 \times 10e5$ MSC per well). Transduced MSC, which carry the pac puromycin resistance gene, are enriched by puromycin selection. Puromycin (3 μg/ml medium) is added to the medium and cells are cultivated over a period of 5 days at 37° C. and 5% CO2 with medium exchanges every 2 days to deplete non-transduced cells from the culture. Afterwards, puromycin-free medium is used for the culture. MSC are reseeded at a defined cell number of $1 \times 10e5$ cells per well in a 6 well-plate and are incubated for 72 h. Medium is collected and used for Klotho specific ELISA for quantification according to the manufacturer's instructions (e.g. R&D Systems DY5334-05).

Klotho-Expressed in MSC Protects the Cells from $H_2O_2$-Induced Apoptosis:

Imbalanced defense mechanisms against antioxidants, or overproduction or incorporation of free radicals, leads to neurodegeneration, by which neural cells suffer functional or sensory loss in neurodegenerative diseases. Oxidative stress (OS) leads to free radical attack on neural cells and contributes to neuro-degeneration; imbalanced metabolism and excess reactive oxygen species (ROS) generate a range of disorders such as Alzheimer's disease, Parkinson's disease, aging and many other neurodegenerative disorders (Uttara et al., Curr Neuropharmacol. 2009 March; 7(1):65-7). The ability of Klotho to protect cells from damage caused by reactive oxygen species represents a useful therapeutic model for the treatment of neurodegenerative disorders.

Oxidative stress markers are available in chronic kidney disease (CKD) patients and have confirmed the long held belief that CKD is a pro-oxidant state. Recent studies suggest that the link between oxidative stress and inflammation in CKD is emerging as a key process contributing to the pathogenesis of oxidative stress in these patients (Massy et al., Semin Dial. 2009 July-August; 22(4):405-8). The ability of Klotho to protect cells from damage caused by reactive oxygen species represents a useful therapeutic model for the treatment of chronic kidney disease.

Klotho is able to protect cells from the effects of reactive oxygen species:

Transduced and selected MSC (as described above) and non-transduced control MSC are seeded into 6-well plates (5000-50000 cells per $cm^2$). The cells are incubated 16 h at 37° C., 5° C. Transduced and non-transduced cells are subsequently treated with Hydrogen peroxide ($H_2O_2$, Roth, cat. No. 8070.2) for a period of 2-8 h. The final concentration of $H_2O_2$ in the culture is between 10-100 μM. In addition, selected samples of MSC are not treated with $H_2O_2$ and serve as control. All samples are trypsinated to detach the MSC from the plates.

The survival of MSC is determined by flow cytometry. The samples are subjected to the Dead Cell Apoptosis Kit (ThermoFisher Scientific, V13241) according to the manufacturer's instructions. The kit allows the detection of dead and apoptotic cells in the samples by staining with Annexin V Alexa Fluor 488 and Propidium Iodide (PI) (Vermes et al. (1995) Journal of Immunological Methods, Volume 184, Issue 1, Pages 39-51). The samples are analyzed by Flow cytometry. Klotho expressing MSC treated with $H_2O_2$ show increased survival and reduced apoptosis in comparison to native MSC treated with $H_2O_2$.

Klotho Secreted from Transduced MSC Protects HUVEC Cells from $H_2O_2$-Induced Apoptosis:

Klotho is able to protect cells from the effects of reactive oxygen species:

Transduced and selected MSC (as described previously) and non-transduced control MSC are seeded into 6-well plates (50000-200000 cells per $cm^2$). In addition, selected samples of MSC are not treated with $H_2O_2$ and serve as control. The cells are incubated 16-48 h at 37° C., 5° C. The supernatant is collected, filtered (0.25 μm) from the cells and stored.

Human umbilical vein endothelial cells (HUVEC) are seeded are seeded into 6-well plates (5000-50000 cells per $cm^2$). The cells are incubated for 16 h at 37° C. to let the cells attach to the plates. The cells are treated with Hydrogen peroxide ($H_2O_2$, Roth, cat. No. 8070.2). The final concentration of $H_2O_2$ in the culture is between 10-100 μM. Different dilutions of the Klotho containing supernatant and control supernatant is added to the HUVEC cells (2-4 ml volume). Samples are incubated for 2-8 h. All samples are trypsinated to detach the HUVEC cells from the plates.

The survival of HUVEC cells is determined by flow cytometry. The samples are subjected to the Dead Cell Apoptosis Kit (ThermoFisher Scientific, V13241) according to the manufacturer's instructions. The kit allows the detection of dead and apoptotic cells in the samples by staining with Annexin V Alexa Fluor 488 and Propidium Iodide (PI) (Vermes et al. (1995) Journal of Immunological Methods, Volume 184, Issue 1, Pages 39-51). The samples are analyzed by Flow cytometry. HUVEC cells treated with supernatant from Klotho-expressing MSCs show increased survival and reduced apoptosis in comparison to untreated HUVECs, when cultured in the presence of $H_2O_2$.

Klotho-Expressed in MSC Increases the Production of Nitric Oxide (NO) in the MSC:

The overall production of nitric oxide (NO) is decreased in chronic kidney disease (CKD) which contributes to cardiovascular events and further progression of kidney damage. Interventions that can restore NO production are likely to reduce the cardiovascular complications of CKD as well as slowing the rate of progression (Baylis, Am J Physiol Renal Physiol. 2008 January; 294(1):F1-9). The ability of Klotho to restore NO levels represents a useful therapeutic model for the treatment of kidney disease.

As discussed herein, nitric oxide (NO) is believed to be an important vasoactive neurotransmitter and chemical mediator of penile erection, whereby impaired NO bioactivity is a pathogenic mechanism of erectile dysfunction. The ability of Klotho to restore NO levels represents a useful therapeutic model for the treatment of erectile dysfunction.

Nitric oxide (NO) is an intercellular messenger that performs a number of functions, including neurotransmission, vasodilatation, inhibition of platelet aggregation, and modulation of leukocyte adhesion. NO has recently been shown to act as a potent cytotoxic effector molecule as well as to play an important role in the pathogenesis of organ-specific autoimmunity. NO may also modulate the immune response by interfering with Th1/Th2 balance in autoimmune diseases (Singh et al., Immunol Res. 2000; 22(1):1-19). The ability of Klotho to restore NO levels represents a useful therapeutic model for the treatment of autoimmune disease.

Klotho increases the production NO, an important intercellular messenger, in MSC:

Transduced and selected MSC (as described previously) and non-transduced control MSC are seeded into 6-well plates (5000-50000 cells per cm$^2$). The cells are incubated for 48 h at 37° C./5% $CO_2$.

To evaluate NO production, 100 μL of supernatant from each well of the culture plate is transferred to a new 96-well plate. The same amount of Griess reagent (1% sulfanil-amide, 0.1% naphthylenediamine dihydrochloride, and 2.5% phosphoric acid) is added to the supernatant. Nitrite concentrations in the supernatants are obtained by linear regression analysis of the standard curve by using serial double dilutions of sodium nitrite from 200 mmol/L to the 11th dilution. Absorbance is determined at 540 nm by using a microplate reader (Spectramax 190—Molecular Device, Sunnyvale, Calif). The concentration of NO is higher in samples collected from transduced MSC.

Klotho Secreted from Transduced MSC Induces Increased Nitric Oxide-Production in HUVEC Cells:

Transduced and selected MSC (as described previously) and non-transduced control MSC are seeded into 6-well plates (5000-50000 cells per cm$^2$). The cells are incubated for 48 h at 37° C./5% $CO_2$. The supernatant is collected, filtered (0.25 μm) from the cells and stored.

Human umbilical vein endothelial cells (HUVEC) are seeded are seeded into 6-well plates (5000-50000 cells per cm$^2$). The cells are incubated for 16 h at 37° C. to let the cells attach to the plates. Different dilutions of the Klotho containing supernatant and control supernatant is added to the HUVEC cells (2-4 ml volume). Samples are incubated for 6-48 h. To evaluate NO production, 100 μL of supernatant from each HUVEC well of the culture plate is transferred to a new 96-well plate. The same amount of Griess reagent (1% sulfanilamide, 0.1% naphthylenediamine dihydrochloride, and 2.5% phosphoric acid) is added to the supernatant. Nitrite concentrations in the supernatants are obtained by linear regression analysis of the standard curve by using serial double dilutions of sodium nitrite from 200 mmol/L to the 11th dilution. Absorbance is determined at 540 nm by using a microplate reader (Spectramax 190—Molecular Device, Sunnyvale, Calif). The concentration of NO is higher in HUVEC cells treated with supernatant from Klotho-expressing MSCs.

Klotho Secreted from Transduced MSC Suppress TGF-Beta Signaling in Target Cells

Transduced and selected MSC (as described previously) and non-transduced control MSC are seeded into 6-well plates (5000-50000 cells per cm$^2$). The cells are incubated for 48 h at 37° C./5% $CO_2$. The supernatant is collected, filtered (0.25 μm) from the cells and stored.

NRK52E renal epithelial cells are treated with the collected supernatants for 30 min and then stimulated with TGF-beta (10 ng/ml) for 30 min. The cells are lysed and used for immunoblot analysis. To detect activation of the TGF-beta signaling cascade in the renal cells, an antibody against phosphorylated Smad2 (pSmad2,) or antibody that recognized Smad2 regardless of its phosphorylation state (Smad2) is used. An increase in the fraction of phosphory-lated Smad2 in comparison to total Smad2 indicates activation of TGF-beta signaling. Klotho containing supernatant suppresses activation of TGF-beta signaling compared to cells that are treated with supernatants devoid of Klotho or untreated controls.

Klotho Secreted from Transduced MSC Increases FGF-23 Signaling in Target Cells

Transduced and selected MSC (as described previously) and non-transduced control MSC are seeded into 6-well plates (5000-50000 cells per cm$^2$). The cells are incubated for 48 h at 37° C./5% $CO_2$. The supernatant is collected, filtered (0.25 μm) from the cells and stored.

293 cells, which express the FGF-receptor, are seeded in 6 well plates (5000 cells per cm$^2$) and incubated overnight. Medium is exchanged for Klotho-containing or Klotho-free supernatant and the cells are incubated for 30 min. Afterward mouse FGF23 (R179Q) (10 ng/ml) is added and the cells are incubated for an additional 15 min. Cells are harvested and lysed using lysis buffer (M PER Mammalian Protein Extraction Reagent) containing inhibitors for phosphatase and proteinase (Halt Protease Inhibitor Cocktail, EDTA Free(100×)). FGF signaling is determined by immunoblot analysis using anti-phospho-FRS2a antibody (p-FRS2a), anti-phospho-ERK1/2 antibody (p-ERK1/2), or anti-ERK1/2 antibody (ERK1). Klotho containing supernatant activates FGF23 signaling compared to cells that are treated with supernatants devoid of Klotho or untreated controls.

Studies in Animal Models for Interrogating Klotho Function when Expressed from Transgenic MSCs:

The experiments described herein are based on the occurrence that old mice lack klotho in the kidney, and that Klotho deficiency in old mice can be restored by i.v. application of Klotho-modified MSCs. In murine models mouse MSCs were employed, obtained by methods as described above, and the mouse Klotho sequence was used. Klotho-modified MSCs improve renal function, improve heart rate variability and prolong lifespan in old mice.

Experimental Approach:

Mice at the age of 12-15 months are obtained from Jackson Laboratories. All animals are placed in metabolic cages once a week to measure renal function. After sacrifice, klotho expression in the kidney will determined by immunohistology.

Two different Experiments are conducted in 6 groups.

Experiment A:

Group 1: Mice age 12-15 months are placed in metabolic cages once a week. No further treatment will be performed until they die.

Group 2: Mice age 12-15 months are treated with non-transduced MSCs (Mesenchymal stem cells having been obtained from young donor animals, age 6 weeks). They receive $1 \times 10^6$ MSCs once a month until death. All animals are placed in metabolic cages once a week.

Group 3: Mice age 12-15 months are treated with Klotho-modified MSCs (Mesenchymal stem cells having been obtained from young donor animals, age 6 weeks, are genetically modified according to the protocols described herein to express transgenic klotho). They receive $1 \times 10^6$ Klotho-modified MSCs once a month until death. All animals are placed in metabolic cages once a week.

Results: Animals in group 3 show significant improved renal function and live significantly longer in comparison to animals in group 1 and 2. Klotho expression in the kidney is significantly higher in animals in group 3 than in the other two groups.

Experiment B:

Group 1: Mice age 12-15 months are implanted with an ETA-F10 transmitter (DSI, St. Paul, MN, USA). Once a week ECG and heart rate variability are measured.

Group 2: Mice age 12-15 months are implanted with an ETA-F10 transmitter (DSI, St. Paul, MN, USA). All animals are treated with non-transduced MSCs (Mesenchymal stem cells having been obtained from young donor animals, age 6 weeks). Treated mice receive $1 \times 10^6$ MSCs once a month until death. Once a week ECG and heart rate variability are measured.

Group 3: Mice age 12-15 months are implanted with an ETA-F10 transmitter (DSI, St. Paul, MN, USA). All animals are treated with Klotho-modified MSCs (Mesenchymal stem cells having been obtained from young donor animals, age 6 weeks, are genetically modified to express klotho as described herein). Treated mice receive $1 \times 10^6$ Klotho-modified MSCs once a month. Once a week ECG and heart rate variability are measured.

Results: Animals in group 3 show significant improved heart rate variability in comparison to animals of group 1 and 2.

MSC Expressing Klotho Improve Kidney Fibrosis in an Murine Model

To induce kidney fibrosis 129S1/SvImJ mice (7-10 weeks of age) are used. The right ureter is surgically exposed and ligated (unilateral ureteral obstruction, UUO). After surgery, mice are injected intravenously or intraperitoneally with Klotho-expressing MSC ($5 \times 10^5$-$2 \times 10^6$ cells per mouse) or with PBS. The treatment is repeated every 3 days.

After 14 days post-surgery mice are sacrificed and the kidney is prepared for histology. Markers of renal fibrosis, such as the number of interstitial fibroblasts, interstitial volume, expression for collagen I are all increased in UUO animals treated with PBS only. In contrast, UUO animals that receive Klotho-expressing MSC show markedly decreased levels of renal fibrosis.

Studies in Animal Models for Interrogating Klotho Function when Expressed from Transgenic MSCs in Alzheimer's Disease (AD):

The following examples describe approaches that demonstrate that intravenous or intrathecally administered MSC-Klotho induce maturation of oligodendrocytic progenitor cells (OPCs), intravenous or intrathecally administered MSC-Klotho increases the number of total oligodendro-cytes, intravenous or intrathecally administered MSC-Klotho improve myelination of oligodendrocytes, intravenous or intrathecally administered MSC-Klotho reduces plaques in a mouse model of APPswe/PS1(M146V) double transgenic mice, intravenous or intrathecally administered MSC-Klotho restores cognition in a mouse model of APPswe/PS1(M146V) double transgenic mice, intravenous or intrathecally administered MSC-Klotho induce behavioral recovery by elevating brain-derived neurotrophic factor (BDNF), neurotrophin-3 (NT-3) and vascular endothelial growth factor (VEGF) levels in the brains of APPswe/PS1 (M146V) double transgenic mice, and that intravenous or intrathecally administered MSC-Klotho promote activation of microglia that secrete neurotrophic agents and results in cognitive improvements and a reduction in Aβ pathology in APPswe/PS1(M146V) double transgenic mice.

Experimental Setup

Three different mouse strains (C3B6-Tg(APP695)3Dbo/Mmjax, C3B6-Tg(APP695)3Dbo/Mmjax, B6;129-Psen1tm1Mpm Tg(APPSwe,tauP301L)1Lfa/Mmjax) resembling Alzheimer's disease are employed.

Three different Experiments will be conducted in 18 groups.

Experiment A:

Mesenchymal stem cells from young donor animals, age 6 weeks, are genetically modified to express klotho. $1 \times 10^6$ MSC-Klotho are injected intravenously once a month.

Group 1 C3B6-Tg(APP695)3Dbo/Mmjax mice

Group 2 C3B6-Tg(APP695)3Dbo/Mmjax mice

Group 3 B6;129-Psen1tm1Mpm Tg(APPSwe,tauP301L) 1Lfa/Mmjax mice

Mice are injected with saline intravenously once a month.

Group 4 C3B6-Tg(APP695)3Dbo/Mmjax mice

Group 5 C3B6-Tg(APP695)3Dbo/Mmjax mice

Group 6 B6;129-Psen1tm1Mpm Tg(APPSwe,tauP301L) 1Lfa/Mmjax mice $1 \times 10^6$ of non-transduced mesenchymal stem cells from young donor animals (age 6 weeks) are injected intravenously into the mice once a month.

Group 7 C3B6-Tg(APP695)3Dbo/Mmjax mice

Group 8 C3B6-Tg(APP695)3Dbo/Mmjax mice

Group 9 B6;129-Psen1tm1Mpm Tg(APPSwe,tauP301L) 1Lfa/Mmjax mice

Cognitive tests are performed once a week over a 3 month period.

Results: Animals in groups 1-3 show significant improvement of attention, learning and memory compared with animals in groups 4-6 and groups 7-9.

Experiment B:

Mesenchymal stem cells from young donor animals, age 6 weeks, are genetically modified to express klotho. $1 \times 10^6$ MSC-Klotho are injected intrathecally once a month.

Group 1 C3B6-Tg(APP695)3Dbo/Mmjax mice

Group 2 C3B6-Tg(APP695)3Dbo/Mmjax mice

Group 3 B6;129-Psen1tm1Mpm Tg(APPSwe,tauP301L) 1Lfa/Mmjax mice

Mice are injected with saline intrathecally once a month

Group 4 C3B6-Tg(APP695)3Dbo/Mmjax mice

Group 5 C3B6-Tg(APP695)3Dbo/Mmjax mice

Group 6 B6;129-Psen1tm1Mpm Tg(APPSwe,tauP301L) 1Lfa/Mmjax mice $1 \times 10^6$ of non-transduced mesenchymal stem cells from young donor animals (age 6 weeks) are injected intravenously into the mice once a month.

Group 7 C3B6-Tg(APP695)3Dbo/Mmjax mice

Group 8 C3B6-Tg(APP695)3Dbo/Mmjax mice

Group 9 B6;129-Psen1tm1Mpm Tg(APPSwe,tauP301L) 1Lfa/Mmjax mice

Three animals of each group will be sacrificed every week for 3 months. Immunohistochemistry, electron microscopy, HPLC, qRT-PCR and western blotting of brain tissue will be performed.

Results: Animals in groups 1-3 show significant improvement in maturation of oligodendrocytic progenitor cells (OPCs), increased number of total oligodendrocytes, improved myelination of oligodendrocytes, reduced Aβ plaques, elevation of brain-derived neurotrophic factor (BDNF), neurotrophin-3 (NT-3) and vascular endothelial growth factor (VEGF) levels, compared with animals in groups 4-6 and groups 7-9.

Studies in Animal Models for Interrogating Klotho Function when Expressed from Transgenic MSCs in Multiple Sclerosis (MS):

The following examples describe approaches that demonstrate that intravenous or intrathecally administered MSC-Klotho induce maturation of oligodendrocytic progenitor cells (OPCs), intravenous or intrathecally administered MSC-Klotho increases the number of total oligodendrocytes, intravenous or intrathecally administered MSC-Klotho improve myelination of oligodendrocytes, intravenous or intrathecally administered MSC-Klotho reduce inflammation, and that intravenous or intrathecally administered MSC-Klotho reduce number of activated T- and B-cells in the brain of MS patients.

Experimental Setup:

A mouse model of autoimmune encephalomyelitis (EAE) is used. C57BL/6 (H-2b) mice are immunized with myelin oligodendrocyte protein ($MOG_{35-55}$).

Two different Experiments are conducted in 6 groups

Experiment A:

Mesenchymal stem cells from young donor animals, age 6 weeks, are genetically modified to express klotho. $1 \times 10^6$ MSC-Klotho are injected intravenously once a week.

Group 1 C57BL/6 (H-2b) immunized with ($MOG_{35-55}$)

Mice are injected with saline intravenously once a week

Group 2 C57BL/6 (H-2b) immunized with ($MOG_{35-55}$)

$1 \times 10^6$ of non-transduced mesenchymal stem cells from young donor animals (age 6 weeks) are injected intravenously into the mice once a month.

Group 3 C57BL/6 (H-2b) immunized with ($MOG_{35-55}$)

Experiment B:

Mesenchymal stem cells from young donor animals, age 6 weeks, are genetically modified to express klotho. $1 \times 10^6$ MSC-Klotho are injected intrathecally once a week.

Group 4 C57BL/6 (H-2b) immunized with ($MOG_{35-55}$)

Mice are injected with saline intrathecally once a week.

Group 5 C57BL/6 (H-2b) immunized with ($MOG_{35-55}$)

$1 \times 10^6$ of non-transduced mesenchymal stem cells from young donor animals (age 6 weeks) are injected intrathecally into the mice once a month.

Group 6 C57BL/6 (H-2b) immunized with ($MOG_{35-55}$)

All animals in groups 1-6 are followed daily for paralysis beginning in the tail and hind limbs and progressing to the fore-limbs concurrent with weight loss. Once a week 3 animals from each group are sacrificed and immunohistochemistry, electron microscopy, HPLC, qRT-PCR and western blotting of brain tissue is performed.

Studies in Animal Models for Interrogating Klotho Function when Expressed from Transgenic MSCs in Amyotrophic Lateral Sclerosis (ALS):

The following examples describe approaches that demonstrate that intravenous or intrathecally administered MSC-Klotho induce maturation of oligodendrocytic progenitor cells (OPCs), intravenous or intrathecally administered MSC-Klotho increases the number of total oligodendrocytes, intravenous or intrathecally administered MSC-Klotho improve myelination of oligodendrocytes, intravenous or intrathecally administered MSC-Klotho reduce axon degeneration, intravenous or intrathecally administered MSC-Klotho will inhibit Wnt signaling.

Experimental Setup:

SOD1 (G93A) mice are utilized. Two different Experiments will be conducted in 6 groups Experiment A:

Mesenchymal stem cells from young donor animals, age 6 weeks, are genetically modified to express klotho. $1 \times 10^6$ MSC-Klotho are injected intravenously once a week.

Group 1 SOD1 (G93A)

Mice are injected with saline intravenously once a week

Group 2 SOD1 (G93A)

$1 \times 10^6$ of non-transduced mesenchymal stem cells from young donor animals (age 6 weeks) are injected intravenously into the mice once a month.

Group 3 SOD1 (G93A)

Experiment B:

Mesenchymal stem cells from young donor animals, age 6 weeks, are genetically modified to express klotho. $1 \times 10^6$ MSC-Klotho are injected intrathecally once a week.

Group 4 SOD1 (G93A)

Mice are injected with saline intrathecally once a week

Group 5 SOD1 (G93A)

$1 \times 10^6$ of non-transduced mesenchymal stem cells from young donor animals (age 6 weeks) are injected intrathecally into the mice once a month.

Group 6 SOD1 (G93A)

Once a week 3 animals from each group are sacrificed and brain and spinal cord will be harvested. Immunohistochemistry, electron microscopy, HPLC, qRT-PCR and western blotting of brain and spinal cord are performed.

Studies in Animal Models for Interrogating Klotho Function when Expressed from Transgenic MSCs in Diabetes Type 1

The following examples describe approaches that demonstrate that intravenous administered MSC-Klotho delay the onset of diabetes type 1 in mice.

Experimental Setup:

To assess the effect of Klotho-MSCs on the development of diabetes in vivo, a mouse model of cyclophosphamide-accelerated type 1 diabetes is performed (adapted from Brode et al., The Journal of Immunology 2006). NOD mice are obtained, where the incidence of diabetes in female mice is 75% by 40 weeks of age. To accelerate and synchronize diabetes, female 8-week-old NOD mice are treated with a single i.p. injection of cyclophosphamide (CY) (200 mg/kg body weight in 0.9% normal saline). Mice are then randomly divided into treatment and control groups.

One to five days after cyclophosphamide treatment each animal receives 200 µL of PBS by tail vain or intraperitoneal injection. Mice are monitored weekly for hyperglycemia until they become diabetic, as defined by two consecutive (>24 hr apart) non-fasting blood glucose levels >240 mg/dl.

Group 1 NOD after Cyclophosphamide Treatment

One to five days after cyclophosphamide treatment animal receives 200 µL of $1 \times 10^6$ MSCs (from young donor animals, age 6 weeks) in 200 µL PBS by tail vain or intraperitoneal injection. Mice are monitored weekly for hyperglycemia until they become diabetic, as defined by two consecutive (>24 hr apart) non-fasting blood glucose levels >240 mg/dl.

Group 2 NOD after Cyclophosphamide Treatment

Mesenchymal stem cells from young donor animals, age 6 weeks, are genetically modified to express Klotho. One to five days after cyclophosphamide treatment animal receives $1 \times 10^6$ Klotho-MSCs in 200 µL PBS by tail vain or intraperitoneal injection. Mice are monitored weekly for hyperglycemia until they become diabetic, as defined by two consecutive (>24 hr apart) non-fasting blood glucose levels >240 mg/dl.

Group 3 NOD after Cyclophosphamide Treatment

Mice of group 1 develop diabetes within 30 days, whereas the onset of diabetes in mice treated with either MSCs (group 2) or Klotho-MSCs (group 3) is delayed. Interestingly, for mice of group 3, the delay in development of diabetes is increased by 2 weeks compared to group 2.

Studies in Animal Models for Interrogating Klotho Function when Expressed from Transgenic MSCs in Diabetes Type 2

The following examples describe approaches that demonstrate that intravenous administered MSC-Klotho will improve glucose metabolism diabetes type 2 in mice. A similar model is described in Chen et al. (J Diabetes Research, 2015, Art ID 796912).

Experimental Setup:

C57BL/6 mice are fed standard (SD) or high fat (HFD) diet. After 4 weeks mice are divided into 6 groups Group 1: Mice fed with SD receive saline intravenously once a week for 8 weeks Group 2: Mice fed with HFD receive saline intravenously once a week for 8 weeks Group 3: Mice fed with SD receive $1 \times 10^6$ MSC once a week for 8 weeks Group 4: Mice fed with HFD receive $1 \times 10^6$ MSC once a week for 8 weeks Group 5: Mice fed with SD receive $1 \times 10^6$ MSC-Klotho once a week for 8 weeks Group 6: Mice fed with HFD receive $1 \times 10^6$ MSC-Klotho once a week for 8 weeks Mice in groups 4 and 6 show improved glucose metabolism (hyperglycemia, hyperinsulinemia body weight and/or beta cell mass) compared with mice in group 2.

Klotho-MSCs (group 6) show further improved glucose metabolism compared with mice treated with non-transduced MSCs (group 4).

Studies in Animal Models for Interrogating Klotho Function when Expressed from Transgenic MSCs in Chronic Renal Failure C57/BL6 mice age 10 weeks are uninephrectomized and receive a subcutaneous implantation of a 50 mg doxycorticosterone acetate (DOCA) pellet. 7 days later mice are implanted subcutaneous with an osmotic mini pump delivering 1.5 ng angiotensin II per minute and per gram body weight for 2 weeks. A similar model is described in Kirchhoff et al (Kidney International, 2008, 73, 643).

During the 4 following weeks mice receive either saline intravenously or MSC intravenously or MSC-Klotho intravenously once a week for 4 weeks. Blood pressure, albuminuria and serum creatinine are monitored once a week.

Group 1:
C57/BL6 with DOCA and angiotensin II receive intravenous saline for 4 weeks.

Group 2:
C57/BL6 with DOCA and angiotensin II receive intravenous $1 \times 10^6$ MSC once a week for 4 weeks.

Group 3:
C57/BL6 with DOCA and angiotensin II will receive intravenous $1 \times 10^6$ MSC-Klotho once a week for 4 weeks.

Mice in groups 2 and 3 show improved renal and cardial function measured by serum creatinine, albuminuria, blood pressure and heart rate variability compared to mice in group 1.

Group 3 mice show further improved renal and cardial function measured by serum creatinine, albuminuria, blood pressure and heart rate variability compared with mice in group 2.

Histological and electron microscopic changes of renal architecture are improved in mice in groups 2 and 3 compared to mice in group 1.

Studies in Animal Models for Interrogating Klotho Function when Expressed from Transgenic MSCs in Parkinson Disease (PD):

Although pre-clinical models are yet to be established, the inventors assert that intravenous or intrathecally administered MSC-Klotho will reduce oxidative stress, intravenous or intrathecally administered MSC-Klotho will reduce protein misfolding, protein degradation, protein aggregation, intravenous or intrathecally administered MSC-Klotho will reduce inflammation, and that intravenous or intrathecally administered MSC-Klotho will increase dopaminergic cells in the substantia nigra pars compacta.

Additional experimentation on the basis of the approaches described above is ongoing.

---

What is claimed is:

1. A genetically modified mesenchymal stem cell comprising an exogenous nucleic acid comprising a Klotho-encoding region operably linked to a promoter or promoter/enhancer combination, wherein the genetically modified mesenchymal stem cell exhibits increased Klotho protein expression and secretion compared to an unmodified mesenchymal stem cell.

2. The genetically modified cell according to claim 1, wherein the exogenous nucleic acid is comprised in a viral vector.

3. The genetically modified cell according to claim 1, wherein the promoter is a constitutive promoter.

4. The genetically modified cell according to claim 3, wherein the constitutive promoter is the EFS, PGK or EF1alpha promoter.

5. The genetically modified cell according to claim 1, wherein the Klotho encoding region encodes a protein according to one of SEQ ID NO 6 to 10, or wherein the Klotho encoding region comprises or consists of a sequence according to SEQ ID NO 1 to 5.

6. The genetically modified cell according to claim 1, wherein the Klotho encoding region encodes for a secreted form of the Klotho protein.

7. The genetically modified cell according to claim 6, wherein the secreted form of the Klotho protein possess an amino acid sequence with an identity of at least 80% to SEQ ID NO 8, or an amino acid sequence according to SEQ ID NO 8.

8. The genetically modified cell according to claim 1, wherein the cell is a CD34 negative, self-renewing, multipotent mesenchymal stem cell, capable of adipogenic and osteogenic differentiation.

9. A method of treating a medical condition that will therapeutically benefit from administration of Klotho protein in a patient, the method comprising administering to the patient a therapeutically effective number of genetically modified mesenchymal stem cells according to claim 1 that express and secrete Klotho protein.

10. The method according to claim 9, wherein said therapeutically effective number of genetically modified mesenchymal stem cells is administered subcutaneously.

11. The method according to claim 9, wherein said therapeutically effective number of genetically modified mesenchymal stem cells is administered intrathecally.

12. The method according to claim 8, wherein the patient is treated for a neurodegenerative disease.

13. The method according to claim 9, wherein the patient is treated for cancer.

14. The method according to claim 9, wherein the patient is treated for organ fibrosis.

15. The method according to claim 9, wherein the patient is treated for renal disease.

16. The method according to claim 9, wherein the patient is treated for age-related changes of organs or organ systems.

17. The method according to claim 9, wherein the patient is treated to slow, reverse and/or inhibit ageing.

18. The method according to claim 9, wherein the patient is treated for arteriosclerosis.

19. The method according to claim 9, wherein the patient is treated for dementia.

20. The method according to claim 9, wherein the patient is treated for diabetes mellitus.

21. The method according to claim 9, wherein the patient is treated for erectile dysfunction.

22. The method according to claim 9, wherein the patient is treated for autoimmune diseases or autoimmune-related diseases.

23. The method according to claim 9, wherein the patient is treated for an inflammatory disease of the lung.

24. The method according to claim 9, wherein the patient is treated for sepsis.

25. The method according to claim 9, wherein the genetically modified mesenchymal stem cells are CD34 negative, self-renewing, multipotent mesenchymal stem cells, capable of adipogenic and osteogenic differentiation.

* * * * *

SEQUENCE LISTING

```
<160> NUMBER OF SEQ ID NOS: 10

<210> SEQ ID NO 1
<211> LENGTH: 3039
<212> TYPE: DNA
<213> ORGANISM: Homo sapiens

<400> SEQUENCE: 1
atgcccgcca gcgccccgcc gcgccgcccg cggccgccgc cgccgtcgct gtcgctgctg      60
ctggtgctgc tgggcctggg cggccgccgc ctgcgtgcgg agccgggcga cggcgcgcag     120
acctgggccc gtttctcgcg gcctcctgcc cccgaggccg cgggcctctt ccagggcacc     180
ttccccgacg gcttcctctg ggccgtgggc agcgccgcct accagaccga gggcggctgg     240
cagcagcacg gcaagggtgc gtccatctgg gatacgttca cccaccaccc cctggcaccc     300
```

-continued

```
ccgggagact cccggaacgc cagtctgccg ttgggcgccc cgtcgccgct gcagcccgcc      360
accggggacg tagccagcga cagctacaac aacgtcttcc gcgacacgga ggcgctgcgc      420
gagctcgggg tcactcacta ccgcttctcc atctcgtggg cgcgagtgct ccccaatggc      480
agcgcgggcg tccccaaccg cgaggggctg cgctactacc ggcgcctgct ggagcggctg      540
cgggagctgg gcgtgcagcc cgtggtcacc ctgtaccact gggacctgcc ccagcgcctg      600
caggacgcct acggcggctg ggccaaccgc gccctggccg accacttcag ggattacgcg      660
gagctctgct tccgccactt cggcggtcag gtcaagtact ggatcaccat cgacaacccc      720
tacgtggtgg cctggcacgg ctacgccacc gggcgcctgg cccccggcat ccgggggcagc      780 ccgcggctcg ggtacctggt ggcgcacaac ctcctcctgg ctcatgccaa agtctggcat      840
ctctacaata cttctttccg tcccactcag ggaggtcagg tgtccattgc cctaagctct      900
cactggatca atcctcgaag aatgaccgac cacagcatca agaatgtca aaaatctctg      960 gactttgtac taggttggtt tgccaaaccc gtatttattg atggtgacta tcccgagagc     1020
atgaagaata acctttcatc tattctgcct gattttactg aatctgagaa aaagttcatc     1080
aaaggaactg ctgactttt tgctctttgc tttggaccca ccttgagttt tcaactttg      1140 gaccctcaca tgaagttccg ccaattggaa tctcccaacc tgaggcaact gctttcctgg     1200
attgaccttg aatttaacca tcctcaaata tttattgtgg aaaatggctg gtttgtctca     1260
gggaccacca agagagatga tgccaaatat atgtattacc tcaaaaagtt catcatggaa     1320
accttaaaag ccatcaagct ggatggggtg gatgtcatcg ggtataccgc atggtccctc     1380
atggatggtt tcgagtggca cagaggttac agcatcaggc gtggactctt ctatgttgac     1440
tttctaagcc aggacaagat gttgttgcca aagtcttcag ccttgttcta ccaaaagctg     1500
atagagaaaa atggcttccc tccttttacct gaaaatcagc ccctagaagg gacatttccc     1560
tgtgactttg cttggggagt tgttgacaac tacattcaag tagataccac tctgtctcag     1620
tttaccgacc tgaatgtttta cctgtgggat gtccaccaca gtaaaaggct tattaaagtg     1680
gatggggttg tgaccaagaa gaggaaatcc tactgtgttg actttgctgc catccagccc     1740
cagatcgctt tactccagga aatgcacgtt acacatttc gcttctccct ggactgggcc      1800
ctgattctcc ctctgggtaa ccagtcccag gtgaaccaca ccatcctgca gtactatcgc     1860
tgcatggcca gcgagcttgt ccgtgtcaac atcaccccag tggtggccct gtggcagcct     1920
atggccccga accaaggact gccgcgcctc ctggccaggc agggcgcctg ggagaacccc     1980
tacactgccc tggcctttgc agagtatgcc cgactgtgct ttcaagagct cggccatcac     2040
gtcaagcttt ggataacgat gaatgagccg tatacaagga atatgacata cagtgctggc     2100
cacaaccttc tgaaggccca tgccctggct tggcatgtgt acaatgaaaa gtttaggcat     2160
gctcagaatg ggaaaatatc catagccttg caggctgatt ggatagaacc tgcctgccct     2220
ttctcccaaa aggacaaaga ggtggctgag agagttttgg aatttgacat tggctggctg     2280
gctgagccca tttttcggctc tggagattat ccatgggtga tgagggactg gctgaaccaa     2340
agaaacaatt ttcttcttcc ttatttcact gaagatgaaa aaaagctaat ccagggtacc     2400
tttgactttt tggctttaag ccattatacc accatccttg tagactcaga aaaagaagat     2460
ccaataaaat acaatgatta cctagaagtg caagaaatga ccgacatcac gtggctcaac     2520
tcccccagtc aggtggcggt agtgcccctgg gggttgcgca aagtgctgaa ctggctgaag     2580
ttcaagtacg gagacctccc catgtacata atatccaatg gaatcgatga cgggctgcat     2640
gctgaggacg accagctgag ggtgtattat atgcagaatt acataaacga agctctcaaa     2700
```

```
gcccacatac tggatggtat caatctttgc ggatactttg cttattcgtt taacgaccgc    2760
acagctccga ggtttggcct ctatcgttat gctgcagatc agtttgagcc caaggcatcc    2820
atgaaacatt acaggaaaat tattgacagc aatggtttcc cgggcccaga aactctggaa    2880
agattttgtc cagaagaatt caccgtgtgt actgagtgca gttttttttca cacccgaaag    2940 tctttactgg ctttcatagc ttttctattt tttgcttcta ttatttctct ctcccttata    3000
ttttactact cgaagaaagg cagaagaagt tacaaatag                           3039
```

```
<210> SEQ ID NO 2
<211> LENGTH: 3072
<212> TYPE: DNA
<213> ORGANISM: Homo sapiens

<400> SEQUENCE: 2
```

```
atgcccgcca gcgcccctcc aagaaggcct agacctcctc cacctagcct gagcctgctg      60
ctggtgctgc tgggactggg aggaagaagg ctgagagccg aacctgggga tggcgcccag     120
acatgggcca gattctctag accacccgcc cctgaagccg ccggactgtt tcagggaacc     180
ttccccgatg gcttcctgtg ggccgtggga tctgccgcct atcagactga aggggggctgg     240 cagcagcacg gcaagggcgc ctctatctgg gacaccttca cccaccatcc tctggcccca     300
cccggcgaca gcagaaatgc ttctctgcct ctgggagccc ccagccctct gcagcctgct     360
acaggggatg tggccagcga cagctacaac aacgtgttcc gggacacaga ggccctgcgg     420
gaactgggcg tgacccacta cagattcagc atcagctggg ccagagtgct gcccaatggc     480
tctgccggcg tgcccaatag agagggcctg cggtactacc ggcggctgct ggaaagactg     540
agagaactgg gagtgcagcc cgtcgtgacc ctgtaccatt gggacctgcc ccagagactg     600
caggatgcct atggcggctg ggccaataga gccctggccg accacttcag agactacgcc     660
gagctgtgct tccggcactt tggcggccaa gtgaagtact ggatcaccat cgacaacccc     720
tacgtggtgg cctggcacgg ctatgccaca ggcagactgg cccctggcat cagaggaagc     780
cctagactgg ctacctggt ggcccacaat ctgctgctgg cccacgctaa agtgtggcac     840
ctgtacaaca ccagcttccg gcctacacag ggcggccagg tgtccattgc cctgagcagc     900
cactggatca cccccagacg gatgaccgac cacagcatca agagtgcca gaaaagcctg     960 gacttcgtgc tgggatggtt cgccaagccc gtgttcatcg acggcgacta ccccgagagc    1020
atgaagaaca acctgtccag catcctgccc gacttcaccg agagcgagaa gaagttcatc    1080
aagggcaccg ccgatttctt cgccctgtgc ttcggcccta ccctgagctt ccagctgctg    1140
gacccccaca tgaagttcag acagctggaa agccccaacc tgcggcagct gctgagctgg    1200
atcgacctga aattcaacca cccccagatt ttcatcgtgg aaaacggctg gttcgtgtcc    1260
ggcaccacca gagggacga cgccaagtac atgtattacc tgaaaaagtt tatcatggaa    1320
accctgaagg ccatcaagct ggacggcgtg acgtgatcg ctacacagc ctggtccctg    1380 atggacggct cgagtggca ccggggctac tctatcagac ggggcctgtt ctacgtggac    1440
ttcctgagcc aggacaagat gctgctgcct aagagcagcg ccctgttttta ccagaagctg    1500 atcgagaaga acggcttccc acccctgccc gagaaccagc tctctggaag gaccttcccc    1560
tgcgattttg cctggggcgt ggtggacaac tacatccagg tggacaccac cctgtcccag    1620
ttcaccgacc tgaacgtgta cctgtgggac gtgcaccaca gcaagcggct gattaaggtg    1680
gacggggtcg tgaccaagaa gcggaagtcc tactgcgtgg actttgccgc catccagccc    1740
```

| | | | |
|---|---|---|---|
| cagattgccc | tgctgcagga | aatgcacgtg | acacacttcc | ggttctccct | ggactgggcc | 1800 |
| ctgatcctgc | cactgggcaa | tcagagccaa | gtgaaccaca | ccattctgca | gtactacaga | 1860 |
| tgcatggcct | ccgagctggt | gcgcgtgaac | atcacacctg | tggtggccct | gtggcagccc | 1920 |
| atggccccta | atcagggact | gcctagactg | ctggctagac | agggcgcctg | ggagaaccct | 1980 |
| tacaccgccc | tggcctttgc | cgagtacgcc | cggctgtgtt | tccaggaact | ggggcaccac | 2040 |
| gtgaagctgt | ggatcacaat | gaacgagccc | tacacccgga | acatgaccta | cagcgccgga | 2100 |
| cataacctgc | tgaaggccca | cgccctggct | tggcatgtgt | acaacgagaa | gttccggcac | 2160 |
| gcccagaacg | gcaagatcag | tatcgccctg | caggccgact | ggatcgagcc | cgcctgtccc | 2220 |
| ttcagccaga | aagacaaaga | ggtggccgag | cgggtgctgg | aattcgacat | tggatggctg | 2280 |
| gccgagccca | tcttcggcag | cggcgattac | ccctgggtca | tgcgggactg | gctgaaccag | 2340 |
| cggaacaact | tcctgctgcc | ttactttacc | gaggatgaga | agaaactgat | ccaggggacc | 2400 |
| ttcgacttcc | tggccctgag | ccactacacc | acaatcctgg | tggacagcga | gaaagaggac | 2460 |
| cccatcaagt | acaacgacta | cctggaagtg | caggaaatga | ccgacatcac | ctggctgaat | 2520 |
| agcccctccc | aggtggccgt | ggtgccttgg | ggactgagaa | aggtgctgaa | ttggctgaag | 2580 |
| tttaagtacg | gcgacctgcc | catgtacatc | atcagcaacg | gcatcgacga | tggcctgcac | 2640 |
| gccgaggacg | atcagctgcg | ggtgtactac | atgcagaact | acatcaacga | ggccctgaaa | 2700 |
| gcccacatcc | tggacggcat | caacctgtgc | ggctacttcg | cctacagctt | caacgaccgg | 2760 |
| accgcccta | gattcggcct | gtacagatac | gccgccgacc | agttcgagcc | caaggccagc | 2820 |
| atgaagcact | accggaagat | catcgacagc | aatggcttcc | ctggccccga | gacactggaa | 2880 |
| cggttctgcc | ccgaggaatt | caccgtgtgt | accgagtgca | gcttcttcca | caccagaaag | 2940 |
| tccctgctgg | cttttatcgc | cttcctgttc | ttcgccagca | tcatctccct | gtccctgatc | 3000 |
| ttctactaca | gcaagaaggg | cagacggtcc | tacaagtacc | cctacgacgt | gcccgactac | 3060 |
| gcctgatgat | ga | | | | | 3072 |

```
<210> SEQ ID NO 3
<211> LENGTH: 1650
<212> TYPE: DNA
<213> ORGANISM: Homo sapiens

<400> SEQUENCE: 3
```

| | | | |
|---|---|---|---|
| atgcccgcca | gcgccccgcc | gcgccgcccg | cggccgccgc | cgcagtcgct | gtcgctgctg | 60 |
| ctggtgctgc | tgggcctggg | cggccgccgc | ctgcgtgcgg | agccgggcga | cggcgcgcag | 120 |
| acctgggccc | gtttctcgcg | gcctcctgcc | cccgaggccg | cgggcctctt | ccagggcacc | 180 |
| ttccccgacg | gcttcctctg | ggccgtgggc | agcgccgcct | accagaccga | gggcggctgg | 240 |
| cagcagcacg | gcaagggtgc | gtccatctgg | gacacgttca | cccaccaccc | cctggcaccc | 300 |
| ccgggagact | cccggaacgc | cagtctgccg | ttgggcgccc | cgtcgccgct | gcagcccgcc | 360 |
| accgggacg | tagccagcga | cagctacaac | aacgtcttcc | gcgacacgga | ggcgctgcgc | 420 |
| gagctcgggg | tcactcacta | ccgcttctcc | atctcgtggg | cgcgagtgct | ccccaatggc | 480 |
| agcgcgggc | tccccaaccg | cgagggggctg | cgctactacc | ggcgcctgct | ggagcggctg | 540 |
| cgggagctgg | gcgtgcagcc | cgtggtcacc | ctgtaccact | gggaccctgcc | ccagcgcctg | 600 |
| caggacgcct | acggcggctg | ggccaaccgc | gccctggccg | accacttcag | ggattacgcg | 660 |
| gagctctgct | tccgccactt | cggcggtcag | gtcaagtact | ggatcaccat | cgacaacccc | 720 |
| tacgtggtgg | cctggcacgg | ctacgccacc | gggcgcctgg | cccccggcat | ccggggcagc | 780 |

-continued

```
ccgcggctcg ggtacctggt ggcgcacaac ctcctcctgg ctcatgccaa agtctggcat      840
ctctacaata cttctttccg tcccactcag ggaggtcagg tgtccattgc cctaagctct      900
cactggatca atcctcgaag aatgaccgac cacagcatca aagaatgtca aaaatctctg      960
gactttgtac taggttggtt tgccaaaccc gtatttattg atggtgacta tcccgagagc     1020
atgaagaata acctttcatc tattctgcct gattttactg aatctgagaa aaagttcatc     1080
aaaggaactc ctgacttttt tgctctttgc tttggaccca ccttgagttt tcaacttttg     1140
gaccctcaca tgaagttccg ccaattggaa tctcccaacc tgaggcaact gctttcctgg     1200
attgaccttg aatttaacca tcctcaaata tttattgtgg aaaatggctg gtttgtctca     1260
gggaccacca agagagatga tgccaaatat atgtattacc tcaaaaagtt catcatggaa     1320
accttaaaag ccatcaagct ggatggggtg gatgtcatcg ggtataccgc atggtccctc     1380
atggatggtt tcgagtggca cagaggttac agcatcaggc gtggactctt ctatgttgac     1440
tttctaagcc aggacaagat gttgttgcca aagtcttcag ccttgttcta ccaaaagctg     1500
atagagaaaa atggcttccc tcctttacct gaaaatcagc ccctagaagg gacatttccc     1560
tgtgactttg cttggggagt tgttgacaac tacattcaag taagtcagct gacaaaacca     1620
atcagcagtc tcaccaagcc ctatcactag                                      1650
```

```
<210> SEQ ID NO 4
<211> LENGTH: 3135
<212> TYPE: DNA
<213> ORGANISM: Homo sapiens

<400> SEQUENCE: 4
```

```
atgaagccag gctgtgcggc aggatctcca gggaatgaat ggattttctt cagcactgat       60
gaaataacca cacgctatag gaatacaatg tccaacgggg gattgcaaag atctgtcatc      120
ctgtcagcac ttattctgct acgagctgtt actggattct ctggagatgg aagagctata      180
tggtctaaaa atcctaattt tactccggta aatgaaagtc agctgtttct ctatgacact      240
ttccctaaaa actttttctg gggtattggg actggagcat tgcaagtgga agggagttgg      300
aagaaggatg gaaaaggacc ttctatatgg gatcatttca tccacacaca ccttaaaaat      360
gtcagcagca cgaatggttc cagtgacagt tatatttttc tggaaaaaga cttatcagcc      420
ctggatttta taggagtttc tttttatcaa ttttcaattt cctggccaag gcttttcccc      480
gatggaatag taacagttgc caacgcaaaa ggtctgcagt actacagtac tcttctggac      540
gctctagtgc ttagaaacat tgaacctata gttactttat accactggga tttgcctttg      600
gcactacaag aaaaatatgg ggggtggaaa aatgatacca atagagatat cttcaatgac      660
tatgccacat actgtttcca gatgtttggg gaccgtgtca atattggat tacaattcac      720 aacccatatc tagtggcttg gcatgggtat gggacaggta tgcatgcccc tggagagaag      780
ggaaatttag cagctgtcta cactgtggga cacaacttga tcaaggctca ctcgaaagtt      840
tggcataact acaacacaca tttccgccca catcagaagg gttggttatc gatcacgttg      900
ggatctcatt ggatcgagcc aaaccggtcg gaaaacacga tggatatatt caaatgtcaa      960
caatccatgg tttctgtgct tggatgg ttt gccaacccta tccatggga tggcgactat     1020 ccagaggga tgagaaagaa gttgttctcc gttctaccca ttttctctga agcagagaag     1080
catgagatga gaggcacagc tgatttcttt gcctتтtctt ttggacccaa caacttcaag     1140
cccctaaaca ccatggctaa aatgggacaa aatgtttcac ttaatttaag agaagcgctg     1200
```

```
aactggatta aactggaata caacaaccct cgaatcttga ttgctgagaa tggctggttc      1260
acagacagtc gtgtgaaaac agaagacacc acggccatct acatgatgaa gaatttcctc      1320
agccaggtgc ttcaagcaat aaggttagat gaaatacgag tgtttggtta tactgcctgg      1380
tctctcctgg atggctttga atggcaggat gcttacacca tccgccgagg attattttat      1440
gtggatttta acagtaaaca gaaagagcgg aaacctaagt cttcagcaca ctactacaaa      1500
cagatcatac gagaaaatgg ttttttcttta aaagagtcca cgccagatgt gcagggccag      1560
tttccctgtg acttctcctg gggtgtcact gaatctgttc ttaagcccga gtctgtggct      1620
tcgtccccac agttcagcga tcctcatctg tacgtgtgga acgccactgg caacagactg      1680
ttgcaccgag tggaaggggt gaggctgaaa acacgacccg ctcaatgcac agattttgta      1740
aacatcaaaa aacaacttga gatgttggca agaatgaaag tcacccacta ccggtttgct      1800
ctggattggg cctcggtcct tcccactggc aacctgtccg cggtgaaccg acaggccctg      1860
aggtactaca ggtgcgtggt cagtgagggg ctgaagcttg gcatctccgc gatggtcacc      1920
ctgtattatc cgacccacgc ccacctaggc ctccccgagc ctctgttgca tgccgacggg      1980
tggctgaacc catcgacggc cgaggccttc caggcctacg ctgggctgtg cttccaggag      2040
ctgggggacc tggtgaagct ctggatcacc atcaacgagc ctaaccggct aagtgacatc      2100
tacaaccgct ctggcaacga cacctacggg gcggcgcaca acctgctggt ggcccacgcc      2160
ctggcctggc gcctctacga ccggcagttc aggccctcac agcgcggggc cgtgtcgctg      2220
tcgctgcacg cggactgggc ggaacccgcc aacccctatg ctgactcgca ctggagggcg      2280
gccgagcgct cctgcagtt cgagatcgcc tggttcgccg agccgctctt caagaccggg      2340
gactaccccg cggccatgag ggaatacatt gcctccaagc accgacgggg gctttccagc      2400
tcggccctgc cgcgcctcac cgaggccgaa aggaggctgc tcaagggcac ggtcgacttc      2460
tgcgcgctca accacttcac cactaggttc gtgatgcacg agcagctggc cggcagccgc      2520
tacgactcgg acagggacat ccagtttctg caggacatca cccgcctgag ctcccccacg      2580
cgcctggctg tgattccctg gggggtgcgc aagctgctgc ggtgggtccg gaggaactac      2640
ggcgacatgg acatttacat caccgccagt ggcatcgacg accaggctct ggaggatgac      2700
cggctccgga agtactacct agggaagtac cttcaggagg tgctgaaagc atacctgatt      2760
gataaagtca gaatcaaagg ctattatgca ttcaaactgg ctgaagagaa atctaaaccc      2820
agatttggat tcttcacatc tgattttaaa gctaaatcct caatacaatt ttacaacaaa      2880
gtgatcagca gcaggggctt ccctttgag aacagtagtt ctagatgcag tcagacccaa      2940
gaaaatacag agtgcactgt ctgcttattc cttgtgcaga agaaaccact gatattcctg      3000
ggttgttgct tcttctccac cctggttcta ctcttatcaa ttgccatttt tcaaaggcag      3060
aagagaagaa agttttggaa agcaaaaaac ttacaacaca taccattaaa gaaaggcaag      3120
agagttgtta gctaa                                                       3135
```

<210> SEQ ID NO 5
<211> LENGTH: 1704
<212> TYPE: DNA
<213> ORGANISM: Homo sapiens

<400> SEQUENCE: 5

```
atgaagccag tgtgggtcgc caccccttctg tggatgctac tgctggtgcc caggctgggg       60
gccgcccgga aggggtcccc agaagaggcc tccttctact atggaaccctt ccctcttggc      120 ttctcctggg gcgtgggcag ttctgcctac cagacggagg gcgcctggga ccaggacggg      180
```

-continued

```
aaagggccta gcatctggga cgtcttcaca cacagtggga aggggaaagt gcttgggaat      240
gagacggcag atgtagcctg tgacggctac tacaaggtcc aggaggacat cattctgctg      300
agggaactgc acgtcaacca ctaccgattc tccctgtctt ggccccggct cctgcccaca      360
ggcatccgag ccgagcaggt gaacaagaag ggaatcgaat tctacagtga tcttatcgat      420
gcccttctga gcagcaacat cactcccatc gtgaccttgc accactggga tctgccacag      480
ctgctccagg tcaaatacgg tgggtggcag aatgtgagca tggccaacta cttcagagac      540
tacgccaacc tgtgctttga ggcctttggg accgtgtga agcactggat cacgttcagt      600
gatcctcggg caatggcaga aaaaggctat gagacgggcc accatgcgcc gggcctgaag      660
ctccgcggca ccggcctgta caaggcagca caccacatca ttaaggccca cgccaaagcc      720
tggcattctt ataacaccac gtggcgcagc aagcagcaag tctggtggg aatttcattg      780 aactgtgact gggggggaacc tgtggacatt agtaaccoca aggacctaga ggctgccgag      840
agatacctac agttctgtct gggctggttt gccaacccca tttatgccgg tgactacccc      900
caagtcatga aggactacat tggaagaaag agtgcagagc aaggcctgga gatgtcgagg     960
ttaccggtgt tctcactcca ggagaagagc tacattaaag gcacatccga tttcttggga     1020
ttaggtcatt ttactactcg gtacatcacg gaaaggaact acccctcccg ccaggggccc     1080
agctaccaga cgatcgtga cttgatagag ctggttgacc caaactggcc agatctgggg     1140
tctaaatggc tatattctgt gccatgggga tttaggaggc tccttaactt tgctcagact     1200
caatacggtg atcctcccat atatgtgatg gaaaatggag catctcaaaa attccactgt     1260
actcaattat gtgatgagtg gagaattcaa taccttaaag gatacataaa tgaaatgcta     1320
aaagctataa aagatggtgc taatataaag gggtatactt cctggtctct gttggataag     1380
tttgaatggg agaaaggata ctcagataga tatggattct actatgttga atttaacgac     1440
agaaataagc ctcgctatcc aaaggcttca gttcaatatt acaagaagat tatcattgcc     1500
aatgggtttc ccaatccaag agaggtggaa agttggtacc tcaaagcttt ggaaacttgc     1560
tctatcaaca atcagatgct tgctgcagag cccttgctaa gtcacatgca aatggttacg     1620
gagatcgtgg tacccactgt ctgctccctc tgtgtcctca tcactgctgt tctactaatg     1680
ctcctcctga ggaggcagag ctga                                          1704
```

<210> SEQ ID NO 6
<211> LENGTH: 1012
<212> TYPE: PRT
<213> ORGANISM: Homo sapiens

<400> SEQUENCE: 6

```
Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95
```

```
Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
        130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
        210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
        290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
        370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
```

```
              515                520                525

Asp Asn Tyr Ile Gln Val Asp Thr Thr Leu Ser Gln Phe Thr Asp Leu
    530                535                540

Asn Val Tyr Leu Trp Asp Val His His Ser Lys Arg Leu Ile Lys Val
545                550                555                560

Asp Gly Val Val Thr Lys Lys Arg Lys Ser Tyr Cys Val Asp Phe Ala
                565                570                575

Ala Ile Gln Pro Gln Ile Ala Leu Leu Gln Glu Met His Val Thr His
                580                585                590

Phe Arg Phe Ser Leu Asp Trp Ala Leu Ile Leu Pro Leu Gly Asn Gln
                595                600                605

Ser Gln Val Asn His Thr Ile Leu Gln Tyr Tyr Arg Cys Met Ala Ser
    610                615                620

Glu Leu Val Arg Val Asn Ile Thr Pro Val Val Ala Leu Trp Gln Pro
625                630                635                640

Met Ala Pro Asn Gln Gly Leu Pro Arg Leu Leu Ala Arg Gln Gly Ala
                645                650                655

Trp Glu Asn Pro Tyr Thr Ala Leu Ala Phe Ala Glu Tyr Ala Arg Leu
                660                665                670

Cys Phe Gln Glu Leu Gly His His Val Lys Leu Trp Ile Thr Met Asn
                675                680                685

Glu Pro Tyr Thr Arg Asn Met Thr Tyr Ser Ala Gly His Asn Leu Leu
    690                695                700

Lys Ala His Ala Leu Ala Trp His Val Tyr Asn Glu Lys Phe Arg His
705                710                715                720

Ala Gln Asn Gly Lys Ile Ser Ile Ala Leu Gln Ala Asp Trp Ile Glu
                725                730                735

Pro Ala Cys Pro Phe Ser Gln Lys Asp Lys Glu Val Ala Glu Arg Val
                740                745                750

Leu Glu Phe Asp Ile Gly Trp Leu Ala Glu Pro Ile Phe Gly Ser Gly
                755                760                765

Asp Tyr Pro Trp Val Met Arg Asp Trp Leu Asn Gln Arg Asn Asn Phe
    770                775                780

Leu Leu Pro Tyr Phe Thr Glu Asp Glu Lys Lys Leu Ile Gln Gly Thr
785                790                795                800

Phe Asp Phe Leu Ala Leu Ser His Tyr Thr Thr Ile Leu Val Asp Ser
                805                810                815

Glu Lys Glu Asp Pro Ile Lys Tyr Asn Asp Tyr Leu Glu Val Gln Glu
                820                825                830

Met Thr Asp Ile Thr Trp Leu Asn Ser Pro Ser Gln Val Ala Val Val
                835                840                845

Pro Trp Gly Leu Arg Lys Val Leu Asn Trp Leu Lys Phe Lys Tyr Gly
    850                855                860

Asp Leu Pro Met Tyr Ile Ile Ser Asn Gly Ile Asp Asp Gly Leu His
865                870                875                880

Ala Glu Asp Asp Gln Leu Arg Val Tyr Tyr Met Gln Asn Tyr Ile Asn
                885                890                895

Glu Ala Leu Lys Ala His Ile Leu Asp Gly Ile Asn Leu Cys Gly Tyr
                900                905                910

Phe Ala Tyr Ser Phe Asn Asp Arg Thr Ala Pro Arg Phe Gly Leu Tyr
                915                920                925

Arg Tyr Ala Ala Asp Gln Phe Glu Pro Lys Ala Ser Met Lys His Tyr
    930                935                940
```

-continued

```
Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile  Phe Tyr Tyr Ser Lys  Lys Gly Arg
            995                 1000                1005

Arg Ser  Tyr Lys
        1010

<210> SEQ ID NO 7
<211> LENGTH: 1021
<212> TYPE: PRT
<213> ORGANISM: Homo sapiens

<400> SEQUENCE: 7

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
            50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
            130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
            210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
```

```
       290              295              300

Pro Arg Arg Met Thr Asp His Ser Ile Lys Glu Cys Gln Lys Ser Leu
305              310              315              320

Asp Phe Val Leu Gly Trp Phe Ala Lys Pro Val Phe Ile Asp Gly Asp
             325              330              335

Tyr Pro Glu Ser Met Lys Asn Asn Leu Ser Ser Ile Leu Pro Asp Phe
             340              345              350

Thr Glu Ser Glu Lys Lys Phe Ile Lys Gly Thr Ala Asp Phe Phe Ala
             355              360              365

Leu Cys Phe Gly Pro Thr Leu Ser Phe Gln Leu Leu Asp Pro His Met
         370              375              380

Lys Phe Arg Gln Leu Glu Ser Pro Asn Leu Arg Gln Leu Leu Ser Trp
385              390              395              400

Ile Asp Leu Glu Phe Asn His Pro Gln Ile Phe Ile Val Glu Asn Gly
             405              410              415

Trp Phe Val Ser Gly Thr Thr Lys Arg Asp Asp Ala Lys Tyr Met Tyr
             420              425              430

Tyr Leu Lys Lys Phe Ile Met Glu Thr Leu Lys Ala Ile Lys Leu Asp
         435              440              445

Gly Val Asp Val Ile Gly Tyr Thr Ala Trp Ser Leu Met Asp Gly Phe
         450              455              460

Glu Trp His Arg Gly Tyr Ser Ile Arg Arg Gly Leu Phe Tyr Val Asp
465              470              475              480

Phe Leu Ser Gln Asp Lys Met Leu Leu Pro Lys Ser Ser Ala Leu Phe
             485              490              495

Tyr Gln Lys Leu Ile Glu Lys Asn Gly Phe Pro Pro Leu Pro Glu Asn
         500              505              510

Gln Pro Leu Glu Gly Thr Phe Pro Cys Asp Phe Ala Trp Gly Val Val
         515              520              525

Asp Asn Tyr Ile Gln Val Asp Thr Thr Leu Ser Gln Phe Thr Asp Leu
         530              535              540

Asn Val Tyr Leu Trp Asp Val His His Ser Lys Arg Leu Ile Lys Val
545              550              555              560

Asp Gly Val Val Thr Lys Lys Arg Lys Ser Tyr Cys Val Asp Phe Ala
             565              570              575

Ala Ile Gln Pro Gln Ile Ala Leu Leu Gln Glu Met His Val Thr His
         580              585              590

Phe Arg Phe Ser Leu Asp Trp Ala Leu Ile Leu Pro Leu Gly Asn Gln
         595              600              605

Ser Gln Val Asn His Thr Ile Leu Gln Tyr Tyr Arg Cys Met Ala Ser
         610              615              620

Glu Leu Val Arg Val Asn Ile Thr Pro Val Val Ala Leu Trp Gln Pro
625              630              635              640

Met Ala Pro Asn Gln Gly Leu Pro Arg Leu Leu Ala Arg Gln Gly Ala
             645              650              655

Trp Glu Asn Pro Tyr Thr Ala Leu Ala Phe Ala Glu Tyr Ala Arg Leu
             660              665              670

Cys Phe Gln Glu Leu Gly His His Val Lys Leu Trp Ile Thr Met Asn
         675              680              685

Glu Pro Tyr Thr Arg Asn Met Thr Tyr Ser Ala Gly His Asn Leu Leu
         690              695              700

Lys Ala His Ala Leu Ala Trp His Val Tyr Asn Glu Lys Phe Arg His
705              710              715              720
```

-continued

```
Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
                755                 760                 765

Asp Tyr Pro Trp Val Met Arg Asp Trp Leu Asn Gln Arg Asn Asn Phe
                770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
                835                 840                 845

Pro Trp Gly Leu Arg Lys Val Leu Asn Trp Leu Lys Phe Lys Tyr Gly
                850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
                915                 920                 925

Arg Tyr Ala Ala Asp Gln Phe Glu Pro Lys Ala Ser Met Lys His Tyr
                930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
                980                 985                 990

Ser Ile Ile Ser Leu Ser Leu Ile  Phe Tyr Tyr Ser Lys  Lys Gly Arg
                995                 1000                1005

Arg Ser  Tyr Lys Tyr Pro Tyr  Asp Val Pro Asp Tyr  Ala
        1010                1015                1020

<210> SEQ ID NO 8
<211> LENGTH: 549
<212> TYPE: PRT
<213> ORGANISM: Homo sapiens

<400> SEQUENCE: 8

Met Pro Ala Ser Ala Pro Pro Arg Arg Pro Arg Pro Pro Gln Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
                35                  40                  45

Pro Ala Pro Glu Ala Ala Gly Leu Phe Gln Gly Thr Phe Pro Asp Gly
                50                  55                  60

Phe Leu Trp Ala Val Gly Ser Ala Ala Tyr Gln Thr Glu Gly Gly Trp
```

-continued

```
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
        130                 135                 140

Thr His Tyr Arg Phe Ser Ile Ser Trp Ala Arg Val Leu Pro Asn Gly
    145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
        210                 215                 220

Arg His Phe Gly Gly Gln Val Lys Tyr Trp Ile Thr Ile Asp Asn Pro
    225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
            325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
            405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
            485                 490                 495
```

```
Tyr Gln Lys Leu Ile Glu Lys Asn Gly Phe Pro Pro Leu Pro Glu Asn
        500             505             510

Gln Pro Leu Glu Gly Thr Phe Pro Cys Asp Phe Ala Trp Gly Val Val
        515             520             525

Asp Asn Tyr Ile Gln Val Ser Gln Leu Thr Lys Pro Ile Ser Ser Leu
    530             535             540

Thr Lys Pro Tyr His
545

<210> SEQ ID NO 9
<211> LENGTH: 1044
<212> TYPE: PRT
<213> ORGANISM: Homo sapiens

<400> SEQUENCE: 9

Met Lys Pro Gly Cys Ala Ala Gly Ser Pro Gly Asn Glu Trp Ile Phe
1               5               10              15

Phe Ser Thr Asp Glu Ile Thr Thr Arg Tyr Arg Asn Thr Met Ser Asn
        20              25              30

Gly Gly Leu Gln Arg Ser Val Ile Leu Ser Ala Leu Ile Leu Leu Arg
        35              40              45

Ala Val Thr Gly Phe Ser Gly Asp Gly Arg Ala Ile Trp Ser Lys Asn
    50              55              60

Pro Asn Phe Thr Pro Val Asn Glu Ser Gln Leu Phe Leu Tyr Asp Thr
65              70              75              80

Phe Pro Lys Asn Phe Phe Trp Gly Ile Gly Thr Gly Ala Leu Gln Val
                85              90              95

Glu Gly Ser Trp Lys Lys Asp Gly Lys Gly Pro Ser Ile Trp Asp His
        100             105             110

Phe Ile His Thr His Leu Lys Asn Val Ser Ser Thr Asn Gly Ser Ser
        115             120             125

Asp Ser Tyr Ile Phe Leu Glu Lys Asp Leu Ser Ala Leu Asp Phe Ile
    130             135             140

Gly Val Ser Phe Tyr Gln Phe Ser Ile Ser Trp Pro Arg Leu Phe Pro
145             150             155             160

Asp Gly Ile Val Thr Val Ala Asn Ala Lys Gly Leu Gln Tyr Tyr Ser
                165             170             175

Thr Leu Leu Asp Ala Leu Val Leu Arg Asn Ile Glu Pro Ile Val Thr
        180             185             190

Leu Tyr His Trp Asp Leu Pro Leu Ala Leu Gln Glu Lys Tyr Gly Gly
        195             200             205

Trp Lys Asn Asp Thr Ile Ile Asp Ile Phe Asn Asp Tyr Ala Thr Tyr
    210             215             220

Cys Phe Gln Met Phe Gly Asp Arg Val Lys Tyr Trp Ile Thr Ile His
225             230             235             240

Asn Pro Tyr Leu Val Ala Trp His Gly Tyr Gly Thr Gly Met His Ala
                245             250             255

Pro Gly Glu Lys Gly Asn Leu Ala Ala Val Tyr Thr Val Gly His Asn
        260             265             270

Leu Ile Lys Ala His Ser Lys Val Trp His Asn Tyr Asn Thr His Phe
        275             280             285

Arg Pro His Gln Lys Gly Trp Leu Ser Ile Thr Leu Gly Ser His Trp
    290             295             300

Ile Glu Pro Asn Arg Ser Glu Asn Thr Met Asp Ile Phe Lys Cys Gln
```

-continued

```
305             310             315             320

Gln Ser Met Val Ser Val Leu Gly Trp Phe Ala Asn Pro Ile His Gly
            325             330             335

Asp Gly Asp Tyr Pro Glu Gly Met Arg Lys Lys Leu Phe Ser Val Leu
            340             345             350

Pro Ile Phe Ser Glu Ala Glu Lys His Glu Met Arg Gly Thr Ala Asp
            355             360             365

Phe Phe Ala Phe Ser Phe Gly Pro Asn Asn Phe Lys Pro Leu Asn Thr
    370             375             380

Met Ala Lys Met Gly Gln Asn Val Ser Leu Asn Leu Arg Glu Ala Leu
385             390             395             400

Asn Trp Ile Lys Leu Glu Tyr Asn Asn Pro Arg Ile Leu Ile Ala Glu
            405             410             415

Asn Gly Trp Phe Thr Asp Ser Arg Val Lys Thr Glu Asp Thr Thr Ala
            420             425             430

Ile Tyr Met Met Lys Asn Phe Leu Ser Gln Val Leu Gln Ala Ile Arg
            435             440             445

Leu Asp Glu Ile Arg Val Phe Gly Tyr Thr Ala Trp Ser Leu Leu Asp
    450             455             460

Gly Phe Glu Trp Gln Asp Ala Tyr Thr Ile Arg Arg Gly Leu Phe Tyr
465             470             475             480

Val Asp Phe Asn Ser Lys Gln Lys Glu Arg Lys Pro Lys Ser Ser Ala
            485             490             495

His Tyr Tyr Lys Gln Ile Ile Arg Glu Asn Gly Phe Ser Leu Lys Glu
            500             505             510

Ser Thr Pro Asp Val Gln Gly Gln Phe Pro Cys Asp Phe Ser Trp Gly
            515             520             525

Val Thr Glu Ser Val Leu Lys Pro Glu Ser Val Ala Ser Ser Pro Gln
    530             535             540

Phe Ser Asp Pro His Leu Tyr Val Trp Asn Ala Thr Gly Asn Arg Leu
545             550             555             560

Leu His Arg Val Glu Gly Val Arg Leu Lys Thr Arg Pro Ala Gln Cys
            565             570             575

Thr Asp Phe Val Asn Ile Lys Lys Gln Leu Glu Met Leu Ala Arg Met
            580             585             590

Lys Val Thr His Tyr Arg Phe Ala Leu Asp Trp Ala Ser Val Leu Pro
            595             600             605

Thr Gly Asn Leu Ser Ala Val Asn Arg Gln Ala Leu Arg Tyr Tyr Arg
    610             615             620

Cys Val Val Ser Glu Gly Leu Lys Leu Gly Ile Ser Ala Met Val Thr
625             630             635             640

Leu Tyr Tyr Pro Thr His Ala His Leu Gly Leu Pro Glu Pro Leu Leu
            645             650             655

His Ala Asp Gly Trp Leu Asn Pro Ser Thr Ala Glu Ala Phe Gln Ala
            660             665             670

Tyr Ala Gly Leu Cys Phe Gln Glu Leu Gly Asp Leu Val Lys Leu Trp
            675             680             685

Ile Thr Ile Asn Glu Pro Asn Arg Leu Ser Asp Ile Tyr Asn Arg Ser
    690             695             700

Gly Asn Asp Thr Tyr Gly Ala Ala His Asn Leu Leu Val Ala His Ala
705             710             715             720

Leu Ala Trp Arg Leu Tyr Asp Arg Gln Phe Arg Pro Ser Gln Arg Gly
            725             730             735
```

-continued

```
Ala Val Ser Leu Ser Leu His Ala Asp Trp Ala Glu Pro Ala Asn Pro
        740             745             750

Tyr Ala Asp Ser His Trp Arg Ala Ala Glu Arg Phe Leu Gln Phe Glu
        755             760             765

Ile Ala Trp Phe Ala Glu Pro Leu Phe Lys Thr Gly Asp Tyr Pro Ala
        770             775             780

Ala Met Arg Glu Tyr Ile Ala Ser Lys His Arg Arg Gly Leu Ser Ser
785             790             795             800

Ser Ala Leu Pro Arg Leu Thr Glu Ala Glu Arg Arg Leu Leu Lys Gly
                805             810             815

Thr Val Asp Phe Cys Ala Leu Asn His Phe Thr Thr Arg Phe Val Met
                820             825             830

His Glu Gln Leu Ala Gly Ser Arg Tyr Asp Ser Asp Arg Asp Ile Gln
        835             840             845

Phe Leu Gln Asp Ile Thr Arg Leu Ser Ser Pro Thr Arg Leu Ala Val
        850             855             860

Ile Pro Trp Gly Val Arg Lys Leu Leu Arg Trp Val Arg Arg Asn Tyr
865             870             875             880

Gly Asp Met Asp Ile Tyr Ile Thr Ala Ser Gly Ile Asp Asp Gln Ala
                885             890             895

Leu Glu Asp Asp Arg Leu Arg Lys Tyr Tyr Leu Gly Lys Tyr Leu Gln
                900             905             910

Glu Val Leu Lys Ala Tyr Leu Ile Asp Lys Val Arg Ile Lys Gly Tyr
        915             920             925

Tyr Ala Phe Lys Leu Ala Glu Glu Lys Ser Lys Pro Arg Phe Gly Phe
        930             935             940

Phe Thr Ser Asp Phe Lys Ala Lys Ser Ser Ile Gln Phe Tyr Asn Lys
945             950             955             960

Val Ile Ser Ser Arg Gly Phe Pro Phe Glu Asn Ser Ser Ser Arg Cys
                965             970             975

Ser Gln Thr Gln Glu Asn Thr Glu Cys Thr Val Cys Leu Phe Leu Val
                980             985             990

Gln Lys Lys Pro Leu Ile Phe Leu  Gly Cys Cys Phe Phe  Ser Thr Leu
        995             1000            1005

Val Leu  Leu Leu Ser Ile Ala  Ile Phe Gln Arg Gln  Lys Arg Arg
        1010            1015            1020

Lys Phe  Trp Lys Ala Lys Asn  Leu Gln His Ile Pro  Leu Lys Lys
        1025            1030            1035

Gly Lys  Arg Val Val Ser
        1040
```

```
<210> SEQ ID NO 10
<211> LENGTH: 567
<212> TYPE: PRT
<213> ORGANISM: Homo sapiens

<400> SEQUENCE: 10

Met Lys Pro Val Trp Val Ala Thr Leu Leu Trp Met Leu Leu Leu Val
1               5               10              15

Pro Arg Leu Gly Ala Ala Arg Lys Gly Ser Pro Glu Glu Ala Ser Phe
        20              25              30

Tyr Tyr Gly Thr Phe Pro Leu Gly Phe Ser Trp Gly Val Gly Ser Ser
        35              40              45

Ala Tyr Gln Thr Glu Gly Ala Trp Asp Gln Asp Gly Lys Gly Pro Ser
```

-continued

```
          50               55               60

Ile Trp Asp Val Phe Thr His Ser Gly Lys Gly Lys Val Leu Gly Asn
65              70              75              80

Glu Thr Ala Asp Val Ala Cys Asp Gly Tyr Tyr Lys Val Gln Glu Asp
            85              90              95

Ile Ile Leu Leu Arg Glu Leu His Val Asn His Tyr Arg Phe Ser Leu
            100             105             110

Ser Trp Pro Arg Leu Leu Pro Thr Gly Ile Arg Ala Glu Gln Val Asn
            115             120             125

Lys Lys Gly Ile Glu Phe Tyr Ser Asp Leu Ile Asp Ala Leu Leu Ser
            130             135             140

Ser Asn Ile Thr Pro Ile Val Thr Leu His His Trp Asp Leu Pro Gln
145             150             155             160

Leu Leu Gln Val Lys Tyr Gly Gly Trp Gln Asn Val Ser Met Ala Asn
            165             170             175

Tyr Phe Arg Asp Tyr Ala Asn Leu Cys Phe Glu Ala Phe Gly Asp Arg
            180             185             190

Val Lys His Trp Ile Thr Phe Ser Asp Pro Arg Ala Met Ala Glu Lys
            195             200             205

Gly Tyr Glu Thr Gly His His Ala Pro Gly Leu Lys Leu Arg Gly Thr
            210             215             220

Gly Leu Tyr Lys Ala Ala His His Ile Ile Lys Ala His Ala Lys Ala
225             230             235             240

Trp His Ser Tyr Asn Thr Thr Trp Arg Ser Lys Gln Gln Gly Leu Val
            245             250             255

Gly Ile Ser Leu Asn Cys Asp Trp Gly Glu Pro Val Asp Ile Ser Asn
            260             265             270

Pro Lys Asp Leu Glu Ala Ala Glu Arg Tyr Leu Gln Phe Cys Leu Gly
            275             280             285

Trp Phe Ala Asn Pro Ile Tyr Ala Gly Asp Tyr Pro Gln Val Met Lys
            290             295             300

Asp Tyr Ile Gly Arg Lys Ser Ala Glu Gln Gly Leu Glu Met Ser Arg
305             310             315             320

Leu Pro Val Phe Ser Leu Gln Glu Lys Ser Tyr Ile Lys Gly Thr Ser
            325             330             335

Asp Phe Leu Gly Leu Gly His Phe Thr Thr Arg Tyr Ile Thr Glu Arg
            340             345             350

Asn Tyr Pro Ser Arg Gln Gly Pro Ser Tyr Gln Asn Asp Arg Asp Leu
            355             360             365

Ile Glu Leu Val Asp Pro Asn Trp Pro Asp Leu Gly Ser Lys Trp Leu
            370             375             380

Tyr Ser Val Pro Trp Gly Phe Arg Arg Leu Leu Asn Phe Ala Gln Thr
385             390             395             400

Gln Tyr Gly Asp Pro Pro Ile Tyr Val Met Glu Asn Gly Ala Ser Gln
            405             410             415

Lys Phe His Cys Thr Gln Leu Cys Asp Glu Trp Arg Ile Gln Tyr Leu
            420             425             430

Lys Gly Tyr Ile Asn Glu Met Leu Lys Ala Ile Lys Asp Gly Ala Asn
            435             440             445

Ile Lys Gly Tyr Thr Ser Trp Ser Leu Leu Asp Lys Phe Glu Trp Glu
            450             455             460

Lys Gly Tyr Ser Asp Arg Tyr Gly Phe Tyr Tyr Val Glu Phe Asn Asp
465             470             475             480
```

-continued

```
Arg Asn Lys Pro Arg Tyr Pro Lys Ala Ser Val Gln Tyr Tyr Lys Lys
            485             490             495

Ile Ile Ile Ala Asn Gly Phe Pro Asn Pro Arg Glu Val Glu Ser Trp
            500             505             510

Tyr Leu Lys Ala Leu Glu Thr Cys Ser Ile Asn Asn Gln Met Leu Ala
        515             520             525

Ala Glu Pro Leu Leu Ser His Met Gln Met Val Thr Glu Ile Val Val
        530             535             540

Pro Thr Val Cys Ser Leu Cys Val Leu Ile Thr Ala Val Leu Leu Met
545             550             555             560

Leu Leu Leu Arg Arg Gln Ser
            565
```